(12) United States Patent
Blench et al.

(10) Patent No.: US 8,691,826 B2
(45) Date of Patent: *Apr. 8, 2014

(54) COMPOUNDS

(75) Inventors: Toby Jonathan Blench, Harlow (GB); Christine Edwards, Harlow (GB); Robert Andrew Heald, Harlow (GB); Janusz Jozef Kulagowski, Harlow (GB); Jonathan Mark Sutton, Harlow (GB); Carmelida Capaldi, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/613,952

(22) Filed: Sep. 13, 2012

(65) Prior Publication Data

US 2013/0065913 A1    Mar. 14, 2013

(30) Foreign Application Priority Data

Sep. 14, 2011   (EP) ..................................... 11181201

(51) Int. Cl.
*A61K 31/519*   (2006.01)
*C07D 487/00*   (2006.01)

(52) U.S. Cl.
USPC ...................................... 514/259.1; 544/263

(58) Field of Classification Search
USPC ...................................... 514/259.1; 544/263
See application file for complete search history.

(56) References Cited

U.S. PATENT DOCUMENTS 7,799,782 B2 * 9/2010 Munson et al. ............ 514/234.5

OTHER PUBLICATIONS

U.S. Appl. No. 13/640,001, filed Oct. 8, 2012, Edwards, et al.
U.S. Appl. No. 13/640,004, filed Oct. 8, 2012, Edwards, et al.

* cited by examiner

*Primary Examiner* — Rei-tsang Shiao
(74) *Attorney, Agent, or Firm* — Oblon, Spivak, McClelland, Maier & Neustadt, L.L.P.

(57) ABSTRACT

Compounds of formula (I):

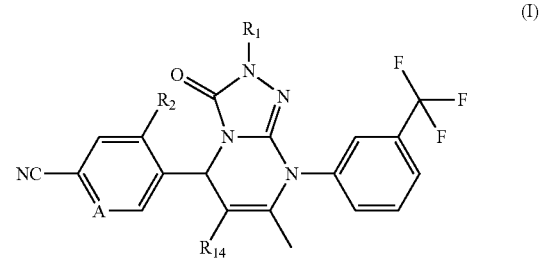

are useful as inhibitors of human neutrophil elastase.

17 Claims, No Drawings

COMPOUNDS

CROSS REFERENCES TO RELATED APPLICATIONS

This application claims priority to European Patent Application No. 11181201.2 filed on Sep. 14, 2011, which is incorporated herein by reference in its entirety.

BACKGROUND OF THE INVENTION

1. Field of the Invention

The present invention relates to heterocyclic compounds, which are pyrimidine derivatives having human neutrophil elastase inhibitory properties, and their use in therapy.

2. Discussion of the Background

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (see Bieth, G. In *Regulation of Matrix accumulation*, Mecham, R. P. (Eds), Academic Press, NY, USA 1986, 217-306, which is incorporated herein by reference in its entirety). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure, both small molecule inhibitors and protein inhibitors of HNE inhibit the inflammatory response and the development of emphysema (see Wright, J. L. et al. *Am. J. Respir. Crit. Care Med.* 2002, 166, 954-960; and Churg, A. et al. *Am. J. Respir. Crit. Care Med.* 2003, 168, 199-207, which are incorporated herein by reference in their entireties). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia, and lung fibrosis. It is also implicated in several cardiovascular diseases in which tissue remodeling is involved, for example, in heart failure and the generation of ischaemic tissue injury following acute myocardial infarction.

COPD is an umbrella term encompassing three different pathological conditions, all of which contribute to limitation of airflow: chronic bronchitis, emphysema, and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (see Thompson, A. B.; Daughton, D.; et al. *Am. Rev. Respir. Dis.* 1989, 140, 1527-1537, which is incorporated herein by reference in its entirety). The major pathogenic determinant in COPD has long been considered to be the protease-anti-protease balance (also known as the "elastase:anti-elastase hypothesis"), in which an imbalance of HNE and endogenous antiproteases such as α1-antitrypsin ($α_1$-AT), secretory leukocyte protease inhibitor (SLPI) and pre-elafin leads to the various inflammatory disorders of COPD. Individuals that have a genetic deficiency of the protease inhibitor α1-antitrypsin develop emphysema that increases in severity over time (see Laurrell, C. B.; Erikkson, S *Scand. J. Clin. Invest.* 1963 15, 132-140, which is incorporated herein by reference in its entirety). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have been disclosed so far in the art. In particular, International Patent Application Nos. WO 2011/110858 and WO 2011/110859, which are incorporated herein by reference in their entireties, describe some pyrimidine derivatives having human neutrophil elastase inhibitory properties and their use in therapy.

Although several HNE inhibitors have been disclosed so far as above reported, there is still a need for further HNE inhibitors. Particularly, there is still a need for further HNE inhibitors endowed with a high potency for HNE enzyme inhibition. Particularly advantageous would also be the identification of further HNE inhibitors endowed with a high potency for HNE enzyme inhibition and which would show an appropriate developability profile as an inhalation treatment. The present invention addresses the above mentioned needs by providing the compounds of the invention.

SUMMARY OF THE INVENTION

Accordingly, it is one object of the present invention to provide novel compounds, which have human neutrophil elastase inhibitory properties, and salts of such a compound.

It is another object of the present invention to provide novel pharmaceutical compositions which contain such a compound or salt thereof.

It is another object of the present invention to provided novel combinations of such a compound or salt thereof with another active agent.

It is another object of the present invention to provide novel methods of treating certain diseases and conditions by administering an effective amount of such a compound or salt thereof.

These and other objects, which will become apparent during the following detailed description, have been achieved by the inventors' discovery that compounds of formula (I):

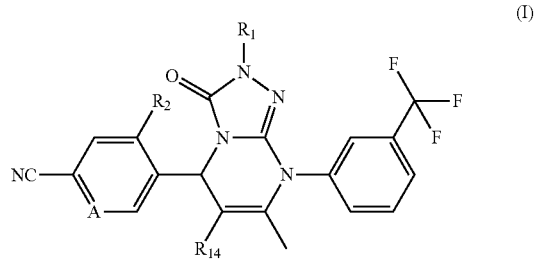

wherein:
A is CH or N;
$R_1$ is selected from the group consisting of:
  hydrogen;
  $(C_1-C_6)$alkyl;
  $NR_7R_8(C_1-C_6)$alkyl;
  $(C_1-C_4)$alkenyl;

phenyl($C_1$-$C_6$)alkyl wherein such phenyl ring is optionally substituted by $NR_{15}R_{16}$($C_1$-$C_6$)alkyl or by $N^+R_{15}R_{16}R_{17}$($C_1$-$C_6$)alkyl;

a group —$CH_2(CH_2)_n OH$;

a group —$(CH_2)_n CONR_5R_6$;

a group —$(CH_2)_n SO_2NR_5R_6$;

a group —$CH_2$—$(CH_2)_n NR_5SO_2R_6$;

a group —$(CH_2)_t$—$(C_6H_4)$—$SO_2(C_1$-$C_4)$alkyl;

a group —$(CH_2)_r SO_2(C_1$-$C_4)$alkyl wherein such ($C_1$-$C_4$) alkyl is optionally substituted by a group —$NR_{15}R_{16}$ or —$N^+R_{15}R_{16}R_{17}$;

a group —$SO_2$-phenyl wherein such phenyl ring is optionally substituted by $NR_7R_8$($C_1$-$C_6$)alkyl; and a group —$(CH_2)_n$—W wherein W is a 5 or 6-membered heteroaryl ring which is optionally substituted by a group —$SO_2(C_1$-$C_4)$alkyl;

n is 1, 2 or 3;

t is zero, 1, 2 or 3;

r is zero, 1, 2, 3 or 4;

$R_5$ is selected in the group consisting of: hydrogen, ($C_1$-$C_6$)alkyl, $NR_{16}R_{15}$($C_1$-$C_6$)alkyl and $N^+R_{17}R_{15}R_{16}$($C_1$-$C_6$)alkyl;

$R_6$ is hydrogen or ($C_1$-$C_6$)alkyl;

$R_7$ is selected in the group consisting of: hydrogen, ($C_1$-$C_6$)alkyl, ($C_1$-$C_6$)alkylcarbonyl, —$SO_2(C_1$-$C_4)$alkyl, and $NR_{16}R_{15}$($C_1$-$C_6$)alkyl;

$R_8$ is hydrogen or ($C_1$-$C_6$)alkyl;

alternatively, $R_7$ and $R_8$, together with the nitrogen atom to which they are attached, form a ($C_5$-$C_7$)heterocycloalkyl ring system which is optionally substituted by one or more groups ($C_1$-$C_6$) alkyl and oxo;

$R_{16}$ is hydrogen or ($C_1$-$C_6$)alkyl;

$R_{15}$ is hydrogen or ($C_1$-$C_6$)alkyl;

$R_{17}$ is hydrogen or ($C_1$-$C_6$)alkyl;

$R_2$ is hydrogen or —$SO_2R_4$, wherein $R_4$ is selected from: optionally substituted ($C_1$-$C_6$)alkyl, hydroxyl($C_1$-$C_6$)alkyl, amino, mono- or di($C_1$-$C_4$)alkylamino wherein ($C_1$-$C_4$)alkyl may be optionally substituted, optionally substituted ($C_3$-$C_6$)-cycloalkyl, halogen and optionally substituted phenyl;

$R_{14}$ is a group cyano or a group —C(O)—$XR_3$;

X is a divalent group selected from: —O—, —($CH_2$)— and —NH—;

$R_3$ is a group selected in the list consisting of:
hydrogen;
($C_1$-$C_6$)alkyl;
a group of formula [$Alk^1$]-Z,
wherein $Alk^1$ represents a ($C_1$-$C_4$)alkylene radical, and Z is:
(i) —$NR_9R_{10}$ wherein $R_9$ and $R_{10}$ are independently hydrogen, optionally substituted ($C_1$-$C_6$)alkyl or an optionally substituted ($C_3$-$C_6$)cycloalkyl group; or, taken together with the nitrogen to which they are attached, form an optionally substituted monocyclic ($C_5$-$C_7$)heterocyclic ring which may contain a further heteroatom selected from N, O and S;
or
(ii) —$N^+R_{11}R_{12}R_{13}$ wherein $R_{11}$, $R_{12}$ and $R_{13}$ are each independently optionally substituted ($C_1$-$C_6$)alkyl or optionally substituted ($C_3$-$C_6$)cycloalkyl group; or any two of $R_{11}$, $R_{12}$ and $R_{13}$ taken together with the nitrogen to which they are attached form an optionally substituted monocyclic ($C_5$-$C_7$)heterocyclic ring which may contain a further heteroatom selected from N, O and S and the other of $R_{11}$, $R_{12}$ and $R_{13}$ is an optionally substituted ($C_1$-$C_6$)alkyl or an optionally substituted ($C_3$-$C_6$)cycloalkyl group; and a radical of formula —$(CH_2)_q$-[Q]-$(CH_2)_p$ Z wherein Z is as above defined, q is an integer ranging from zero to 3, p is an integer ranging from zero to 3 and Q represents a divalent group selected from: —O—, optionally substituted phenylene, optionally substituted ($C_5$-$C_7$)heterocycloalkylene, optionally substituted ($C_3$-$C_6$)cycloalkyl and optionally substituted pyridinylene;

wherein if one or more groups $N^+R_{11}R_{12}R_{13}$ ($C_1$-$C_6$)alkyl- or $N^+R_{15}R_{16}R_{17}$ ($C_1$-$C_6$)alkyl- are present, they form quaternary salts with a pharmaceutically acceptable counter ion;

and wherein groups $R_5$, $R_6$, $R_7$, $R_8$, $R_{15}$, $R_{16}$, $R_{17}$, and n may assume the same or different meanings at each occurrence, if present in more than one group;

with the proviso that the compound of formula (I) is not:
5-(4-Cyanophenyl)-2-(2-dimethylaminoethyl)-7-methyl-3-oxo-8-(3-trifluoromethylphenyl)-2,3,5,8-tetrahydro[1,2,4]triazolo[4,3-a]pyrimidine-6-carboxylic acid methyl ester;

5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid 2-dimethylaminoethyl ester;

{2-[5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carbonyloxy]ethyl}-trimethylammonium;

5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid;

and pharmaceutically acceptable salts thereof and N-oxides thereof are inhibitors of HNE, and are useful in the treatment of diseases or conditions in which HNE activity plays a part.

DETAILED DESCRIPTION OF THE PREFERRED EMBODIMENTS

Thus, in one aspect, the present invention provides compounds of formula (I), and pharmaceutically acceptable salts thereof:

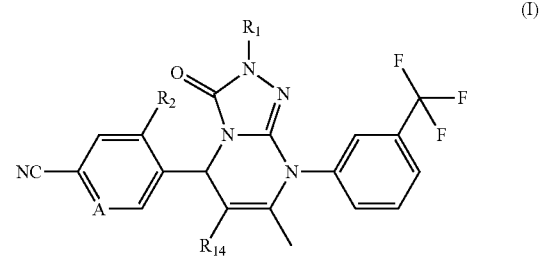

(I)

wherein:
A is CH or N;
$R_1$ is selected from the group consisting of:
hydrogen;
($C_1$-$C_6$)alkyl;
$NR_7R_8$($C_1$-$C_6$)alkyl;
($C_1$-$C_4$)alkenyl;
phenyl($C_1$-$C_6$)alkyl wherein such phenyl ring is optionally substituted by $NR_{15}R_{16}$($C_1$-$C_6$)alkyl or by $N^+R_{15}R_{16}R_{17}$($C_1$-$C_6$)alkyl;
a group —$CH_2(CH_2)_n OH$;
a group —$(CH_2)_n CONR_5R_6$;
a group —$(CH_2)_n SO_2NR_5R_6$;
a group —$CH_2$—$(CH_2)_n NR_5SO_2R_6$;
a group —$(CH_2)_t$—$(C_6H_4)$—$SO_2(C_1$-$C_4)$alkyl;

a group —(CH$_2$)$_r$SO$_2$(C$_1$-C$_4$)alkyl wherein such (C$_1$-C$_4$)alkyl is optionally substituted by a group —NR$_{15}$R$_{16}$ or —N$^+$R$_{15}$R$_{16}$R$_{17}$;

a group —SO$_2$-phenyl wherein such phenyl ring is optionally substituted by NR$_7$R$_8$(C$_1$-C$_6$)alkyl; and a group —(CH$_2$)n-W wherein W is a 5-6-membered heteroaryl ring which is optionally substituted by a group —SO$_2$(C$_1$-C$_4$)alkyl;

n is 1, 2 or 3;

t is zero, 1, 2 or 3;

r is zero, 1, 2, 3 or 4;

R$_5$ is selected in the group consisting of: hydrogen, (C$_1$-C$_6$)alkyl, NR$_{16}$R$_{15}$(C$_1$-C$_6$)alkyl and N$^+$R$_{17}$R$_{15}$R$_{16}$(C$_1$-C$_6$)alkyl;

R$_6$ is hydrogen or (C$_1$-C$_6$)alkyl;

R$_7$ is selected in the group consisting of: hydrogen, (C$_1$-C$_6$)alkyl, (C$_1$-C$_6$)alkylcarbonyl, —SO$_2$(C$_1$-C$_4$)alkyl, and NR$_{16}$R$_{15}$(C$_1$-C$_6$)alkyl;

R$_8$ is hydrogen or (C$_1$-C$_6$)alkyl;

alternatively, R$_7$ and R$_8$, together with the nitrogen atom to which they are attached, form a (C$_5$-C$_7$)heterocycloalkyl ring system which is optionally substituted by one or more groups (C$_1$-C$_6$)alkyl and oxo;

R$_{16}$ is hydrogen or (C$_1$-C$_6$)alkyl;

R$_{15}$ is hydrogen or (C$_1$-C$_6$)alkyl;

R$_{17}$ is hydrogen or (C$_1$-C$_6$)alkyl;

R$_2$ is hydrogen or —SO$_2$R$_4$, wherein R$_4$ is selected from: optionally substituted (C$_1$-C$_6$)alkyl, hydroxyl(C$_1$-C$_6$)alkyl, amino, mono- or di(C$_1$-C$_4$)alkylamino wherein (C$_1$-C$_4$)alkyl may be optionally substituted, optionally substituted (C$_3$-C$_6$)-cycloalkyl, halogen and optionally substituted phenyl;

R$_{14}$ is a group cyano or a group —C(O)—XR$_3$;

X is a divalent group selected from: —O—, —(CH$_2$)— and —NH—;

R$_3$ is a group selected in the list consisting of:
hydrogen;
(C$_1$-C$_6$)alkyl;
a group of formula [Alk$^1$]-Z,
wherein Alk$^1$ represents a (C$_1$-C$_4$)alkylene radical, and Z is:
(i) —NR$_9$R$_{10}$ wherein R$_9$ and R$_{10}$ are independently hydrogen, optionally substituted (C$_1$-C$_6$)alkyl or an optionally substituted (C$_3$-C$_6$)cycloalkyl group; or, taken together with the nitrogen to which they are attached, form an optionally substituted monocyclic (C$_5$-C$_7$)heterocyclic ring which may contain a further heteroatom selected from N, O and S;
or
(ii) —N$^+$R$_{11}$R$_{12}$R$_{13}$ wherein R$_{11}$, R$_{12}$ and R$_{13}$ are each independently optionally substituted (C$_1$-C$_6$)alkyl or optionally substituted (C$_3$-C$_6$)cycloalkyl group; or any two of R$_{11}$, R$_{12}$ and R$_{13}$ taken together with the nitrogen to which they are attached form an optionally substituted monocyclic (C$_5$-C$_7$)heterocyclic ring which may contain a further heteroatom selected from N, O and S and the other of R$_{11}$, R$_{12}$ and R$_{13}$ is an optionally substituted (C$_1$-C$_6$)alkyl or an optionally substituted (C$_3$-C$_6$)cycloalkyl group; and
a radical of formula —(CH$_2$)$_q$-[Q]-(CH$_2$)$_p$Z wherein Z is as above defined, q is an integer ranging from zero to 3, p is an integer ranging from zero to 3 and Q represents a divalent group selected from: —O—, optionally substituted phenylene, optionally substituted (C$_5$-C$_7$)heterocycloalkylene, optionally substituted (C$_3$-C$_6$)cycloalkyl and optionally substituted pyridinylene;

wherein if one or more groups N$^+$R$_{11}$R$_{12}$R$_{13}$(C$_1$-C$_6$)alkyl- or N$^+$R$_{15}$R$_{16}$R$_{17}$(C$_1$-C$_6$)alkyl- are present, they form quaternary salts with a pharmaceutically acceptable counter ion;

and wherein groups R$_5$, R$_6$, R$_7$, R$_8$, R$_{15}$, R$_{16}$, R$_{17}$, and n may assume the same or different meanings at each occurrence, if present in more than one group;

with the proviso that the compound of formula (I) is not:
5-(4-Cyanophenyl)-2-(2-dimethylaminoethyl)-7-methyl-3-oxo-8-(3-trifluoromethylphenyl)-2,3,5,8-tetrahydro[1,2,4]triazolo[4,3-a]pyrimidine-6-carboxylic acid methyl ester;

5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid 2-dimethylaminoethyl ester;

{2-[5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carbonyloxy]ethyl}-trimethylammonium;

5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid;

and pharmaceutically acceptable salts thereof and N-oxides thereof.

In one embodiment, the present invention provides a compound of formula (ID):

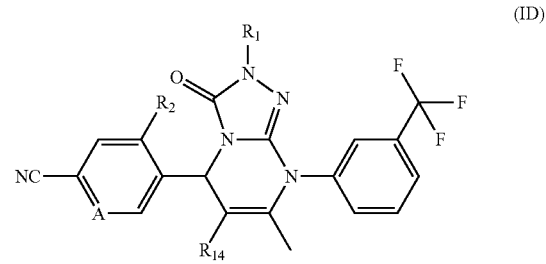

wherein
A is CH or N;
R$_1$ is selected from the group consisting of:
hydrogen;
(C$_1$-C$_6$)alkyl;
NR$_7$R$_8$(C$_1$-C$_6$)alkyl;
(C$_1$-C$_4$)alkenyl;
phenyl(C$_1$-C$_6$)alkyl;
a group —CH$_2$(CH$_2$)$_n$OH;
a group —(CH$_2$)$_n$CONR$_5$R$_6$;
a group —(CH$_2$)$_n$SO$_2$NR$_5$R$_6$; and
a group —CH$_2$—(CH$_2$)$_n$NR$_5$SO$_2$R$_6$;
n is 1, 2 or 3;
R$_5$ is hydrogen or (C$_1$-C$_6$)alkyl;
R$_6$ is hydrogen or (C$_1$-C$_6$)alkyl;
R$_7$ is hydrogen or (C$_1$-C$_6$)alkyl;
R$_8$ is hydrogen or (C$_1$-C$_6$)alkyl;
R$_2$ is hydrogen or —SO$_2$R$_4$, wherein R$_4$ is selected from: optionally substituted (C$_1$-C$_6$)alkyl, hydroxyl(C$_1$-C$_6$)alkyl, amino, mono- or di(C$_1$-C$_4$)alkylamino wherein (C$_1$-C$_4$)alkyl may be optionally substituted, optionally substituted C$_3$-C$_6$-cycloalkyl, halogen and optionally substituted phenyl;
R$_{14}$ is a group a group —C(O)—XR$_3$;
X is a divalent group selected from: —O—, —(CH$_2$)— and —NH—;
R$_3$ is a group selected from:
(C$_1$-C$_6$)alkyl;
a group of formula -[Alk$^1$]-Z,
wherein Alk$^1$ represents a (C$_1$-C$_4$)alkylene radical, and Z is:
(i) —NR$_9$R$_{10}$ wherein R$_9$ and R$_{10}$ are independently hydrogen, optionally substituted (C$_1$-C$_6$)alkyl or an optionally substituted (C$_3$-C$_6$)cycloalkyl group; or, taken together with the nitrogen to which they are attached, form an optionally substituted monocyclic (C$_5$-C$_7$)heterocyclic ring which may contain a further heteroatom selected from N, O and S;
or
(ii) —N$^+$R$_{11}$R$_{12}$R$_{13}$ wherein R$_{11}$, R$_{12}$ and R$_{13}$ are each independently optionally substituted (C$_1$-C$_6$)alkyl or optionally substituted (C$_3$-C$_6$)cycloalkyl group; or any two of R$_{11}$, R$_{12}$ and R$_{13}$ taken together with the nitrogen to which they are attached form an optionally substituted monocyclic (C$_5$-C$_7$)heterocyclic ring which may contain a further heteroatom selected from N, O and S and the other of R$_{11}$, R$_{12}$ and R$_{13}$ is an optionally substituted (C$_1$-C$_6$)alkyl or an optionally substituted (C$_3$-C$_6$)cycloalkyl group; and a radical of formula —(CH$_2$)$_q$-[Q]-(CH$_2$)$_p$ Z wherein Z is as above defined, q is an integer ranging from zero to 3, p is an integer ranging from zero to 3 and Q represents a divalent group selected from: —O—, optionally substituted phenylene, optionally substituted (C$_5$-C$_7$)heterocycloalkylene, optionally substituted (C$_3$-C$_6$)cycloalkyl and optionally substituted pyridinylene;
or a pharmaceutically acceptable salt thereof;
with the proviso that the compound of formula (I) is not:
5-(4-Cyanophenyl)-2-(2-dimethylaminoethyl)-7-methyl-3-oxo-8-(3-trifluoromethylphenyl)-2,3,5,8-tetrahydro[1,2,4]triazolo[4,3-a]pyrimidine-6-carboxylic acid methyl ester;
5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid 2-dimethylaminoethyl ester; or
{2-[5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carbonyloxy]ethyl}-trimethylammonium.

Compounds of formula (I) may be prepared in the form of salts, particularly pharmaceutically acceptable salts, N-oxides, hydrates, solvates and polymorphs thereof. Any reference to a compound herein, or reference to "compounds of the invention", "compounds of formula (I)", and the like includes such compounds whether or not in salt, N-oxide, hydrate, solvate or polymorphic form.

It will be appreciated by a person skilled in the art that certain groups included in compounds of formula (I) may exist in one or more tautomeric forms. The present invention includes within its scope all such tautomeric forms, including mixtures. In particular, it will be appreciated by a person skilled in the art that compounds of formula (I), when R$_1$ is hydrogen, may exist in two tautomeric forms as below reported:

Both tautomeric forms are intended to be included within the scope of compounds of the present invention.

Compounds of the present invention may be used in the treatment or prevention of diseases in which HNE is implicated, for example chronic obstructive pulmonary disease (COPD), bronchiectasis, chronic bronchitis, lung fibrosis, pneumonia, acute respiratory distress syndrome (ARDS), pulmonary emphysema, smoking-induced emphysema, and cystic fibrosis.

Hence other aspects of the invention include (i) pharmaceutical compositions comprising a compound of the present invention and a pharmaceutically acceptable carrier or excipient; and (ii) the use of a compound of the present invention for the manufacture of a medicament for the treatment or prevention of a disease or condition in which HNE is implicated.

The term "(C$_a$-C$_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "(C$_a$-C$_b$)alkenyl" wherein a and b are integers refers to a straight or branched chain alkenyl moiety having from a to b carbon atoms having at least one double bond of either E or Z stereochemistry where applicable. Thus when a is 2 and b is 6, for example, the term includes, for example, vinyl, allyl, 1- and 2-butenyl and 2-methyl-2-propenyl.

The expressions "NR$_{15}$R$_{16}$(C$_a$-C$_b$)alkyl" or "NR$_7$R$_8$(C$_a$-C$_b$)alkyl", wherein a and b are as above defined, refer to the above defined "(C$_a$-C$_b$)alkyl" groups wherein one hydrogen atom is replaced by a group —NR$_{15}$R$_{16}$ or —NR$_7$R$_8$ respectively.

The expression "N$^+$R$_{15}$R$_{16}$R$_{17}$(C$_a$-C$_b$)alkyl" wherein a and b are as above defined, refer to the above defined "(C$_a$-C$_b$)alkyl" groups wherein one hydrogen atom is replaced by a group —N$^+$R$_{15}$R$_{16}$R$_{17}$.

The expressions "mono (C$_a$-C$_b$)alkyl" or "di (C$_a$-C$_b$)alkyl amino", wherein a and b are integers, refer to an amino group wherein, respectively, one or both hydrogen atoms are replaced by a group (C$_a$-C$_b$)alkyl.

The expression "phenyl(C$_a$-C$_b$)alkyl" refers to the above defined "(C$_a$-C$_b$)alkyl" radicals wherein one hydrogen atom is replaced by a phenyl group.

The term "divalent (C$_a$-C$_b$)alkylene radical" wherein a and b are integers refers to a saturated hydrocarbon chain having from a to b carbon atoms as above defined and two unsatisfied valences.

The term "(C$_a$-C$_b$)cycloalkyl", wherein a and b are integers, refers to saturated monocyclic hydrocarbon groups containing from a to b ring carbon atoms. Examples include cyclopropyl, cyclobutyl, cyclopentyl, cyclohexyl and cycloheptyl.

The expression "(C$_a$-C$_b$)heterocycloalkyl" refers to monocyclic (C$_a$-C$_b$)cycloalkyl groups, in which at least one ring

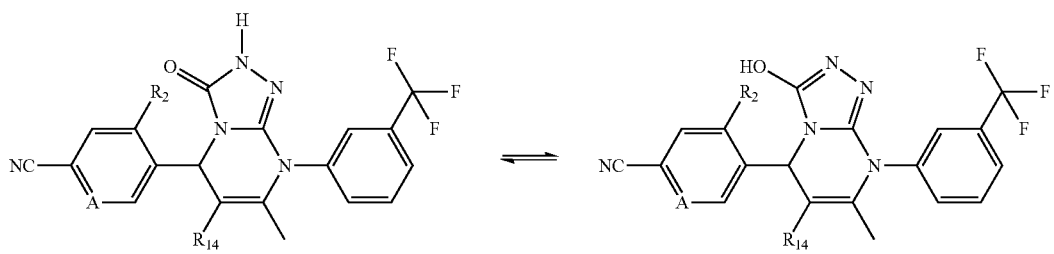

carbon atom is replaced by a heteroatom (e.g. N, NH, S, or O). Examples of $(C_a-C_b)$heterocycloalkyl are represented by: pyrrolidinyl, thiazolidinyl, piperazinyl, piperidinyl, morpholinyl, and thiomorpholinyl.

By analogy, the expression "$(C_a-C_b)$heterocycloalkylene" refers to a divalent $(C_a-C_b)$heterocycloalkyl radical (such as for example pyrrolidinene) wherein "$(C_a-C_b)$heterocycloalkyl group is as above defined.

The expression "heteroaryl" refers to mono or bi-cyclic ring systems with 5 to 11 ring atoms, in which at least one ring is aromatic and in which at least one ring atom is a heteroatom (e.g. N, NH, S, or O).

Examples of suitable 5 and 6-membered heteroaryl monocyclic systems include, for instance thiophene (thiophenyl), benzene (phenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), imidazolidine (imidazolidinyl), furan (furanyl) radicals, and the like.

The term "$(C_a-C_b)$ alkoxyl" wherein a and b are integers, refers to straight-chained and branched alkoxy groups wherein the number of constituent carbon atoms is in the range from a to b. Particular alkyl groups are methoxyl, ethoxyl, n-propoxyl, isopropoxyl and t-butoxyl.

The symbol "—$C_6H_4$—" indicates a divalent phenylene ring radical.

The expression "$(C_a-C_b)$alkylcarbonyl" refers to —CO $(C_a-C_b)$alkyl groups wherein the group "$(C_a-C_b)$alkyl" has the meaning above defined.

The expressions "hydroxy$(C_a-C_b)$alkyl" refer to the above defined "$(C_a-C_b)$alkyl" radicals wherein one hydrogen atom is replaced by a group —OH.

Unless otherwise specified, the term "substituted" as applied to any moiety herein means substituted with up to four compatible substituents, each of which independently may be, for example, $(C_1-C_6)$alkyl, $(C_1-C_6)$alkoxyl, hydroxyl, hydroxyl-$C_1-C_6$-alkyl, halo (including fluoro, bromo, and chloro), trifluoromethyl, trifluoromethoxy. An "optional substituent" may be one of the foregoing substituent groups.

The term "salt" includes base addition and acid addition salts.

The term "Pharmaceutically acceptable salts" refers to derivatives of compounds of formula (I) wherein the parent compound is suitably modified by converting any of the free acid or basic group, if present, into the corresponding addition salt with any base or acid conventionally intended as being pharmaceutically acceptable.

Compounds of the present invention which are acidic can form salts, including pharmaceutically acceptable salts, with bases such as alkali metal hydroxides, e.g. sodium and potassium hydroxides; alkaline earth metal hydroxides, e.g., calcium, barium, and magnesium hydroxides; with organic bases, e.g., N-methyl-D-glucamine, choline tris(hydroxymethyl)amino-methane, L-arginine, L-lysine, N-ethyl piperidine, dibenzylamine, and the like. Those compounds which are basic can form salts, including pharmaceutically acceptable salts with inorganic acids, e.g. with hydrohalic acids such as hydrochloric or hydrobromic acids, sulfuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids, and the like. Those compounds which have quaternary nitrogen can also form quaternary salts with a pharmaceutically acceptable counter-ion such as chloride, bromide, acetate, formate, p-toluenesulfonate, succinate, hemi-succinate, naphthalene-bis sulfonate, methanesulfonate, xinafoate, and the like.

Where the compounds of the invention have at least one stereogenic center, they may exist as enantiomers. When the compounds according to the invention possess two or more stereogenic centers, they may additionally exist as diastereoisomers. It is to be understood that all such isomers and mixtures thereof in any proportion are encompassed within the scope of the present invention.

It will be apparent that compounds of general formula (I) contain at least contain one stereogenic center, namely represented by the carbon atom (1) with an asterisk below, and therefore exist as optical stereoisomers:

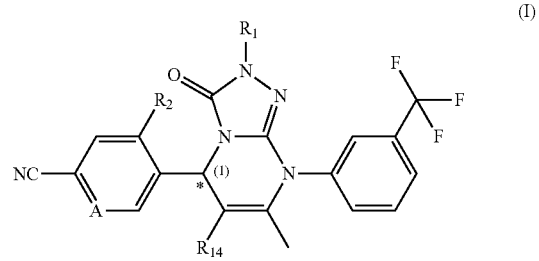

In one embodiment, the present invention is directed to compounds of formula (I)', which are compounds of formula (I) as above defined where the absolute configuration of carbon (1) is that shown here below:

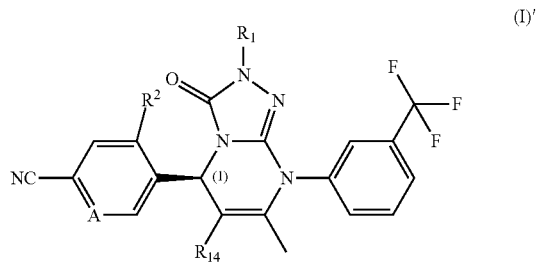

In another embodiment, the present invention is directed to compounds of formula (I)", which are compounds of formula (I) as above defined where the absolute configuration of carbon (1) is that shown herebelow:

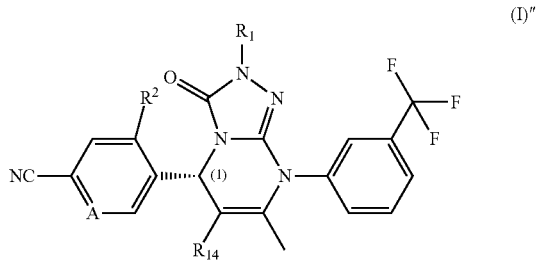

The absolute configuration for carbon (1) is assigned on the basis of Cahn-Ingold-Prelog nomenclature based on groups' priorities.

It is to be understood that all preferred groups or embodiments described here below for compounds of formula (I)

may be combined among each other and apply as well to compounds of formula (I)', (I)", (IA), (IB), (IC), and (IE), mutatis mutandis.

In one embodiment, for compounds of formula (I) A is CH.

In one embodiment, $R_2$ is hydrogen or a group —$SO_2R_4$, wherein $R_4$ is $(C_1-C_6)$alkyl. In a preferred embodiment, $R_2$ is hydrogen.

In one embodiment, $R_4$ is optionally substituted $(C_1-C_6)$alkyl. In another embodiment, $R_4$ is $(C_1-C_6)$alkyl.

In one embodiment, $R_{14}$ is a group cyano or a group —C(O)—$XR_3$. In a preferred embodiment, $R_{14}$ is a group —C(O)—$XR_3$.

In one embodiment, X is a divalent group —O— or —NH—. In another embodiment, X is a divalent —O—.

In one embodiment, $R_3$ is a group selected from the group consisting of:
hydrogen;
$(C_1-C_6)$alkyl; and
a radical of formula -[$Alk^1$]-Z wherein $Alk^1$ represents a $(C_1-C_4)$alkylene radical and Z is:
(i) —$NR_9R_{10}$ wherein $R_9$ and $R_{10}$ are independently hydrogen, optionally substituted $(C_1-C_6)$alkyl or an optionally substituted $(C_3-C_6)$cycloalkyl group; or, taken together with the nitrogen to which they are attached form an optionally substituted monocyclic $(C_5-C_7)$heterocyclic ring which may contain a further heteroatom selected from N, O and S; or
(ii) —$N^+R_{11}R_{12}R_{13}$ wherein $R_{11}$, $R_{12}$ and $R_{13}$ are each independently optionally substituted $(C_1-C_6)$alkyl or optionally substituted $(C_3-C_6)$cycloalkyl group; or any two of $R_{11}$, $R_{12}$ and $R_{13}$ taken together with the nitrogen to which they are attached form an optionally substituted monocyclic $(C_5-C_7)$ heterocyclic ring which may contain a further heteroatom selected from N, O and S and the other of $R_{11}$, $R_{12}$ and $R_{13}$ is an optionally substituted $(C_1-C_6)$alkyl or an optionally substituted $(C_3-C_6)$cycloalkyl group.

In a preferred embodiment, $R_3$ is a group selected in the list consisting of:
hydrogen;
$(C_1-C_6)$alkyl; and
a radical of formula -[$Alk^1$]-Z wherein $Alk^1$ represents a $(C_1-C_4)$alkylene radical and Z is:
(i) —$NR_9R_{10}$ wherein $R_9$ and $R_{10}$ are independently hydrogen, $(C_1-C_6)$alkyl or $(C_3-C_6)$cycloalkyl group; or, taken together with the nitrogen to which they are attached form a monocyclic $(C_5-C_7)$heterocyclic ring which may contain a further heteroatom selected from N, O and S; or
(ii) —$N^+R_{11}R_{12}R_{13}$ wherein $R_{11}$, $R_{12}$ and $R_{13}$ are each independently $(C_1-C_6)$alkyl or $(C_3-C_6)$cycloalkyl group; or any two of $R_{11}$, $R_{12}$ and $R_{13}$ taken together with the nitrogen to which they are attached form a monocyclic $(C_5-C_7)$heterocyclic ring which may contain a further heteroatom selected from N, O and S and the other of $R_{11}$, $R_{12}$ and $R_{13}$ is $(C_1-C_6)$alkyl or a $(C_3-C_6)$cycloalkyl group.

In another preferred embodiment, $R_3$ is a group selected in the list consisting of:
hydrogen;
$(C_1-C_6)$alkyl; and
a radical of formula -[$Alk^1$]-Z wherein $Alk^1$ represents a $(C_1-C_4)$alkylene radical and Z is:
(i) —$NR_9R_{10}$ wherein $R_9$ and $R_{10}$ are independently hydrogen or optionally substituted $(C_1-C_6)$alkyl;
or
(ii) —$N^+R_{11}R_{12}R_{13}$ wherein $R_{11}$, $R_{12}$ and $R_{13}$ are each independently optionally substituted $(C_1-C_6)$alkyl.

In a further preferred embodiment, $R_3$ is $(C_1-C_6)$alkyl.

In a still preferred embodiment, embodiment, $R_3$ is a group selected in the list consisting of:
hydrogen;
$(C_1-C_6)$alkyl; and
a radical of formula -[$Alk^1$]-Z wherein $Alk^1$ represents a $(C_1-C_4)$alkylene radical and Z is:
(i) —$NR_9R_{10}$ wherein $R_9$ and $R_{10}$ are independently hydrogen or optionally substituted $(C_1-C_6)$alkyl;
or
(ii) —$N^+R_{11}R_{12}R_{13}$ wherein $R_{11}$, $R_{12}$ and $R_{13}$ are each independently optionally substituted $(C_1-C_6)$alkyl;
and X is a divalent —O—.

In one embodiment, for compounds of formula (I), $R_1$ is hydrogen or is a group selected from: $(C_1-C_6)$alkyl, $NR_7R_8$ $(C_1-C_6)$alkyl, $(C_1-C_4)$alkenyl, phenyl$(C_1-C_6)$alkyl, and a group —$(CH_2)_nCONR_5R_6$.

In a preferred embodiment, for compounds of formula (I), $R_1$ is hydrogen or is a group selected from: —$CH_2(CH_2)_nOH$, —$(CH_2)_nCONR_5R_6$, —$(CH_2)_nSO_2NR_5R_6$, and —$CH_2$—$(CH_2)_nNR_5SO_2R_6$.

In another preferred embodiment, $R_1$ is hydrogen or is a group —$(CH_2)_nCONR_5R_6$. In a still further embodiment, $R_1$ is hydrogen.

In a preferred embodiment, $R_1$ selected from the group consisting of: hydrogen, $(C_1-C_6)$alkyl, $NR_7R_8(C_1-C_6)$alkyl, $(C_1-C_4)$alkenyl, phenyl$(C_1-C_6)$alkyl wherein such phenyl ring is optionally substituted by a group $NR_{15}R_{16}(C_1-C_6)$ alkyl- or by a group —$(C_1-C_6)$alkyl$N^+R_{15}R_{16}R_{17}$, —$(CH_2)_n$ $CONR_5R_6$, —$CH_2$—$(CH_2)_nNR_5SO_2R_6$, —$(CH_2)_t$— $(C_6H_4)$—$SO_2(C_1-C_4)$alkyl, —$(CH_2)_rSO_2(C_1-C_4)$alkyl wherein such $(C_1-C_4)$alkyl is optionally substituted by a group —$NR_{15}R_{16}$ or —$N^+R_{15}R_{16}R_{17}$, —$SO_2$-phenyl wherein such phenyl ring is optionally substituted by a group —$(C_1-C_6)$alkyl $NR_7R_8$, and —$(CH_2)_nW$ wherein W is a 5-6-membered heteroaryl ring which is optionally substituted by a group —$SO_2(C_1-C_4)$alkyl.

In a preferred embodiment, $R_1$ selected from the group consisting of: hydrogen, $(C_1-C_6)$alkyl, $NR_7R_8(C_1-C_6)$alkyl, phenyl$(C_1-C_6)$alkyl wherein such phenyl ring is optionally substituted by a group $NR_{15}R_{16}(C_1-C_6)$alkyl- or by a group —$(C_1-C_6)$alkyl$N^+R_{15}R_{16}R_{17}$, —$(CH_2)_nCONR_5R_6$, —$CH_2$—$(CH_2)_nNR_5SO_2R_6$, —$(CH_2)_t$—$(C_6H_4)$—$SO_2(C_1-C_4)$alkyl, and —$(CH_2)_rSO_2(C_1-C_4)$alkyl wherein such $(C_1-C_4)$alkyl is optionally substituted by a group —$NR_{15}R_{16}$ or —$N^+R_{15}R_{16}R_{17}$.

In another preferred embodiment, $R_1$ selected from the group consisting of: hydrogen, —$(CH_2)_nCONR_5R_6$, —$CH_2$—$(CH_2)_nNR_5SO_2R_6$, and —$(CH_2)_rSO_2(C_1-C_4)$alkyl wherein such $(C_1-C_4)$alkyl is optionally substituted by a group —$NR_{15}R_{16}$ or —$N^+R_{15}R_{16}R_{17}$.

In one embodiment, a compound of formula (IA) is provided

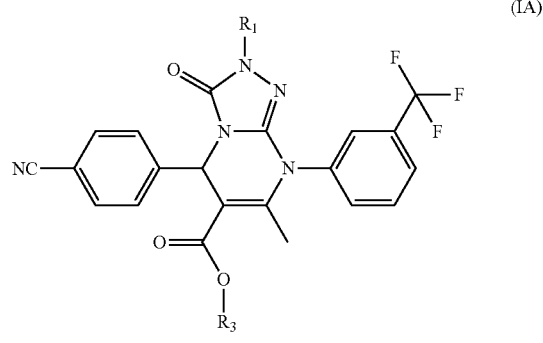

(IA)

wherein R$_{14}$ is —COXR$_3$, X is oxygen, R$_2$ is hydrogen, A is CH, and the other groups are as above defined.

In another embodiment, a compound of formula (IB) is provided

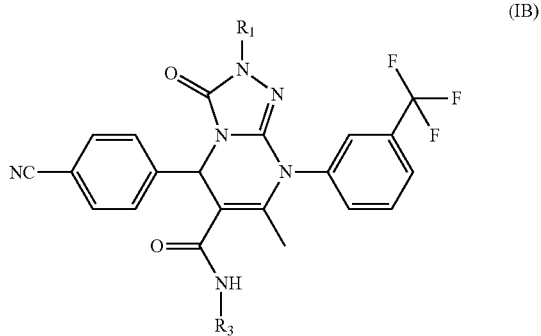

(IB)

wherein R$_{14}$ is —COXR$_3$, X is NH, R$_2$ is hydrogen, A is CH, and the other groups are as above defined.

In a further embodiment, a compound of formula (IC) is provided

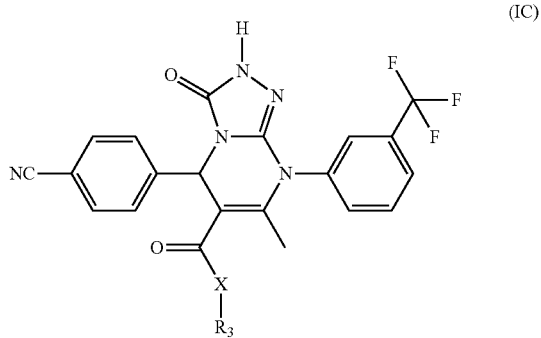

(IC)

wherein R$_{14}$ is —COXR$_3$, R$_1$ is hydrogen, R$_2$ is hydrogen, A is CH, and the other groups are as above defined.

In a further embodiment, a compound of formula (IE) is provided which is a compound of formula (I), wherein R$_{14}$ is a group —CN, R$_2$ is hydrogen, A is CH, and the other groups are as above defined.

In another embodiment, a compound of the present invention is selected in the group consisting of:
5-(4-Cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
2-Carbamoylmethyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
5-(4-Cyanophenyl)-2-(2-dimethylamino-propyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
2-Benzyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
2-Allyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid methyl ester;

and pharmaceutically acceptable salts thereof.

In still another embodiment, a compound of the present invention is selected in the group consisting of:
5-(4-Cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
2-Carbamoylmethyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
5-(4-Cyanophenyl)-2-(2-dimethylamino-propyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
2-Benzyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
2-Allyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid methyl ester;
(R)-5-(4-Cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
5-(4-Cyano-phenyl)-2-{[(2-dimethylamino-ethyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;
5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid;
5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-dimethylamino-ethyl ester;
5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-dimethylamino-propyl ester;
5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid ethylamide;
5-(4-Cyano-2-methanesulfonyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;
5-(4-Cyano-2-methanesulfonyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;
5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carbonitrile;
5-(4-Cyano-phenyl)-2-(4-methanesulfonyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;
5-(4-Cyano-phenyl)-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;
(R)-5-(4-Cyano-phenyl)-2-(4-methanesulfonyl-benzyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;
(R)-5-(4-Cyano-phenyl)-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-Cyano-phenyl)-2-(4-{[(2-dimethylamino-ethyl)-methyl-amino]-methyl}-benzenesulfonyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(4-Cyano-phenyl)-2-[2-(4-methanesulfonyl-phenyl)-ethyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-Cyano-phenyl)-2-(4-dimethylaminomethyl-benzyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

{4-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-ylmethyl]-benzyl}-trimethyl-ammonium bromide;

5-(4-Cyano-phenyl)-2-(5-methanesulfonyl-pyridin-2-ylmethyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-Cyano-phenyl)-7-methyl-3-oxo-2-[3-(2-oxo-pyrrolidin-1-yl)-propyl]-8-(3-trifluoromethyl-phenyl)-2,3,5,8-tetrahydro-[1,2,4]triazolo[4,3-a]pyrimidine-6-carboxylic acid methyl ester;

5-(4-Cyano-phenyl)-2-{[(2-dimethylamino-ethyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-Cyano-phenyl)-2-{[(3-dimethylamino-propyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

[2-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)-ethyl]-trimethyl-ammonium bromide;

[3-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)propyl]-trimethyl-ammonium bromide;

5-(4-Cyano-phenyl)-2-{[(4-dimethylamino-butyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-Cyano-phenyl)-2-{[(5-dimethylamino-pentyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

[4-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)-butyl]-trimethylammonium bromide;

[5-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)pentyl]-trimethyl-ammonium bromide;

(R)-[5-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)pentyl]-trimethyl-ammonium chloride;

2-[3-(Acetyl-methyl-amino)-propyl]-5-(4-cyano-phenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;

5-(4-Cyano-phenyl)-2-[3-(methanesulfonyl-methyl-amino)-propyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{3-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-propane-1-sulfonyl}-propyl)-trimethylammonium toluene-4-sulfonate;

(R)-(3-{3-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-propane-1-sulfonyl}-propyl)-trimethylammonium chloride;

5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carbonitrile;

(3-{3-[6-Cyano-5-(4-cyano-phenyl)-7-methyl-3-oxo-8-(3-trifluoromethyl-phenyl)-5,8-dihydro-[1,2,4]triazolo[4,3-a]pyrimidin-2-yl]-propane-1-sulfonyl}-propyl)-trimethylammonium toluene-4-sulfonate;

(R)-5-(4-Cyano-phenyl)-2-{[(5-dimethylamino-pentyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

and pharmaceutically acceptable salts thereof.

The therapeutic utility of the present compounds is pertinent to any disease that is known to be at least partially mediated by the action of human neutrophil elastase. For example, the present compounds may be beneficial in the treatment of chronic obstructive pulmonary disease (COPD), cystic fibrosis (CF), bronchiectasis, acute respiratory distress syndrome (ARDS), pulmonary emphysema, pneumonia. and lung fibrosis.

Compounds of the present invention are useful for treatment of inflammatory respiratory disorders, for example asthma (mild, moderate or severe), steroid resistant asthma, bronchitis, chronic obstructive pulmonary disease (COPD), cystic fibrosis (CF), pulmonary edema, pulmonary embolism, pneumonia, pulmonary sarcoidosis, pulmonary emphysema, silicosis, pulmonary fibrosis, pulmonary hypertension, respiratory failure, acute respiratory distress syndrome (ARDS), emphysema, chronic bronchitis, tuberculosis, aspergillosis and other fungal infections, hypersensitivity pneumonitis, vasculitic and thrombotic disorders of the lung vasculature, antitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis and lung cancer.

The present invention is also concerned with pharmaceutical formulations comprising, as an active ingredient, a compound of the invention. Other compounds may be combined with compounds of this invention for the prevention and treatment of inflammatory diseases of the lung. Thus, the present invention is also concerned with pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triamcinolone, betamethasone, fludrocoritisone, desoxycorticosterone, rofleponide, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a β2-adrenoreceptor agonist, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, BI 1744 CL, GSK159797 (milveterol), GSK59790, GSK159802, GSK642444 (vilanterol), GSK678007, GSK96108, clenbuterol, procaterol, bitolterol, LAS100977 (abediterol), BI1744CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) a expectorant/mucokinetic modulator, for example ambroxol, hypertonic solutions (e.g. saline or mannitol) or surfactant; (10) a peptide mucolytic, for example recombinant human deoxyribonuclease I (dornase-alfa and rhDNase) or helicidin; (11) antibiotics, for example azithromycin, tobramycin and aztreonam; (12) p38 Mitogen Activated Protein (MAP) kinase inhibitors, such as GSK 856553 and GSK 681323; (13) inhibitors of Janus Kinases (JAK) such as CP-690550 or GLPG0634; (14) Spleen Tyrosine Kinase (SYK) inhibitors such as R406, R343 or PRT062607; (15) inhibitors of delta and/or gamma isoforms of Phosphatidylinositol 3-kinase (PI3K); and (16) anti-retroviral agents such as ribavirin, zanamivir or laninamivir.

In one aspect, the present invention provides for the use of inhaled administration of compounds of the invention in combination with other anti-inflammatory drugs and bronchodilator drug combinations (i.e. triple combination product), including but not limited to salmeterol xinafoate/fluticasone propionate (Advair/Seretide®), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, GSK159802/GSK 685698, GSK642444/GSK 685698, formoterol fumarate/ciclesonide, and arformoterol tartrate/ciclesonide.

In another aspect, the present invention provides for the use of inhaled administration of compounds of the invention in combination with other bronchodilator drug combinations, particularly B2 agonist/M3 antagonist combinations (i.e. triple combination product), including but not limited to salmeterol xinafoate/tiotropium bromide, formoterol fumarate/tiotropium bromide, BI 1744 CL/tiotropium bromide, indacaterol/NVA237, indacaterol/QAT-370, formoterol/LAS34273, GSK159797/GSK 573719, GSK159802/GSK 573719, GSK642444/GSK 573719, GSK159797/GSK 233705, GSK159802/GSK 233705, and GSK642444/GSK 233705.

The weight ratio of the first and second active ingredients may be varied and will depend upon the effective dose of each ingredient. Generally, an effective dose of each will be used.

The magnitude of a prophylactic or therapeutic dose of a compound of the present invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

Another aspect of the present invention provides pharmaceutical compositions which comprise a compound of the invention and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the invention encompass any composition made by admixing a compound of the invention, additional active ingredient(s), and pharmaceutically acceptable excipients.

The pharmaceutical compositions of the present invention comprise a compound of the invention as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Any suitable route of administration may be employed for providing a mammal, especially a human, with an effective dosage of a compound of the present invention. In therapeutic use, the active compound may be administered by any convenient, suitable or effective route. Suitable routes of administration are known, and include oral, intravenous, rectal, parenteral, topical, ocular, nasal, buccal and pulmonary (by inhalation).

Compositions suitable for administration by inhalation are known, and may include carriers and/or diluents that are known for use in such compositions. The composition may contain 0.01-99% by weight of active compound. Preferably, a unit dose comprises the active compound in an amount of 1 µg to 10 mg.

The most suitable dosage level may be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They may be prepared by a variety of techniques, including spray-drying, freeze-drying and micronization.

By way of example, a composition of the present invention may be prepared as a suspension for delivery from a nebulizer or as an aerosol in a liquid propellant, for example for use in a pressurized metered dose inhaler (PMDI). Propellants suitable for use in a PMDI are known to the skilled person, and include CFC-12, HFA-134a, HFA-227, HCFC-22 (CCl2F2), and HFA-152 (CH4F2 and isobutane).

In a preferred embodiment of the present invention, a composition of the invention is in dry powder form, for delivery using a dry powder inhaler (DPI). Many types of DPI are known.

Microparticles for delivery by administration may be formulated with excipients that aid delivery and release. For example, in a dry powder formulation, microparticles may be formulated with large carrier particles that aid flow from the DPI into the lung. Suitable carrier particles are known, and include lactose particles; they may have a mass median aerodynamic diameter of greater than 90 μm.

In the case of an aerosol-based formulation, a preferred composition is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

Compounds of the present invention may be used in combination with other drugs that are used in the treatment/prevention/suppression or amelioration of the diseases or conditions for which present compounds are useful. Such other drugs may be administered, by a route and in an amount commonly used therefore, contemporaneously or sequentially with a compound of the invention. When a compound of the present invention is used contemporaneously with one or more other drugs, a pharmaceutical composition containing such other drugs in addition to the compound of the invention is preferred. Accordingly, the pharmaceutical compositions of the invention include those that also contain one or more other active ingredients, in addition to a compound of the present invention.

The agents of the present invention may be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321, which is incorporated herein by reference).

Methods of Synthesis.

In one aspect of the present invention, a process for the preparation of compounds of the invention (Ia), i.e. compounds of formula (I) wherein R1 is hydrogen and R14 is —COXR3, and of compounds of the invention of formula (Ib), i.e. compounds of formula (I) wherein R1 is not hydrogen and R14 is —COXR3, is provided, according to general synthetic routes reported in Scheme A here below.

Scheme A:

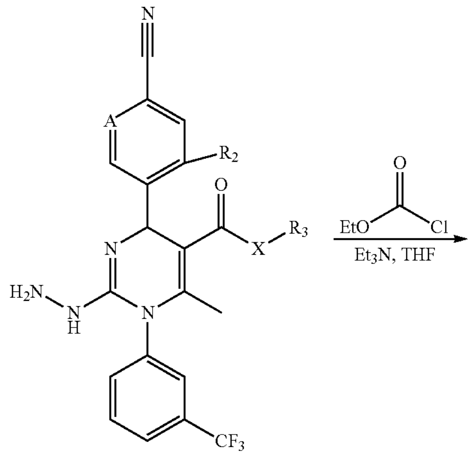

(III)

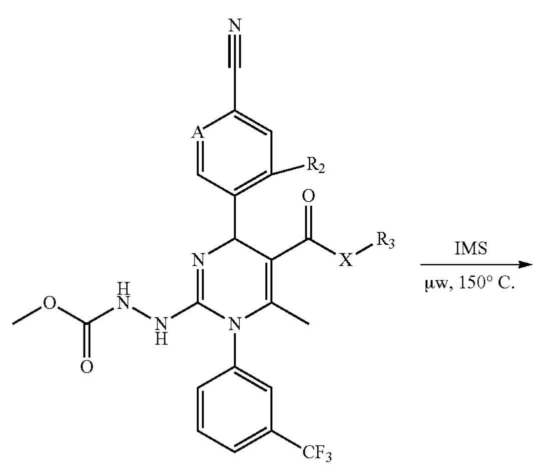

(IV)

-continued

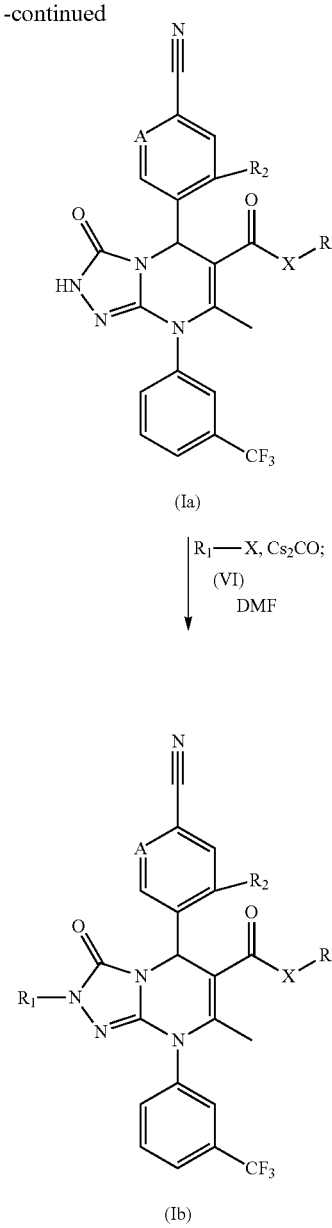

Scheme B:

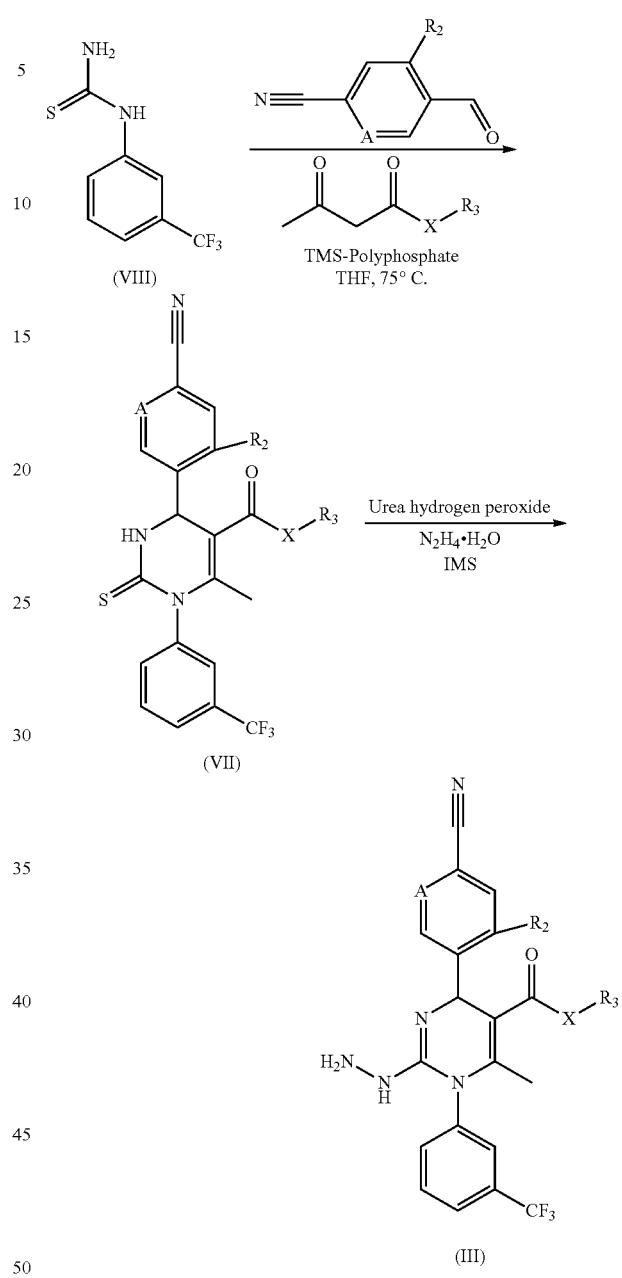

Compounds of formula (IV) may be prepared from compounds of formula (III) by reaction with ethyl chloroformate in the presence of a base such as triethylamine in a solvent such as THF at a temperature of from 0° C. to reflux. Compounds of formula (IV) may be transformed into compounds of formula (Ia) by heating in an appropriate solvent. Suitable conditions include the use of a solvent such as IMS and heating using microwave irradiation at a temperature of up to 150° C. Compounds of formula (Ia), which are compounds of formula (I) wherein $R_{14}$ is $C(O)XR_3$ and $R_1$ is H, may be converted into compounds of formula (Ib), which are compounds of formula (I) wherein $R_{14}$ is —$C(O)XR_3$, by reaction with an alkyl halide (VI) of formula $R_1$—X' such as an alkyl bromide in a solvent such as DMF in the presence of a base such as cesium carbonate at a temperature of from room temperature to 100° C.

Compounds of formula (III) wherein $R_3$ is $(C_1-C_6)$alkyl, may be prepared according to Scheme B below:

Compounds formula (VIII) may be reacted with a benzaldehyde such as 4-cyanobenzaldehyde and an acetoacetate such as ethyl acetoacetate in the presence of an acid such as TMS-polyphosphate in a solvent such as THF at a temperature of from room temperature to reflux to give compounds of formula (VII), wherein $R_3$ is $(C_1-C_6)$alkyl and the other groups are as define as for compounds of formula (I). Compounds of formula (III) may be prepared from compounds of formula (VII) by reaction with an oxidizing agent such as urea hydrogen peroxide followed by in-situ treatment with hydrazine hydrate in IMS.

The skilled person may introduce, where appropriate, suitable variations to the conditions specifically described in the experimental descriptions in order to adapt the synthetic routes to the provision of further compounds of the invention. Such variations may include, but are not limited to, the use of appropriate starting materials to generate different compounds, changes in the solvent and temperature of reactions, replacements of reagents with analogous chemicals, introduction or removal of protection/deprotection stages of functional groups sensitive to reaction conditions and reagents, as well as introduction or removal of specific synthetic steps oriented to further functionalization of the chemical scaffold.

Compounds used as starting materials or intermediates may be commercially available, their preparation may be specifically described in the literature or they may be prepared according to known methods.

The process described is particularly advantageous as it is susceptible of being properly modulated, through any proper known variant, so as to obtain any of the desired compounds. Such variants are comprised within the scope of the present invention.

From all of the above, it should be clear to the skilled person that any of the described groups may be present as such or in any properly protected form.

In particular, functional groups present in the Intermediates and Examples and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known [see, for a general reference, T. W. Green; *Protective Groups in Organic Synthesis* (Wiley, N.Y. 1981), which is incorporated herein by reference in its entirety].

Likewise, selective protection and deprotection of any of the said groups, for instance including carbonyl, hydroxyl or amino groups, may be accomplished according to well known methods.

Optional salification of the compounds of formula (I) may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

The diastereoisomers of compounds of formula (I), where available, may be obtained according to methods well known in the art, such as for example by preparative HPLC or by chromatographic purifications. A racemic mixture of compounds of formula (I) may as well be separated using preparative HPLC and a column with a chiral stationary phase, or resolved to yield individual enantiomers using methods well known in the art. Furthermore, chiral intermediates may be resolved and used to prepare chiral compounds of the invention.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

Furthermore, compounds of formula (Id), i.e. compounds of formula (I) wherein $R_{14}$ is a group —$COXR_3$ and $R_1$, $R_2$ are hydrogen and A is CH, may be prepared according to Scheme D here below reported:

Scheme C:

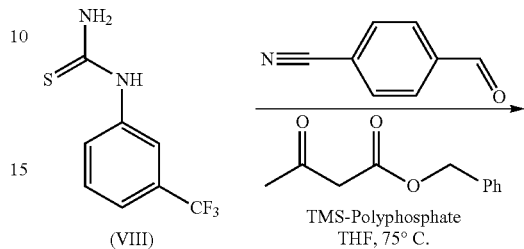

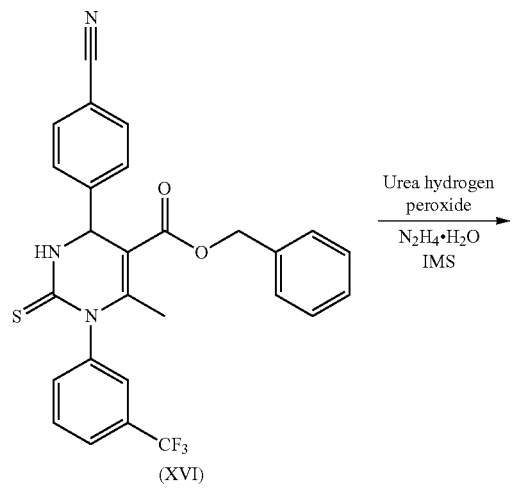

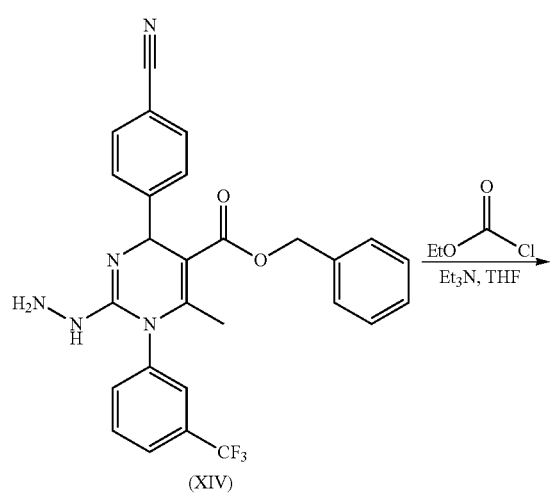

-continued

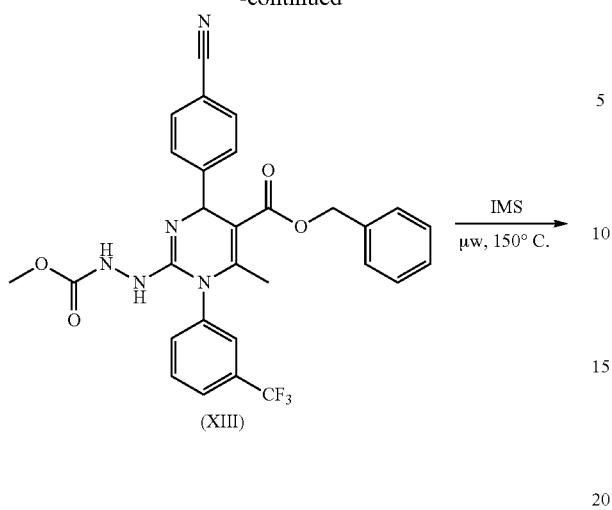

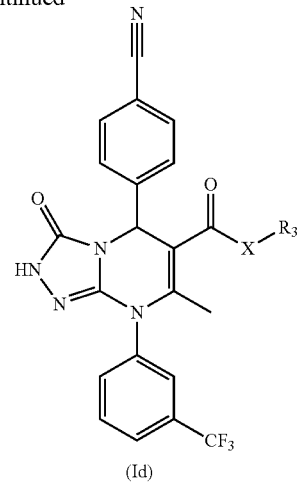

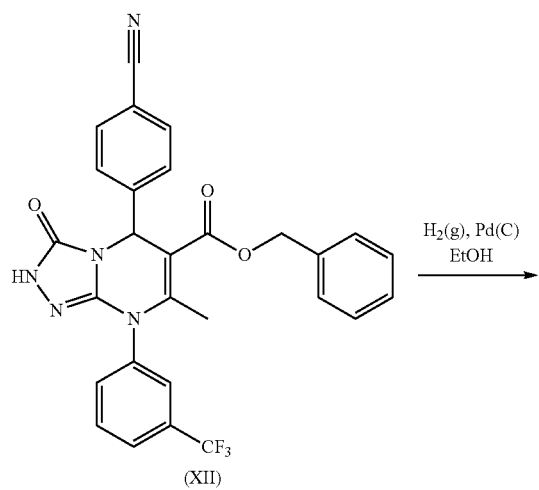

Compounds of formula (XII) can be prepared from compounds of formula (VIII) using the methods described for the synthesis of compounds (Ia) in Scheme A and Scheme B. Compounds of formula (XI) may be prepared from compounds of formula (XII) by cleavage of the benzyl ester using an appropriate method such as reduction with a catalyst such as palladium on carbon in a solvent such as IMS under an atmosphere of hydrogen. Compounds of formula (Id) may be prepared from compounds of formula (XI) by reaction with an alcohol or amine XHR$_3$ such as ammonia or 2-methoxyethanol in the presence of a coupling agent such as HATU in a solvent such as DMF in the presence of a base such as triethylamine at a temperature of from room temperature to 80° C.

The synthetic route shown in Scheme C would be of benefit in introducing XR$_3$ substituents at a late stage.

Alternatively, the acid intermediate (XI) may be prepared from compounds of formula (Ic) which are compounds of formula (I) wherein X is oxygen, R$_3$ is methyl, A, R$_2$ and R$_1$ are hydrogen, according to Scheme D below:

Scheme D:

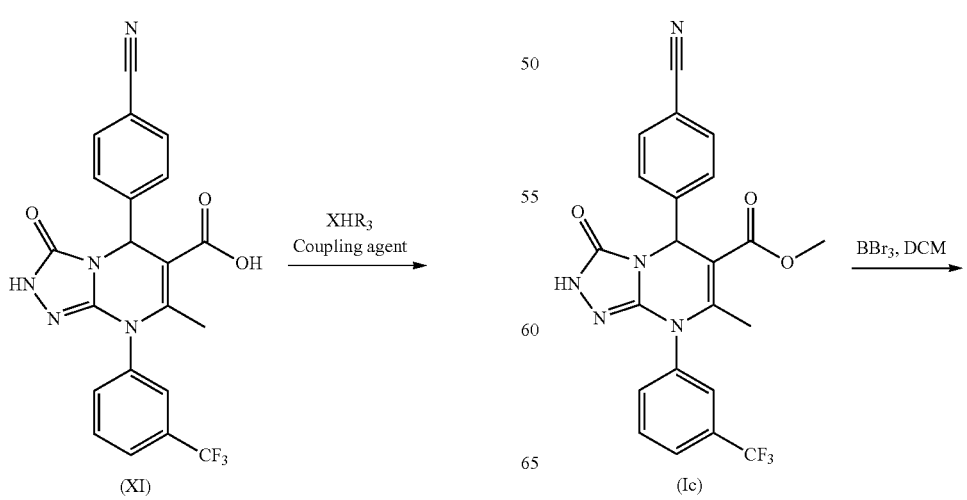

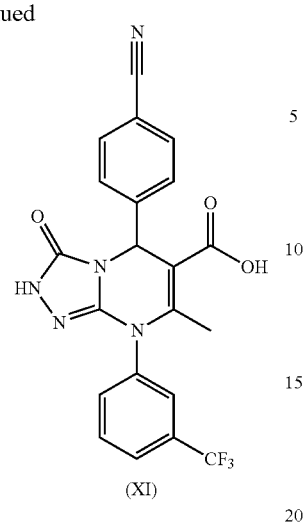

(XI)

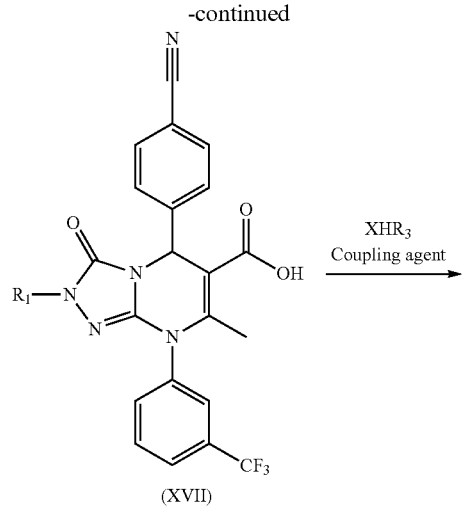

(XVII)

Treatment of a compound of formula (Ic) where $XR_3$ is OMe with a strong Lewis acid such as boron tribromide in a solvent such as DCM at a temperature of from −78° C. to room temperature followed by quenching with water or methanol can provide compounds of formula (XI).

It should be clear to the skilled person that other appropriate protecting group strategies may be contemplated and that the acid (XI) represents a versatile intermediate for further functionalization as well as compounds of formula (Id).

By way of example, according to Scheme C1, by appropriate derivatization of a compound of formula (XI), as above defined, into a compound of formula (XVII) wherein $R_1$ is not hydrogen, corresponding compounds of formula (Ih) wherein $R_1$ is not hydrogen may be obtained.

Scheme C1:

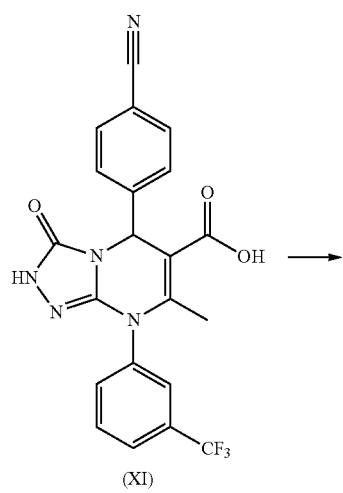

(XI)

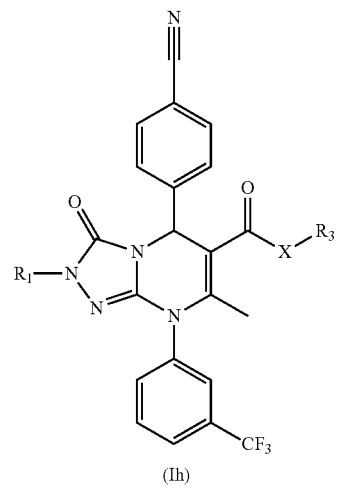

(Ih)

Compounds of formula (XVII) may be obtained from compounds of formula (XI) using the methods described for the transformation of compounds of formula (Ia) to compounds of formula (Ib) in Scheme E. Compounds of formula (Ih) may be prepared from compounds of formula (XVII) using the methods described for the conversion of compounds of formula (XI) to compounds of formula (Id) in Scheme C.

Compounds of formula (Ib) as above defined may be prepared from compounds of formula (Ia) as above defined according to alternative methods described in Scheme E below.

Scheme E:

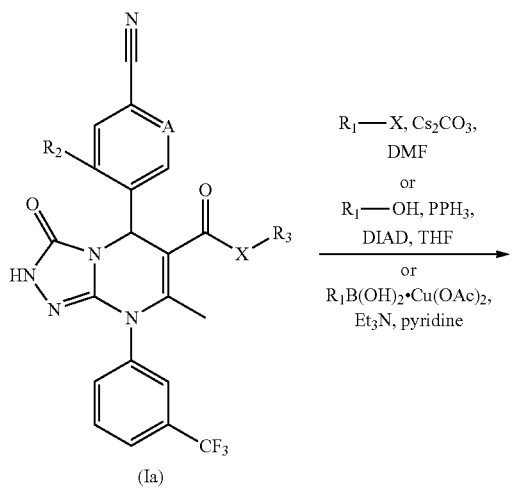

Scheme F:

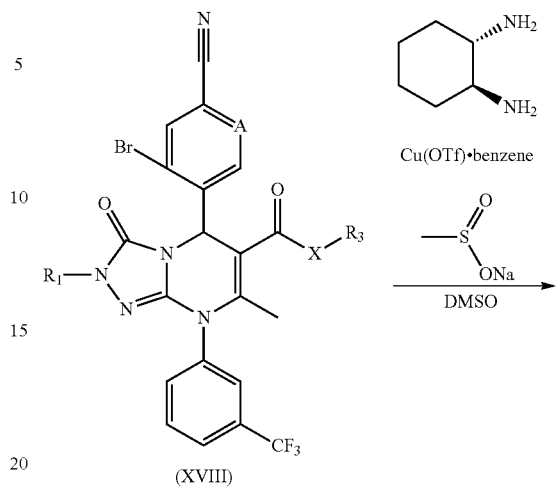

Compounds of formula (Ia) may be transformed into compounds of formula (Ib) wherein $R_1$ is an methylene-linked side-chain by reaction with an alkyl halide $R_1$—X' in the presence of a base such as cesium carbonate in a solvent such as DMF at a temperature of from room temperature to 80° C.

Alternatively, the transformation may be achieved by Mitsunobu reaction with an alcohol $R_1OH$. Typical reagents employed are triphenyl phosphine and DIAD in a solvent such as THF.

Where $R_1$=Aryl or heteroaryl a similar transformation may be achieved by the use of a Chan-Lam coupling reaction. Typical reaction conditions consist of the use of a boronic acid derivative, a copper catalyst such as copper acetate, a base such as triethylamine and a solvent such as pyridine at a temperature of from room temperature to reflux.

Compounds of formula (Ie), i.e. compounds of formula (I) wherein $R_{14}$ is a $COXR_3$ group and $R_2$ is a group —$SO_2Me$, may be prepared from compounds of formula (XVIII) according to Scheme F below:

The transformation may be achieved by reaction of an aryl bromide with sodium methane sulfinite in the presence of a catalyst such as copper triflate, a ligand such as trans-cyclohexanediamine in a solvent such as DMSO at a temperature of up to 150° C.

Scheme G:

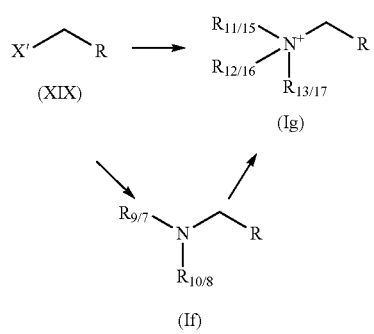

Compounds of formula (If) or (Ig), i.e. compounds of formula (I) which incorporate a group $(C_1\text{-}C_4)$alkyleneNR$_{9/7}$R$_{10/8}$ or a group $(C_1\text{-}C_4)$alkyleneN$^+$R$_{11/15}$R$_{12/16}$R$_{13/17}$ respectively as substituents, may be prepared according to Scheme G.

Compounds of formula (Ig) can be obtained directly by alkylation reaction of an appropriate tertiary amine R$_{11/15}$R$_{12/16}$R$_{13/17}$N, such as trimethylamine or dimethylpiperazine, with compounds of formula (XIX), wherein X' is an appropriate leaving group (X'=Cl, Br, I, Tosylate etc.) and group —CH$_2$R represents the portion of a compound of formula (Ig) remaining out of its substitution by a group $(C_1\text{-}C_4)$alkyleneN$^+$R$_{11/15}$R$_{12/16}$R$_{13/17}$.

Typical conditions could involve heating a tertiary amine in a solvent such as ethanol or THF at elevated temperatures of between 60° C. and 150° C., using microwave irradiation.

Alternatively, the transformation of compounds of formula (XIX) to compounds of formula (Ig) may be achieved via the tertiary amine (If) where R$_{9/7}$ and R$_{10/8}$≠H. Tertiary amine compounds of formula (Ig) may be prepared from compounds of formula (XIX) by reaction with a secondary amine R$_{9/7}$R$_{10/8}$NH. Typical reaction conditions include the use of a base such as cesium carbonate or potassium carbonate in a solvent such as DMF at RT. The conversion of compounds of formula (If), where R$_{9/7}$ and R$_{10/8}$ H, to compounds of formula (Ig) can be obtained using methylating agents such as methyl bromide, methyl iodide or methyl benzenesulfonate. Typical reaction conditions consist of the use of a solvent such as MeCN or acetone at a temperature of between RT to 60° C. under conventional or microwave heating.

Furthermore, primary and secondary amine compounds of formula (If) may also be prepared from compounds of formula (XIX) by reaction with ammonia or a suitable primary amine R$_{9/7}$NH$_2$, respectively to give a primary amine or secondary amine.

Scheme H:

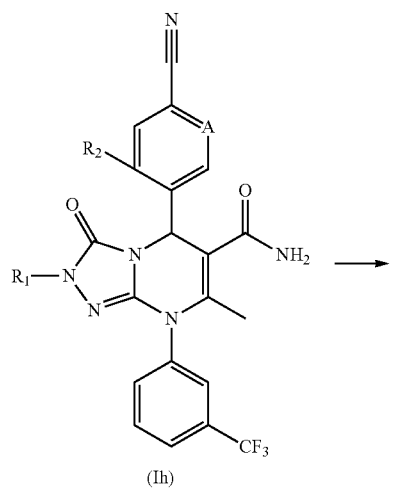

(Ih)

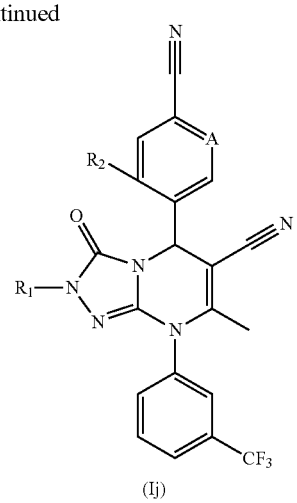

(Ij)

Compounds of formula (Ij), i.e. compounds of formula (I) wherein R$_{14}$ is a group —CN, may be prepared according to Scheme H from compounds of formula (Ih), which are compounds of formula (I) wherein XR$_3$ is NH$_2$, by reaction with a dehydrating agent such as Burgess reagent in a solvent such as THF at a temperature of from room temperature to reflux.

Other features of the invention will become apparent in the course of the following descriptions of exemplary embodiments which are given for illustration of the invention and are not intended to be limiting thereof.

EXAMPLES

General Experimental Details

Reactions were not carried out under an inert atmosphere unless specified. Where products were purified using an Isolute® SPE Si II cartridge, 'Isolute SPE Si cartridge' refers to a pre-packed polypropylene column containing unbonded activated silica with irregular particles with average size of 50 μm and nominal 60 Å porosity. Where an Isolute® SCX-2 cartridge was used, 'Isolute® SCX-2 cartridge' refers to a pre-packed polypropylene column containing a non end-capped propylsulphonic acid functionalized silica strong cation exchange sorbent. 'Isolute® PE-AX cartridge' refers to a pre-packed polypropylene column containing a silica-based sorbent with a chemically bonded quaternary ammonium functional group. All solvents and commercial reagents were used as received.

$^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, td=triplet of doublets, q=quartet, m=multiplet.

Microwave experiments were carried out using a Biotage Initiator 60™ which uses a single-mode resonator and dynamic field tuning. Temperature from 40-250° C. can be achieved, and pressures of up to 30 bar can be reached.

Compound names were generated using the Autonom 2000 feature in MDL ISIS™/Draw 2.5 SP2 software.

Preparative HPLC Conditions.

HPLC System 1.

C18-reverse-phase end-capped column (250×21.2 mm Gemini column with 5 μm particle size), eluting with a gradient of A: water; B: acetonitrile (0.1% formic acid added) with a flow rate typically 18 mL/min and gradient of 1%/min increasing in B. UV detection at 254 nm.

HPLC System 2.

C18-reverse-phase end-capped column (250×21.2 mm Gemini column with 5 μm particle size), eluting with a gradient of A: water; B: methanol (0.1% formic acid added) with a flow rate typically 13 mL/min and gradient of 1%/min increasing in B. UV detection at 254 nm.

Analytical LC-MS Conditions.

LC-MS Method 1.

Waters Platform LC with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV

MS ionisation method—Electrospray (positive and negative ion)

LC-MS Method 2.

Waters Micromass ZMD with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow mL/min | % A | % B |
|---|---|---|---|
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection—MS, ELS, UV (100 μl split to MS with in-line UV detector)

MS ionisation method—Electrospray (positive and negative ion)

LC-MS Method 3.

Waters Micromass ZQ2000 with a C18-reverse-phase column (100×2.1 mm Acquity BEH with 1.7 μm particle size) maintained at 40° C., elution with A: water+0.1% formic acid; B: acetonitrile+0.1% formic acid. Gradient:

| Gradient-Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection—MS, UV PDA

MS ionisation method—Electrospray (positive/negative ion)

LC-MS Method 4.

HP1100 with a C18-reverse-phase column (30×4.6 mm Phenomenex Luna 3 μm particle size), elution with A: water+0.1% formic acid; B: acetonitrile+0.1% formic acid. Gradient:

| Gradient-Time | flow mL/min | % A | % B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection—MS, ELS, UV (200 μl split to MS with in-line UV detector)

MS ionisation method—Electrospray (positive and negative ion)

MDAP System:

Instrumentation: Agilent 1260 infinity purifications system. Agilent 6100 series single Quadrupole LC/MS Column: XSEELECT CSH Prep C18 5 μm OBD, 30×150 mm, RT Mobile Phase A: 0.1% aqueous formic acid Mobile Phase B: 0.1% formic acid in acetonitrile Flow: 60 ml/min Gradient Program: 10%-95%, 22 min, centred around a specific focused gradient Sample Injection of a 20-60 mg/ml solution in DMSO (+optional formic acid and water).

Abbreviations Used in the Experimental Section:

$BBr_3$ Boron tribromide
$CH_3CN$ Acetonitrile
DCM Dichloromethane
DIAD Di-isopropyl azodicarboxylate
DIPEA Di-isopropylethylamine
DMF N,N-Dimethylformamide
DMSO Dimethyl sulfoxide
$Et_3N$ Triethylamine
EtOAC Ethyl acetate
HATU O-(7-Azabenzotriazol-1-yl)-N,N,N',N'-tetramethyluronium hexafluorophosphate
HCl Hydrochloric acid
IMS Industrial methylated spirits
LC-MS Liquid chromatography-mass spectrometry
mCPBA 3-Chloroperbenzoic acid
MDAP Mass-directed automated HPLC purification
MeOH Methanol
mins Minutes
mL Milliliter
Mmol Millimol
$N_2$ Nitrogen
$Na_2SO_4$ Sodium sulfate
$Na_2S_2O_3$ Sodium thiosulphate
RT Room temperature
Rt Retention time
TBAF Tetrabutylammonium fluoride
THF Tetrahydrofuran In the procedures that follow, some of the starting materials are identified through an "Intermediate" or "Example" number. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Intermediate 1. 4-(4-Cyanophenyl)-6-methyl-2-thioxo-1-(3-trifluoromethylphenyl)-1,2,3,4-tetrahydro-pyrimidine-5-carboxylic acid methyl ester

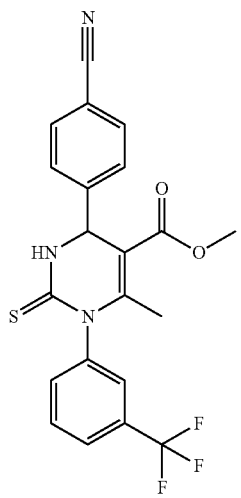 [SMILES: COC(=O)C1=C(C)N(c2cccc(C(F)(F)F)c2)C(=S)NC1c1ccc(C#N)cc1]

To a solution of 3-trifluoromethylphenylthiourea (2.2 g, 10 mmol) 4-cyanobenzaldehyde (1.4 g, 11 mmol) and methyl acetoacetate (1.2 mL, 11 mmol) in THF (40 mL) was added trimethylsilylphosphate (1.8 g) and the mixture heated at 70° C. After 17 hours, the reaction mixture was allowed to cool, then poured onto 0.5 M HCl (200 mL) and extracted into EtOAc. The organic phase was washed with water, then brine, dried (Na$_2$SO$_4$) and concentrated in vacuo. The resulting residue was purified by silica gel chromatography eluting with a gradient of 20-30% EtOAc in cyclohexane Appropriate fractions were combined and concentrated in vacuo to yield the title compound as a white foam (3.7 g).

LC-MS (Method 1): Rt=3.88 min, m/z=432 [M+H]$^+$

Intermediate 2. 4-(4-Cyanophenyl)-2-hydrazino-6-methyl-1-(3-trifluoromethyl-phenyl)-1,4-dihydro-pyrimidine-5-carboxylic acid methyl ester

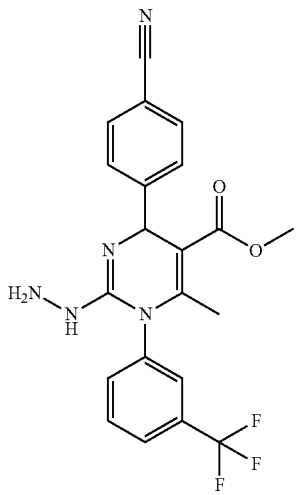 [SMILES: COC(=O)C1=C(C)N(c2cccc(C(F)(F)F)c2)C(NN)=NC1c1ccc(C#N)cc1]

To a solution of intermediate 1 (2 g, 4.6 mmol) in IMS (100 mL) was added urea hydrogen peroxide (865 mg, 9.2 mmol) and the mixture was stirred for 5 hours at RT before addition of hydrazine hydrate (891 μL, 18.4 mmol). The reaction mixture was stirred for a further 16 hours at RT and then the solvent reduced to a low volume in vacuo. The resultant residue was partitioned between EtOAc and saturated aqueous Na$_2$S$_2$O$_3$. The organic layer was separated, washed with brine, dried (Na$_2$SO$_4$) and evaporated in vacuo. The resulting residue was purified by silica gel chromatography eluting with 80% EtOAc in cyclohexane. Appropriate fractions were combined and concentrated in vacuo to yield the title compound as a yellow oil (729 mg).

LC-MS (Method 2): Rt=2.38 min, m/z=430 [M+H]$^+$

Intermediate 3. 4-(4-Cyanophenyl)-2-(N'-methoxycarbonyl-hydrazino)-6-methyl-1-(3-trifluoromethylphenyl)-1,4-dihydro-pyrimidine-5-carboxylic acid methyl ester

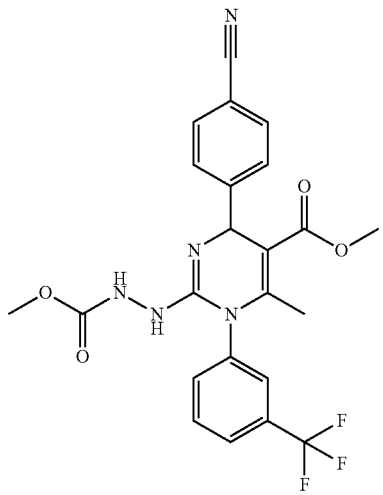

Intermediate 2 (724 mg, 1.7 mmol) was dissolved in THF (20 mL) and cooled to 0° C. before addition of triethylamine (362 μl, 2.6 mmol) and ethyl chloroformate (191 μL, 2 mmol). The reaction mixture was stirred at 0° C. for 1 hour and then partitioned between EtOAc and water. The organic layer was separated, washed with brine, dried (Na$_2$SO$_4$) and evaporated in vacuo. The resultant residue was triturated with EtOAc, filtered and the solid collected to yield the title compound as a white solid (49 mg).

LC-MS (Method 2): Rt=2.47 min, m/z=502 [M+H]$^+$

Intermediate 4. 4-(4-Cyanophenyl)-2-methoxy-6-methyl-1,4-dihydropyrimidine-5-carboxylic acid methyl ester

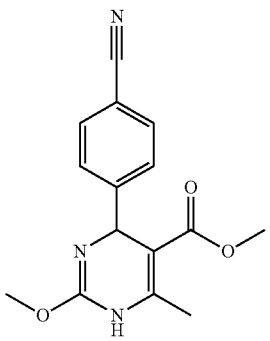

To a solution of 4-cyanobenzaldehyde (13.1 g, 100 mmol) in DMF (200 mL), was added sodium bicarbonate (33.4 g, 400 mmol), followed by O-methylisourea hemisulphate (14.8 g, 120 mmol) and methyl acetoacetate (12.8 g, 110 mmol). The reaction mixture was heated at 70° C. for 5 hours, then poured into water and the product was extracted into EtOAc. The organic phase was washed with water (×2) followed by brine then dried ($Na_2SO_4$) and evaporated to dryness. The resulting yellow gum was purified by silica gel chromatography eluting with diethyl ether to give the title compound as a yellow solid (12.8 g).

LC-MS (Method 1): Rt=2.20 min, m/z=286 [M+H]$^+$

Intermediate 5. 6-(4-Cyanophenyl)-2-methoxy-4-methyl-6H-pyrimidine-1,5-dicarboxylic acid 5-methyl ester 1-(4-nitrophenyl)ester

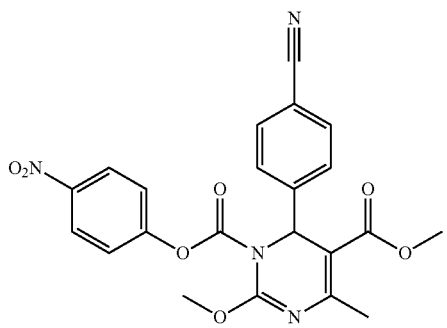 [SMILES: COC(=O)C1=C(C)N=C(OC)N(C(=O)Oc2ccc([N+](=O)[O-])cc2)C1c1ccc(C#N)cc1]

Intermediate 4 (1.56 g, 5.46 mmol) was dissolved in a mixture of DCM (25 mL) and pyridine (10 mL) and cooled using an ice bath. A solution of 4-nitrophenyl chloroformate (705 mg, 3.50 mmol) in DCM (25 mL) was added over 30 minutes. The reaction mixture was stirred for 1 hour at 0° C. and then the solvent was removed in vacuo. The resulting residue was purified by silica gel chromatography eluting with a gradient of 0-20% EtOAc in cyclohexane to gave the title compound as a yellow solid. The product thus obtained was used in the subsequent step without further analysis (2.0 g).

Intermediate 6. 2-Benzyl-5-(4-cyanophenyl)-7-methyl-3-oxo-2,3,5,8-tetrahydro-[1,2,4]triazolo[4,3-a]pyrimidine-6-carboxylic acid methyl ester

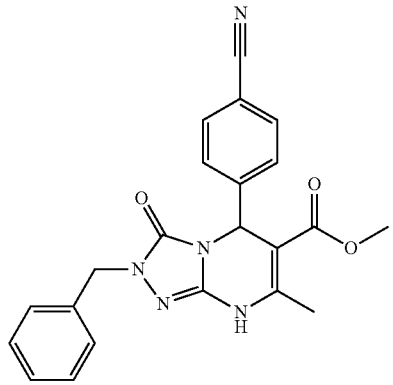 [SMILES: COC(=O)C1=C(C)Nc2nn(Cc3ccccc3)c(=O)n2C1c1ccc(C#N)cc1]

Intermediate 5 (250 mg, 0.55 mmol) and benzyl hydrazine hydrochloride (120 mg, 0.61 mmol) were suspended in $CH_3CN$ (10 mL) at 0° C., and $Et_3N$ (85 µl, 0.61 mmol) was added. The reaction mixture was stirred at 0° C. for 30 mins and then allowed to reach RT and stirred for a further 1 hour. The reaction mixture was filtered and the filtrate was concentrated in vacuo. The resulting residue was purified by silica gel chromatography eluting with a gradient of 0-100% to yield the title compound as a yellow solid (100 mg).

LC-MS (Method 2): Rt=3.87 min, m/z=402 [M+H]$^+$

Intermediate 7. 2-Allyl-5-(4-cyanophenyl)-7-methyl-3-oxo-2,3,5,8-tetrahydro-[1,2,4]triazolo[4,3-a]pyrimidine-6-carboxylic acid methyl ester

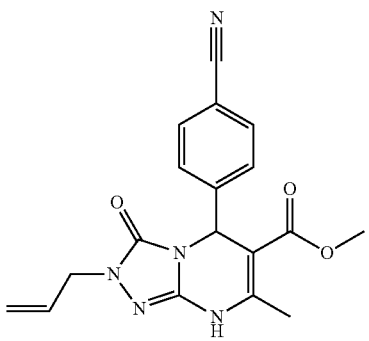 [SMILES: C=CCn1nc2n(c1=O)C(c1ccc(C#N)cc1)C(C(=O)OC)=C(C)N2]

Intermediate 4 (1.42 g, 5 mmol) was dissolved in a mixture of DCM (10 mL) and pyridine (10 mL) and cooled using an ice bath. A solution of 4-nitrophenyl chloroformate (0.955 mg, 4.75 mmol) in DCM (10 mL) was added dropwise, and the resulting solution was stirred at 0° C. for 1.5 hours, and then a solution of allyl hydrazine hydrochloride (1.0 g, 5.5 mmol) and DIPEA (3.75 mL, 22 mmol) in $CH_3CN$ (10 mL) was added in one portion. The resulting mixture was allowed to warm to RT, stirred for 4 hours, and then partitioned between EtOAc and water. The organic layer was separated, washed with water, followed by brine, then dried ($Na_2SO_4$) and evaporated in vacuo to yield the title compound as a yellow oil (0.95 g).

LC-MS (Method 2): Rt=2.73 min, m/z=352 [M+H]$^+$

Intermediate 8. 5-(4-Cyanophenyl)-2,7-dimethyl-3-oxo-2,3,5,8-tetrahydro-[1,2,4]triazolo[4,3-a]pyrimidine-6-carboxylic acid methyl ester

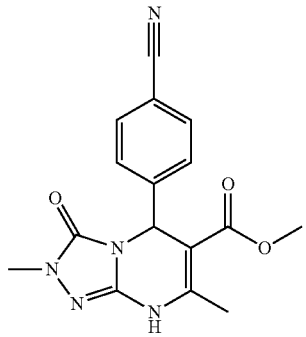

Intermediate 8 was prepared using an analogous method to that described above for Intermediate 7.

LC-MS (Method 2): Rt=2.46 min, m/z=326 [M+H]$^+$

Intermediate 9. (R)-4-(4-Cyanophenyl)-6-methyl-2-thioxo-1-(3-trifluoromethylphenyl)-1,2,3,4-tetrahydro-pyrimidine-5-carboxylic acid methyl ester

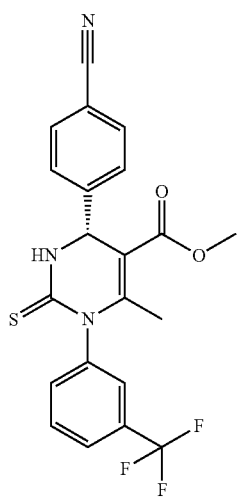 [SMILES: COC(=O)C1=C(C)N(c2cccc(C(F)(F)F)c2)C(=S)N[C@@H]1c1ccc(C#N)cc1]

To a solution of (R)-4-(4-cyano-phenyl)-6-methyl-2-oxo-1-(3-trifluoromethyl-phenyl)-1,2,3,4-tetrahydro-pyrimidine-5-carboxylic acid methyl ester (14.5 g, 35 mmol) (prepared according to WO 2006/082412, which is incorporated herein by reference in its entirety) in toluene (105 mL) under an atmosphere of N$_2$, was added Lawesson's reagent (17 g, 42 mmol), and the resulting mixture stirred at 120° C. for 17 hours. The reaction mixture was allowed to cool to RT and then evaporated in vacuo. The resulting residue was dissolved in diethyl ether, filtered, and the filtrate collected, washed with brine, dried (Na$_2$SO$_4$) and evaporated in vacuo. The resulting residue was purified by silica gel chromatography eluting with a gradient of 10-40% EtOAc in cyclohexane to yield the title compound as a yellow foam (4.8 g).

LC-MS (Method 2): Rt=3.75 min, m/z=432 [M+H]$^+$

Intermediate 10. (R)-4-(4-Cyanophenyl)-2-hydrazino-6-methyl-1-(3-trifluoromethylphenyl)-1,4-dihydro-pyrimidine-5-carboxylic acid methyl ester

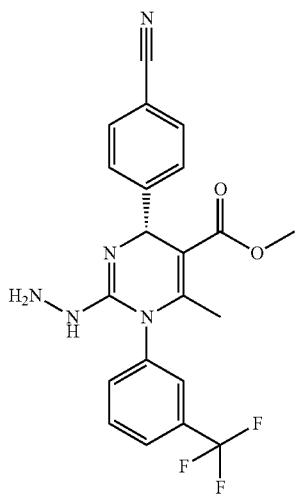 [SMILES: COC(=O)C1=C(C)N(c2cccc(C(F)(F)F)c2)C(NN)=N[C@@H]1c1ccc(C#N)cc1]

Intermediate 10 (593 mg) was prepared from Intermediate 9 (3.39, 7.9 mmol) according to an analogous procedure to that described for Intermediate 2.

LC-MS (Method 1): Rt=2.57 min, m/z=430 [M+H]$^+$

Intermediate 11. (R)-4-(4-Cyanophenyl)-2-(N'-methoxycarbonyl-hydrazino)-6-methyl-1-(3-trifluoromethylphenyl)-1,4-dihydro-pyrimidine-5-carboxylic acid methyl ester

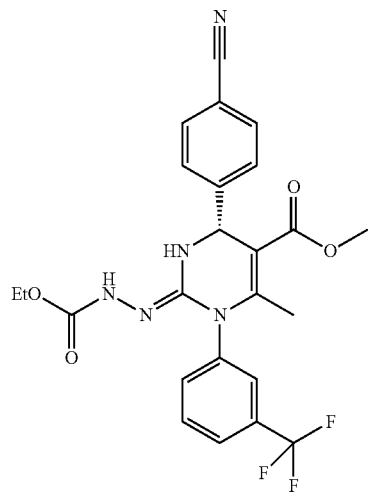 [SMILES: CCOC(=O)N/N=C1\N[C@H](c2ccc(C#N)cc2)C(C(=O)OC)=C(C)N1c1cccc(C(F)(F)F)c1]

Intermediate 11 (381 mg) was prepared from Intermediate 10 (782 mg, 1.8 mmol) according to an analogous procedure to that described for Intermediate 3.

LC-MS (Method 1): Rt=2.60 min, m/z=502 [M+H]$^+$

Intermediate 12. 5-(2-Bromo-4-cyano-phenyl)-7-methyl-3-oxo-8-(3-trifluoromethyl-phenyl)2,3,5,8-tetrahydro-[1,2,4]triazolo[4,3-a]pyrimidine-6-carboxylic acid methyl ester

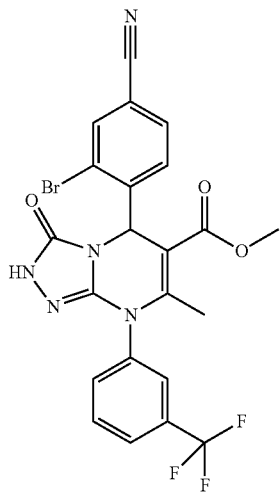 [SMILES: COC(=O)C1=C(C)N(c2cccc(C(F)(F)F)c2)c2n[nH]c(=O)n2C1c1ccc(C#N)cc1Br]

Intermediate 12 (2.58 g) was prepared according to analogous procedures to those described for Intermediates 1, 2, and 3 and Example 1, using 2-bromo-4-cyanobenzaldehyde (12 g, 57 mmol) in place of 4-cyanobenzaldehyde as starting material of the synthetic sequence.

LC-MS (Method 3): Rt=4.65 min, m/z=534 [M($^{79}$Br)+H]$^+$
$^1$H NMR (400 MHz, DMSO) δ 11.20 (1H, s), 8.18 (1H, d, J=1.6 Hz), 8/09 91H, br s), 7.93-7.75 (5H, m), 6.23 (1H, d, J=1.2 Hz), 3.49 (3H, s), 2.13 (3H, s).

Intermediate 13. 5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid amide

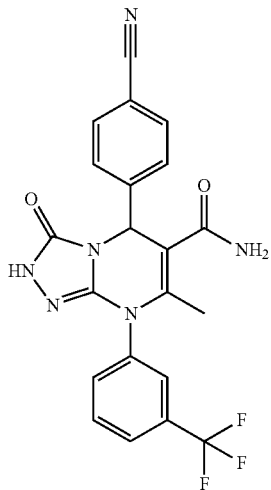 [SMILES: CC1=C(C(N)=O)C(c2ccc(C#N)cc2)n2c(n[nH]c2=O)N1c1cccc(C(F)(F)F)c1]

Example 9 (160 mg, 0.36 mmol) was dissolved in DMF (5 mL) and then diiosopropylethylamine (123 µL, 0.72 mmol) was added followed by HATU (280 mg, 0.72 mmol). After 1 hour, ammonia (0.5 M in dioxane, 4.3 mL, 2.15 mmol) was added, and the mixture stirred at 60° C. for 16 hours. The mixture was allowed to cool to RT, then partitioned between EtOAc and water. The organic layer was separated, and the aqueous layer extracted with EtOAc. The combined organic layers were washed with brine, dried (Na$_2$SO$_4$) and evaporated in vacuo. The resulting residue was purified by silica gel chromatography eluting with a gradient of 0-10% MeOH in DCM to yield the title compound as a white solid (120 mg).

LC-MS (Method 3): Rt=3.47 min, m/z=440 [M+H]$^+$

Intermediate 14. 1-Bromo-3-methanesulfonyl-propane

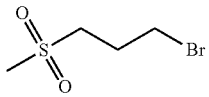

To a solution of 3-(methylsulfonyl)-1-propanol (276 mg, 2 mmol) in DCM (10 mL), was added carbon tetrabromide (730 mg, 2.2 mmol) followed by portion-wise addition of triphenylphosphine (580 mg, 2.2 mmol) under an atmosphere of N$_2$. The resulting solution was stirred at RT for 17 hours. The reaction mixture was partitioned between DCM and water. The organic layer was separated, washed with brine, dried (Na$_2$SO$_4$) and evaporated in vacuo. The resulting residue was purified by silica gel chromatography using eluting with 50% EtOAc in cyclohexane to give the title compound as a colourless oil (297 mg).

$^1$H NMR (400 MHz, DMSO) δ 3.63 (2H, t J=7 Hz), 3.25-3.20 (2H, m), 3.01 (3H, s), 2.27-2.19 (2H, m)

Intermediate 15. 2-(4-Bromomethyl-benzyl)-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

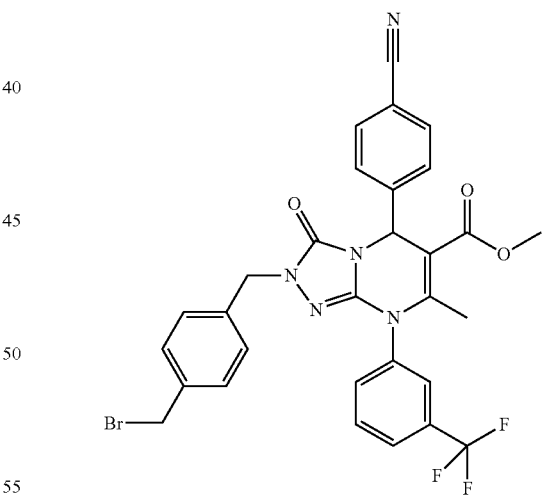

Example 1 (228 mg, 0.5 mmol) was dissolved in DMF (5 mL), and cesium carbonate (652 mg, 2 mmol) and α,α'-dibromo-p-xylene (396 mg, 1.5 mmol) were added. The reaction mixture was stirred at RT for 1 hour and was then partitioned between EtOAc and water. The organic layer was separated, washed with brine, dried (Na$_2$SO$_4$) and evaporated in vacuo. The resulting residue was purified by silica gel chromatography eluting with 40% EtOAc in cyclohexane as eluent to give the title compound as a white solid (211 mg).

LC-MS (Method 4): Rt=4.11 min, m/z 638 [M($^{79}$Br)+H]$^+$

Intermediate 16. 5-(4-Cyano-phenyl)-2-methoxycarbonylmethyl-7-methyl-3-oxo-8-(3-trifluoromethyl-phenyl)-2,3,5,8-tetrahydro-[1,2,4]triazolo[4,3-a]pyrimidine-6-carboxylic acid methyl ester

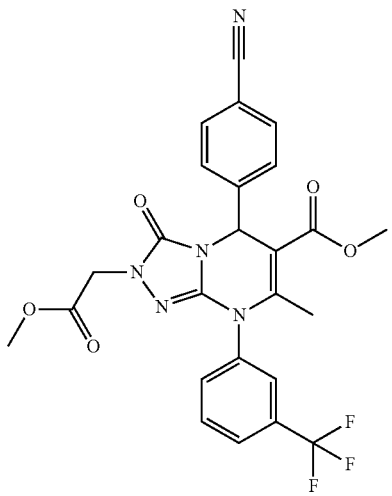

Example 1 (108 mg, 0.24 mmol) was dissolved in DMF (2 mL), and cesium carbonate (94 mg, 0.29 mmol) and methyl bromoacetate (24 µL, 0.26 mmol) were added. The reaction mixture was stirred at RT for 2 hours and then partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with a gradient of 0-30% EtOAc in DCM and to yield the title compound as a white solid (112 mg).

LC-MS (Method 2): Rt=3.59 min, m/z=528 [M+H]$^+$

Intermediate 17. 2-Carboxymethyl-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

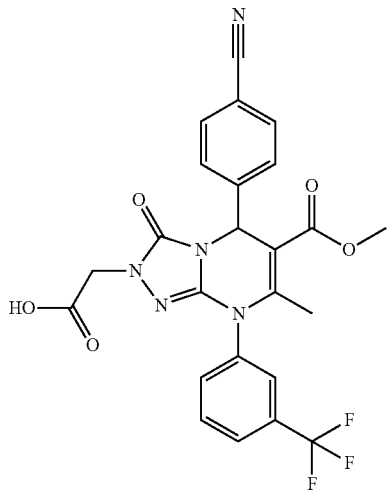 [SMILES: COC(=O)C1=C(C)N(c2cccc(C(F)(F)F)c2)c2nn(CC(=O)O)c(=O)n2C1c1ccc(C#N)cc1]

To a solution of Intermediate 16 (108 mg, 0.21 mmol) in THF (1 mL), was added MeOH (1 mL) followed by lithium hydroxide (3 M in water, 68 µL, 0.21 mmol). The reaction mixture was stirred at RT for 2 hours, and then lithium hyroxide (3 M in water, 27 µL, 0.08 mmol) was added. After a further 1 hour stirring at RT, the reaction mixture was made acidic by addition of 1 M HCl and extracted with EtOAc. The combined organic layers were washed with brine, dried (Na$_2$SO$_4$) and evaporated in vacuo to yield the title compound as a white solid (100 mg).

LC-MS (Method 2): Rt=3.33 min, m/z=514 [M+H]$^+$

Intermediate 18. 2-[3-(tert-Butoxycarbonyl-methyl-amino)-propyl]-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

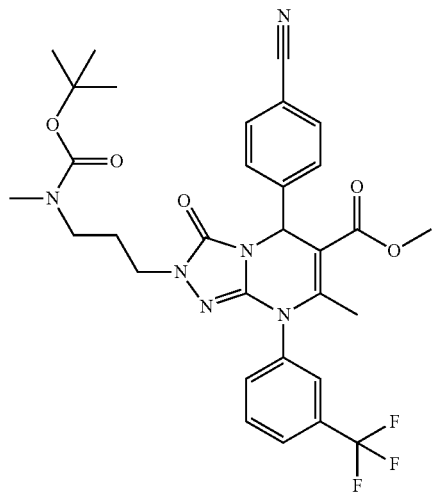

Example 1 (0.2 g, 0.44 mmol) was dissolved in DMF (4 mL), and cesium carbonate (0.19 g, 0.53 mmol) was added, followed by (3-iodo-propyl)-methyl-carbamic acid tert-butyl ester (0.14 g, 0.48 mmol). The reaction mixture was stirred at RT for 18 hours and then quenched with water and extracted with EtOAc. The combined organic layers were washed with brine, dried (Na$_2$SO$_4$) and evaporated in vacuo. The resulting residue was purified by silica gel chromatography eluting with a gradient of 0-5% MeOH in DCM to yield the title compound as a white solid (238 mg).

LC-MS (Method 2): Rt=4.02 min, m/z=627 [M+H]$^+$

Intermediate 19. 3-[3-(tert-Butyl-dimethyl-silanyloxy)-propylsulfanyl]-propan-1-ol

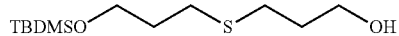 [SMILES: CC(C)(C)[Si](C)(C)OCCCSCCCO]

A solution of 3,3'-thiodipropanol (900 mg, 6 mmol) in THF (3 ml) was added dropwise to a suspension of sodium hydride (240 mg, 6 mmol) in THF (15 ml) under an atmosphere of N$_2$. The reaction mixture was stirred at RT for 30 mins, then a solution of tert-butyldimethylsilylchloride (900 mg, 6 mmol) in THF (2 ml) was added and stirring was continued for 16 hours. The reaction mixture was partitioned between EtOAc and water. The organic layer was separated, washed with brine, dried (Na$_2$SO$_4$) and evaporated in vacuo. The resulting residue was purified by silica gel chromatography eluting with 20% EtOAc in cyclohexane to give the title compound as a colourless oil (793 mg).

¹H NMR (400 MHz, DMSO) 4.44-4.30 (1H, m), 3.71-3.63 (2H, m), 3.52-3.43 (2H, m), 3.29-3.18 (4H, m), 1.76-1.63 (4H, m), 0.89 (9H, s), 0.06 (6H, s).

Intermediate 20. 3-[3-(tert-Butyl-dimethyl-silanyloxy)-propane-1-sulfonyl]-propan-1-ol

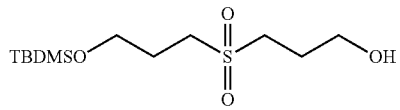 [SMILES: CC(C)(C)[Si](C)(C)OCCCS(=O)(=O)CCCO]

Intermediate 19 (782 mg, 2.96 mmol) was dissolved in DCM (25 ml), and mCPBA (1.55 g, 9 mmol) was added. The reaction mixture was stirred at RT for 2 hours and then partitioned between DCM and saturated aqueous $Na_2S_2O_5$. The organic layer was separated, washed with saturated aqueous $NaHCO_3$, then brine, dried ($Na_2SO_4$) and evaporated in vacuo to yield the title compound as a white solid (919 mg).

¹H NMR (400 MHz, DMSO) δ 4.69 (1H, s), 3.73-3.66 (2H, m), 3.53-3.48 (2H, m), 3.16-3.08 (4H, m), 1.91-1.78 (4H, m), 0.89 ((H, s), 0.07 (6H, s).

Intermediate 21. 2-{3-[3-(tert-Butyl-dimethyl-silanyloxy)-propane-1-sulfonyl]-propyl}-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

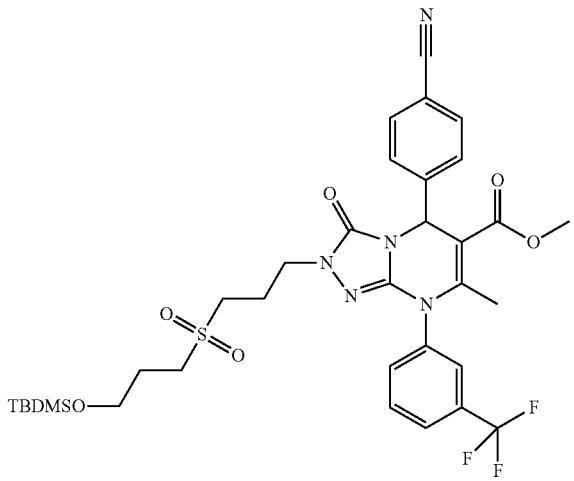 [SMILES: COC(=O)C1=C(C)N(c2cccc(C(F)(F)F)c2)c2nn(CCCS(=O)(=O)CCCO[Si](C)(C)C(C)(C)C)c(=O)n2C1c1ccc(C#N)cc1]

Example 1 (228 mg, 0.5 mmol) was dissolved in THF (5 mL), and then Intermediate 20 (178 mg, 0.6 mmol) and triphenylphosphine (158 mg, 0.6 mmol) were added followed by dropwise addition of a solution of diisopropyl azodicarboxylate (118 μL, 0.6 mmol) in THF (1 ml). The reaction mixture was stirred at RT for 5 hours and then partitioned between EtOAc and water. The organic layer was separated, and the aqueous layer further extracted with EtOAc. The combined organic layers were washed with brine, dried ($Na_2SO_4$) and evaporated in vacuo. The resulting residue was purified by silica gel chromatography eluting with 50% EtOAc in cyclohexane to afford the title compound (282 mg).

LC-MS (Method 2): Rt=4.49 min, m/z=734 [M+H]⁺

Intermediate 22. 5-(4-Cyano-phenyl)-2-[3-(3-hydroxy-propane-1-sulfonyl)-propyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

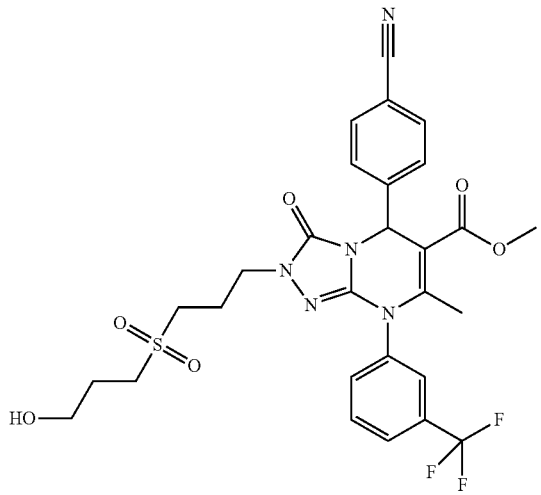 [SMILES: COC(=O)C1=C(C)N(c2cccc(C(F)(F)F)c2)c2nn(CCCS(=O)(=O)CCCO)c(=O)n2C1c1ccc(C#N)cc1]

Intermediate 21 (282 mg, 0.38 mmol) was dissolved in THF (3 mL), and then a solution of 1 M TBAF in THF (760 μl, 0.76 mmol) was added. The reaction mixture was stirred at RT for 4 hours and then partitioned between EtOAc and water. The organic layer was separated, and the aqueous layer further extracted with EtOAc. The combined organic layers were washed with brine, dried ($Na_2SO_4$) and evaporated in vacuo. The resulting residue was purified by silica gel chromatography eluting with a gradient of 0-2% methanol in EtOAc to afford the title compound (89 mg).

LC-MS (Method 2): Rt=3.29 min, m/z=620 [M+H]⁺

Intermediate 23. 5-(4-Cyano-phenyl)-7-methyl-3-oxo-2-{3-[3-(toluene-4-sulfonyloxy)-propane-1-sulfonyl]-propyl}-8-(3-trifluoromethyl-phenyl)-2,3,5,8-tetrahydro-[1,2,4]triazolo[4,3-a]pyrimidine-6-carboxylic acid methyl ester

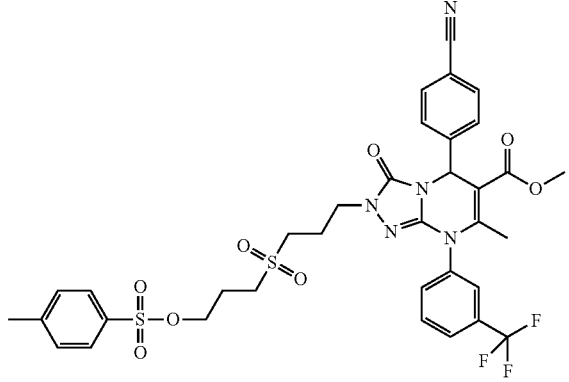

Intermediate 22 (89 mg, 0.14 mmol) was dissolved in THF (3 ml), and then sodium hydride (6 mg, 0.2 mmol) was added under an atmosphere of $N_2$. The reaction mixture was stirred at RT for 10 mins, then toluenesulfonyl chloride (31 mg, 0.16 mmol) was added and stirring was continued for 16 hours. The reaction mixture was partitioned between EtOAc and water. The organic layer was separated, washed with brine, dried (Na$_2$SO$_4$) and evaporated in vacuo. The resulting residue was purified by silica gel chromatography eluing with a gradient of 50-80% EtOAc in cyclohexane to yield the title compound as a colourless oil (70 mg).

LC-MS (Method 4): Rt=3.81 min, m/z=774 [M+H]$^+$

Intermediate 24. [3-(3-Bromo-propane-1-sulfonyl)-propoxy]-tert-butyl-dimethyl-silane

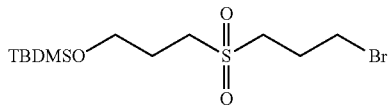 [SMILES: CC(C)(C)[Si](C)(C)OCCCS(=O)(=O)CCCBr]

Intermediate 24 (485 mg) was prepared from Intermediate 20 (1.18 g, 4 mmol)) according to an analogous procedure to that described for Intermediate 14.

$^1$H NMR (400 MHz, DMSO) 3.68 (2H, t, J=6 Hz), 3.63 (2H, t, J=6 Hz), 3.25-3.21 (2H, m), 3.16-3.11 (2H, m), 2.26-2.17 (2H, m), 1.90-1.82 (2H, m), 0.87 (9H, s), 0.05 (6H, s).

Intermediate 25. (R)-5-(4-Cyano-phenyl)-2-methoxycarbonylmethyl-7-methyl-3-oxo-8-(3-trifluoromethyl-phenyl)-2,3,5,8-tetrahydro-[1,2,4]triazolo[4,3-a]pyrimidine-6-carboxylic acid methyl ester

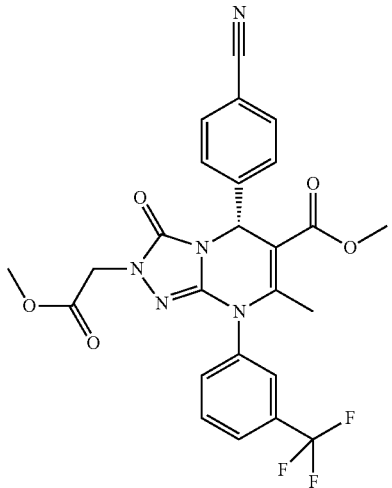

Example 7 (227 mg, 0.5 mmol) was dissolved in DMF (4 mL), and cesium carbonate (195 mg, 0.6 mmol) and methyl bromoacetate (51 µL, 0.55 mmol) were added. The reaction mixture was stirred at RT for 18 hours and then partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with 50% EtOAc in cyclohexane to yield the title compound as a colourless glass (244 mg).

LC-MS (Method 4): Rt=3.16 min, m/z=528 [M+H]$^+$

Intermediate 26. (R)-2-Carboxymethyl-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

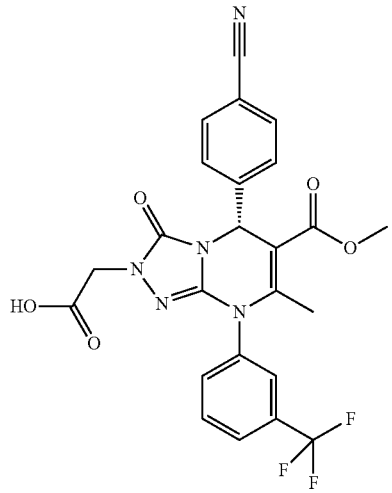 [SMILES: COC(=O)C1=C(C)N(c2cccc(C(F)(F)F)c2)c2nn(CC(=O)O)c(=O)n2[C@@H]1c1ccc(C#N)cc1]

To a solution of Intermediate 25 (240 mg, 0.46 mmol) in THF (3 mL), was added MeOH (3 mL) followed by lithium hydroxide (3M in water, 200 µL, 0.6 mmol). The reaction mixture was stirred at RT for 2 hours, and then the volatiles were removed in vacuo. The resultant residue was dissolved in water, and the solution thus obtained was made acidic by addition of 6 N HCl and extracted with EtOAc. The combined organic layers were washed with brine, dried (Na$_2$SO$_4$) and evaporated in vacuo to yield the title compound as a colourless oil (250 mg).

LC-MS (Method 4): Rt=2.88 min, m/z=514 [M+H]$^+$

Intermediate 27. (R)-2-{3-[3-(tert-Butyl-dimethyl-silanyloxy)-propane-1-sulfonyl]-propyl}-5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

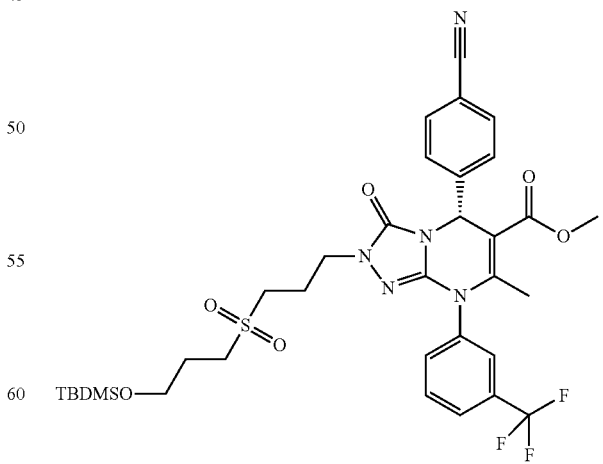

Example 7 (455 mg, 1 mmol) was dissolved in DMF (5 mL), and cesium carbonate (489 mg, 1.5 mmol) and a solution of Intermediate 24 (481 mg, 1.3 mmol) were added. The reaction mixture was stirred at RT for 16 hours and then partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with 50% EtOAc in cyclohexane to yield the title compound as an off-white foam (623 mg).

LC-MS (Method 2): Rt=7.33 min, m/z=734 [M+H]$^+$

Intermediate 28. (R)-5-(4-Cyano-phenyl)-2-[3-(3-hydroxy-propane-1-sulfonyl)-propyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

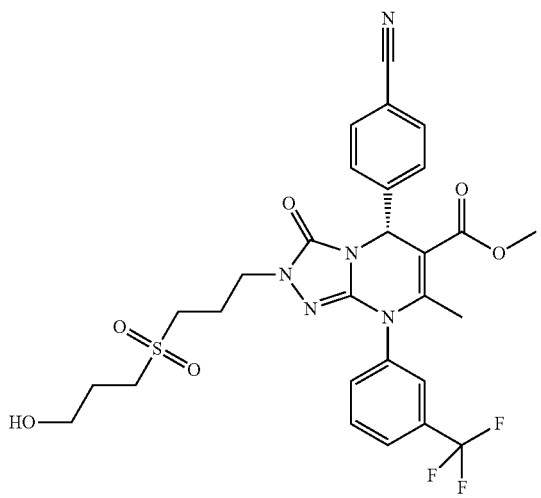 [SMILES: COC(=O)C1=C(C)N(c2cccc(C(F)(F)F)c2)c2nn(CCCS(=O)(=O)CCCO)c(=O)n2[C@@H]1c1ccc(C#N)cc1]

Intermediate 27 (620 mg, 0.85 mmol) was dissolved in THF (7 mL), and then a solution of 1 M TBAF in THF (1.3 ml, 1.3 mmol) was added. The reaction mixture was stirred at RT for 16 hours and then partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with a gradient of 4-5% methanol in DCM to afford the title compound as a colourless oil (476 mg).

LC-MS (Method 4): Rt=2.83 min, m/z=620 [M+H]$^+$

Intermediate 29. (R)-5-(4-Cyano-phenyl)-7-methyl-3-oxo-2-{3-[3-(toluene-4-sulfonyloxy)-propane-1-sulfonyl]-propyl}-8-(3-trifluoromethyl-phenyl)-2,3,5,8-tetrahydro-[1,2,4]triazolo[4,3-a]pyrimidine-6-carboxylic acid methyl ester

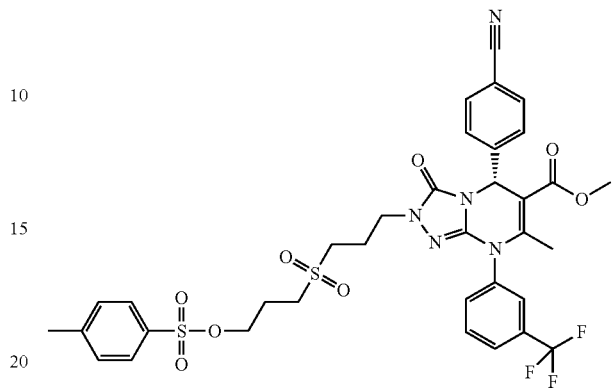

Intermediate 28 (470 mg, 0.76 mmol) was dissolved in THF (5 ml), and then sodium hydride (48 mg, 1.2 mmol) was added under an atmosphere of N$_2$. The reaction mixture was stirred at RT for 10 mins, then toluenesulfonyl chloride (191 mg, 1 mmol) was added and stirring was continued for 16 hours. The reaction mixture was partitioned between EtOAc and water. The organic layer was separated, washed with brine, dried (Na$_2$SO$_4$) and evaporated in vacuo. The resulting residue was purified by silica gel chromatography eluting with a gradient of 50-80% EtOAc in cyclohexane to give the title compound as a pale yellow glass (132 mg).

LC-MS (Method 4): Rt=3.43 min, m/z=774 [M+H]$^+$

Example 1

5-(4-Cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester

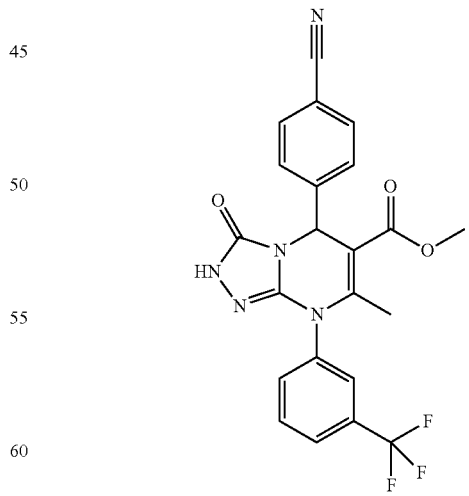

Intermediate 3 (400 mg, 0.8 mmol) was dissolved in IMS (12 mL) and heated at 150° C. for 1 hour using microwave irradiation. The solvent was removed in vacuo, and the resulting residue was purified by silica gel chromatography eluing with a gradient of 50-70% EtOAc in cyclohexane to yield the title compound as a white solid (185 mg).

LC-MS (Method 2): Rt=3.32 min, m/z=456 [M+H]+

¹H NMR (400 MHz, DMSO) δ 11.25 (1H, s), 8.09 (1H, s), 7.93-7.78 (5H, m), 7.67 (2H, d, J=8 Hz), 5.92 (1H, s), 3.55 (3H, s) and 2.16 (3H, s).

Example 2

2-Carbamoylmethyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester

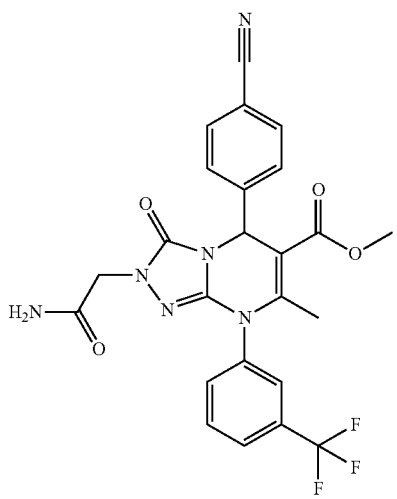 [SMILES: COC(=O)C1=C(C)N(c2cccc(C(F)(F)F)c2)c2nn(CC(N)=O)c(=O)n2C1c1ccc(C#N)cc1]

Example 1 (85 mg, 0.19 mmol) was dissolved in DMF (3 mL), and cesium carbonate (94 mg, 0.29 mmol) and 2-iodoacetamide (41 mg, 0.22 mmol) were added. The reaction mixture was stirred at RT for 3 hours and then partitioned between EtOAc and water. The organic layer was separated, washed with brine, dried (Na₂SO₄) and evaporated in vacuo. The resulting residue was purified by silica gel chromatography eluting with EtOAc to give the title compound as a pale yellow solid (49 mg).

LC-MS (Method 3): Rt=4.14 min, m/z=513 [M+H]+

¹H NMR (400 MHz, DMSO) δ 8.08 (1H, s), 7.93-7.79 (5H, m), 7.70 (2H, d, J=8 Hz), 7.26 (1H, s), 7.12 (1H, s), 5.96 (1H, s), 4.07 (1H, d, J=17 Hz), 3.98 (1H, d, J=17 Hz), 3.56 (3H, s), and 2.15 (3H, s).

Example 3

5-(4-Cyanophenyl)-2-(2-dimethylamino-propyl)-7-methyl-3-oxo-8-(3-trifluoromethylphenyl)-2,3,5,8-tetrahydro-[1,2,4]triazolo[4,3-a]pyrimidine-6-carboxylic acid methyl ester

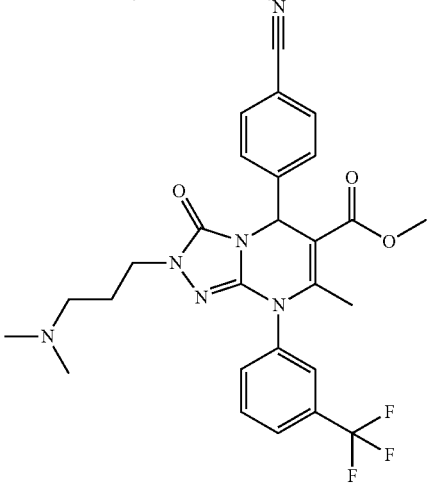

Example 1 (85 mg, 0.19 mmol) was dissolved in DMF (3 mL), and cesium carbonate (156 mg, 0.48 mmol) and 3-dimethylamin-1-propylchloride hydrochloride (35 mg, 0.22 mmol) were added. The reaction mixture was stirred at RT for 16 hours and then heated at 65° C. for 3 hours. The reaction mixture was allowed to cool and then partitioned between EtOAc and water. The organic layer was separated, washed with brine, dried (Na₂SO₄) and evaporated in vacuo. The resulting residue was purified by silica gel chromatography eluting with a gradient of 4-10% MeOH in DCM to yield the title compound as an off-white solid (23 mg).

LC-MS (Method 3): Rt=3.53 min, m/z=541 [M+H]+

¹H NMR (400 MHz, DMSO) δ 8.10 (1H, s), 7.94-7.79 (5H, m), 7.67 (2H, d, J=8 Hz), 5.95 (1H, s), 3.55 (3H, s), 3.52-3.39 (2H, m), 2.15 (3H, s), 2.03 (2H, td, J=2 and 7 Hz), 1.98 (6H, s) and 1.57-146 (2H, m).

Example 4

2-Benzyl-5-(4-cyanophenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

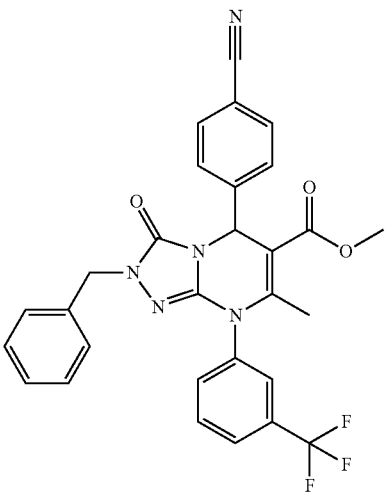 [SMILES: COC(=O)C1=C(C)N(c2cccc(C(F)(F)F)c2)c2nn(Cc3ccccc3)c(=O)n2C1c1ccc(C#N)cc1]

Intermediate 6 (100 mg, 0.24 mmol), 3-trifluoromethylphenylboronic acid (95 mg, 0.5 mmol), Et₃N (250 μl, 1.8 mmol), and copper (II) acetate (50 mg, 0.4 mmol) were dissolved in DCM (10 mL), and stirring at RT was continued for 48 hours. The reaction mixture was filtered to remove the solid and the filtrate was concentrated in vacuo. The resulting residue was purified by silica gel chromatography eluting with a gradient of 0-15% MeOH in DCM. Appropriate fractions were combined and concentrated in vacuo and the resulting residue further purified using preparative HPLC system 2 to yield the title compound as a white solid (20 mg).

LC-MS (Method 3): Rt=5.43 min, m/z=546 [M+H]+

$^1$H NMR (400 MHz, CDCl$_3$) δ 7.77 (1H, d, J=8 Hz), 7.70-7.65 (3H, m) 7.59-7.54 (3H, m), 7.51 (1H, d, J=8 Hz), 7.29-7.24 (3H, m), 7.22-7.18 (2H, m), 6.14 (1H, s), 4.80 (1H, d, J=15 Hz), 4.60 (1H, d, J=15 Hz), 3.64 (3H, s) and 2.25 (3H, s).

Example 5

2-Allyl-5-(4-cyanophenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

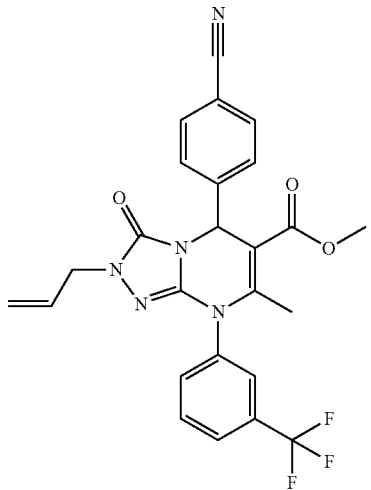 [SMILES: C=CCn1nc2n(c1=O)C(c1ccc(C#N)cc1)C(C(=O)OC)=C(C)N2c1cccc(C(F)(F)F)c1]

Example 5 was prepared from Intermediate 7 using an analogous method to that described above for Example 4 to yield the title compound as a white powder.

LC-MS (Method 3): Rt=4.10 min, m/z=496 [M+H]+

$^1$H NMR (400 MHz, DMSO) δ 8.11 (1H, s), 7.94-7.89 (2H, m), 7.88-7.79 (3H, m), 7.69 (2H, d, J=8 Hz), 5.96 (1H, s), 5.72-5.62 (1H, m), 5.04 (1H, dd, J=1 and 10 Hz), 4.95 (1H, dd, J=1 and 16 Hz), 4.14-4.04 (2H, m), 3.55 (3H, s) and 2.14 (3H, s).

Example 6

5-(4-Cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid methyl ester

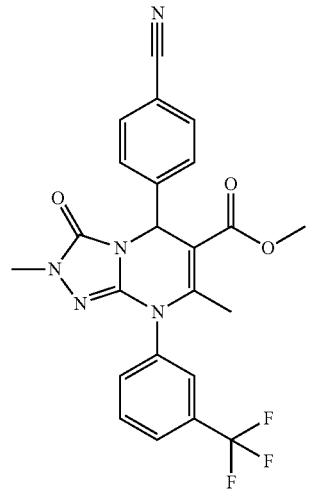

Intermediate 8 (900 mg, 2.77 mmol), 3-trifluoromethylphenylboronic acid (1.05 g, 5.54 mmol), Et$_3$N (925 μl, 6.6 mmol), and copper (II) acetate (1.0 g, 5.54 mmol) were dissolved in DCE (25 mL), and the reaction mixture was stirred at 80° C. for 18 hours. After cooling to RT the reaction mixture was partitioned between DCM and water. The organic layer was separated, washed with water, followed by brine, then dried (MgSO$_4$) and evaporated in vacuo. The resulting residue was purified by silica gel chromatography eluting with a gradient of 3-10% MeOH in DCM and then using HPLC system 1 to yield the title compound as an orange solid (47 mg).

LC-MS (Method 3): Rt=4.80 min, m/z=470 [M+H]+

$^1$H NMR (400 MHz, DMSO) δ 8.11 (1H, s), 7.91 (2H, t, J=8 Hz), 7.87-7.79 (3H, m), 7.69 (2H, d, J=8 Hz), 5.94 (1H, s), 3.55 (3H, s), 3.08 (3H, s) and 2.15 (3H, s).

Example 7

(R)-5-(4-Cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester

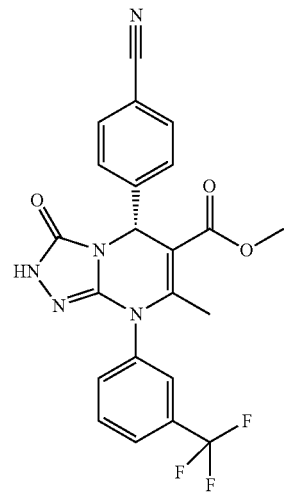 [SMILES: COC(=O)C1=C(C)N(c2cccc(C(F)(F)F)c2)c2n[nH]c(=O)n2[C@@H]1c1ccc(C#N)cc1]

Example 7 (112 mg) was prepared from Intermediate 11 (376 mg) according to an analogous procedure to that described for Example 1.

Alternatively, Example 7 could be made from Example 1 by submitting Example 1 to preparative HPLC chromatography on a chiral phase [Daicel Chiralpak IC column (5 μm, 250 mm×10 mm, 3% IPA/DCM eluent, 5 ml/min flow rate, 220 nm detection)]. Example 1 (3.15 g) was dissolved in 3% IPA/DCM (60 ml) and run with 60 injections of 1 ml to give the (R) enantiomer (2nd eluting enantiomer) (1.5 g).

LC-MS (Method 3): Rt=4.42 min, m/z=456 [M+H]+

¹H NMR (400 MHz, DMSO) δ 11.25 (1H, s), 8.09 (1H, s), 7.93-7.78 (5H, m), 7.67 (2H, d, J=8 Hz), 5.92 (1H, s), 3.55 (3H, s) and 2.16 (3H, s).

Example 8

5-(4-Cyano-phenyl)-2-{[(2-dimethylamino-ethyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester

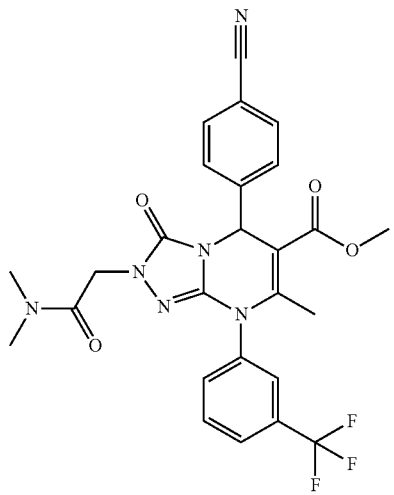

Example 1 (60 mg, 0.13 mmol) was dissolved in DMF (1 mL), and cesium carbonate (51 mg, 0.16 mmol) and 2-chloro-N,N-dimethylacetamide (15 μl, 0.15 mmol) were added. The reaction mixture was stirred at RT for 16 hours and then partitioned between EtOAc and water. The organic layer was separated, and the aqueous layer further extracted with EtOAc. The combined organic layers were washed with brine, dried (Na₂SO₄) and evaporated in vacuo. The resulting residue was purified by silica gel chromatography eluting with 50% EtOAc in DCM to give the title compound as a white solid (56 mg).

LC-MS (Method 3): Rt=4.45 min, m/z=549 [M+H]+

¹H NMR (400 MHz, DMSO) δ 8.04 (1H, s), 7.87-7.74 (5H, m), 7.64 (2H, d, J=9 Hz), 5.93 (1H, s), 4.36 (2H, s), 3.52 (3H, s), 2.80 (3H, s), 2.68 (3H, s), 2.15 (3H, s).

Example 9

5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid

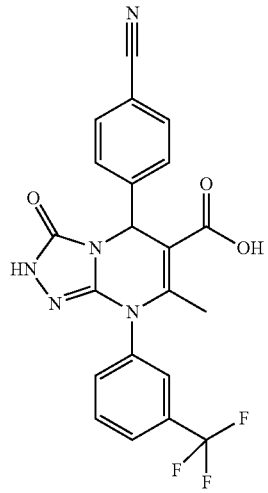 [SMILES: CC1=C(C(=O)O)C(c2ccc(C#N)cc2)n2c(n[nH]c2=O)N1c1cccc(C(F)(F)F)c1]

Example 1 (100 mg, 0.22 mmol) was dissolved in DCM (2 mL) under an atmosphere of N₂ and cooled to −78° C. before the dropwise addition of BBr₃ (1M in DCM, 1 mL, 1 mmol). The reaction mixture was stirred at −78° C. for 1 hour, before warming to 0° C. and stirring for a further 4 hours. The reaction mixture was cautiously quenched with saturated aqueous NaHCO₃ and then diluted with DCM. The aqueous layer was separated, acidified to pH 1 by addition of 6 N HCl and then extracted with DCM. The combined extracts were concentrated in vacuo to yield the title compound as a white solid (53 mg).

LC-MS (Method 3): Rt=3.81 min, m/z=442 [M+H]+

¹H NMR (400 MHz, DMSO) δ 12.49 (1H, br s), 11.22 (1H, s), 8.08 (1H, s), 7.92-7.77 (5H, m), 7.66 (2H, d, J=8 Hz), 5.90 (1H, s), 2.17 (3H, s).

Example 10

5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-dimethylamino-ethyl ester

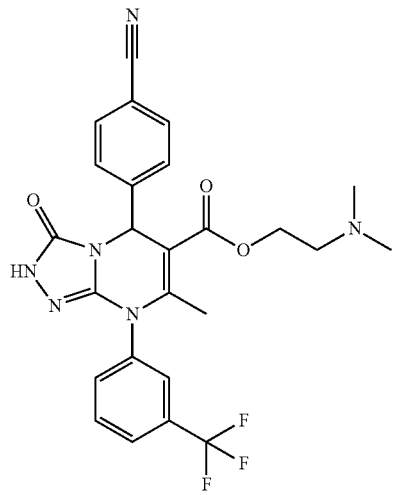 [SMILES: CC1=C(C(=O)OCCN(C)C)C(c2ccc(C#N)cc2)n2c(n[nH]c2=O)N1c1cccc(C(F)(F)F)c1]

To a solution of Example 9 (32 mg, 0.073 mmol) in DMF (1 mL), was added diiosopropylethylamine (125 μL, 0.73 mmol) followed by HATU (30 mg, 0.080 mmol). After 1 hour, N,N-dimethylethanolamine (73 µL, 0.73 mmol) was added, and the reaction mixture was stirred at RT for 16 hours. The reaction mixture was partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by reverse phase HPLC using a gradient 20-70% acetonitrile in water with 0.1% ammonia to yield the title compound as a white solid (4 mg).

LC-MS (Method 3): Rt=3.14 min, m/z=513 [M+H]$^+$ $^1$H NMR (400 MHz, CDCl$_3$) δ 8.39 (1H, br s), 7.77 (1H, d, J=8 Hz), 7.71-7.53 (7H, m), 6.11 (1H, s), 4.20-4.06 (2H, m), 2.49-2.47 (2H, m), 2.26 (3H, s), 2.21 (6H, s).

$^1$H NMR (400 MHz, CDCl$_3$) δ 9.22 (1H, br s), 7.76 (1H, d, J=7 Hz), 7.69-7.61 (3H, m), 7.58-7.51 (4H, m), 6.08 (1H, s), 4.04 (2H, t, J=6), 2.25 (3H, s), 2.21 (6H, s), 2.11-2.07 (2H, m), 1.67-1.60 (2H, m).

Example 12

5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid ethylamide Example 11

5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-dimethylamino-propyl ester

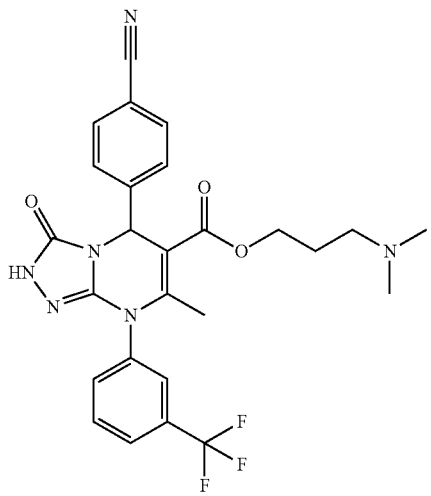 [SMILES: CC1=C(C(=O)OCCCN(C)C)C(c2ccc(C#N)cc2)n2c(n[nH]c2=O)N1c1cccc(C(F)(F)F)c1]

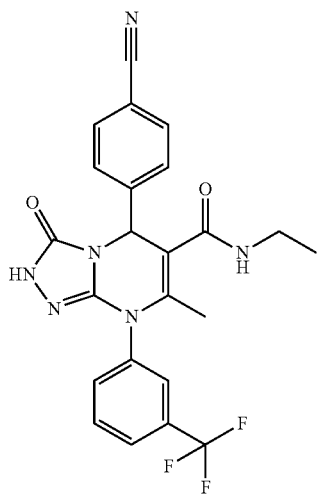 [SMILES: CCNC(=O)C1=C(C)N(c2cccc(C(F)(F)F)c2)c2n[nH]c(=O)n2C1c1ccc(C#N)cc1]

To a solution of Example 9 (42 mg, 0.095 mmol) in DMF (1 mL), was added diiosopropylethylamine (33 µL, 0.19 mmol) followed by HATU (72 mg, 0.19 mmol). After 1 hour, N,N-dimethylpropanolamine (67 µL, 0.57 mmol) was added, and the reaction mixture was stirred at 60° C. for 16 hours. The reaction mixture was allowed to cool to RT then partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with a gradient of 0-6% (2 M NH$_3$ in MeOH) in DCM to give the title compound as a white solid (15 mg).

LC-MS (Method 3): Rt=3.18 min, m/z=527 [M+H]$^+$

To a solution of Example 9 (100 mg, 0.23 mmol) in DMF (3 ml), were added DIPEA (102 µl, 0.6 mmol) and HATU (133 mg, 0.35 mmol) and the reaction mixture was stirred at RT for 45 mins. Ethylamine (2 M in THF, 175 µL, 0.35 mmol) was then added, and stirring at RT was continued for 16 hours. Further ethylamine (2 M in THF, 175 µL, 0.35 mmol) was added, the temperature was raised to 60° C., and stirring was continued for 1.5 hours. The reaction mixture was partitioned between EtOAc and water. The organic layer was separated, washed with brine, dried (Na$_2$SO$_4$) and evaporated in vacuo. The resulting residue was purified by silica gel chromatography eluting with a gradient of 80-100% EtOAc in cyclohexane to yield the title compound as a white solid (53 mg).

LC-MS (Method 3): Rt=3.84 min, m/z=469 [M+H]$^+$ $^1$H NMR (400 MHz, DMSO) δ 11.12 (1H, s), 8.00 (1H, t, J=6 Hz), 7.94 (1H, s), 7.88-0.775 (5H, m), 7.54 (2H, d, J=9 Hz), 5.95 (1H, s), 3.02-2.92 (2H, m), 1.78 (3H, s), 0.88 (3H, t, J=7.5 Hz).

Example 13
5-(4-Cyano-2-methanesulfonyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

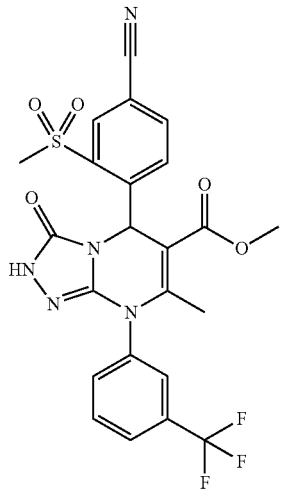

Intermediate 12 (235 mg, 0.44 mmol) was dissolved in DMSO (4.5 mL) and purged with $N_2$ for 5 mins. Sodium methane sulfinite (220 mg, 2.2 mmol) and trans-cyclohexane-1,2-diamine were then added, followed by copper(I) trifluoro-methanesulfonate benzene complex (222 mg, 0.44 mmol). The reaction mixture was stirred at 120° C. under $N_2$ for 18 h and then allowed to cool to RT. The reaction mixture was partitioned between EtOAc and water. The organic layer was separated, and the aqueous layer further extracted with EtOAc. The combined organic layers were washed with brine, dried ($Na_2SO_4$) and evaporated in vacuo. The resulting residue was purified by reverse phase HPLC using a gradient of 60-90% MeOH in water with 0.1% formic acid to give the title compound as a white solid (6.5 mg).

LC-MS (Method 3): Rt=4.37 min, m/z=534 [M+H]$^+$ $^1$H NMR (400 MHz, CDCl$_3$) δ 8.32 (1H, d, J=1 Hz), 7.91 (2H, dd, J=8, 1 Hz), 7.82 (1H, d, J=8 Hz), 7.73 (1H, t, J=8), 7.65-7.58 (4H, m), 3.57 (3H, s), 3.44 (3H, s), 2.22 (3H, s).

Example 14
5-(4-Cyano-phenyl)-7-methyl-3-oxo-8-(3-trifluoromethyl-phenyl)-2,3,5,8-tetrahydro-[1,2,4]triazolo[4,3-a]pyrimidine-6-carbonitrile

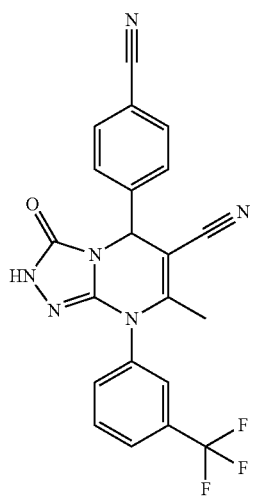 [SMILES: CC1=C(C#N)C(c2ccc(C#N)cc2)n2c(n[nH]c2=O)N1c1cccc(C(F)(F)F)c1]

Intermediate 13 (92 mg, 0.209 mmol) was dissolved in THF (8 mL), and Burgess reagent (150 mg, 0.63 mmol) was added. The reaction mixture was stirred at RT for 30 mins and was then partitioned between EtOAc and water. The organic layer was separated, and the aqueous layer further extracted with EtOAc. The combined organic layers were washed with brine, dried ($Na_2SO_4$) and evaporated in vacuo. The resulting residue was purified by silica gel chromatography eluting with 80% EtOAc in cyclohexane as eluent to yield a white solid. Further purification was carried out by reverse phase HPLC using a gradient of 40-98% MeCN in water (+0.1% formic acid) to yield the title compound as a white solid (34 mg).

LC-MS (Method 3): Rt=4.28 min, m/z=423 [M+H]$^+$ $^1$H NMR (400 MHz, CDCl$_3$) δ 8.07 (1H, s), 7.81 (1H, d, J=8), 7.75-7.69 (3H, m), 7.6 (1H, s), 7.54-7.49 (3H, m), 5.68 (1H, s), 2.05 (3H, s).

Example 15
5-(4-Cyano-phenyl)-2-(4-methanesulfonyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

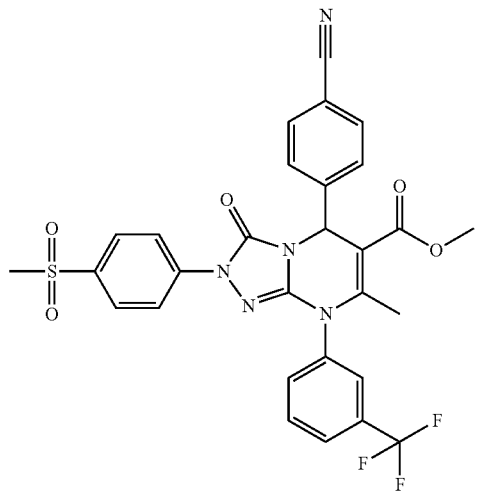

Example 1 (68 mg, 0.15 mmol) was dissolved in DCM (3 mL), and 4-methansulfonylphenyl boronic acid (90 mg, 0.45 mmol), copper (II) acetate (54 mg, 0.3 mmol), triethylamine (105 μL, 0.75 mmol), pyridine (48 μL, 0.6 mmol), and powdered 4 Å sieves (100 mg) were added. The reaction mixture was stirred at RT for 72 hours and was then filtered, and the filtrate collected and evaporated in vacuo. The resulting residue was purified by silica gel chromatography eluting with a gradient of 40-50% EtOAc in cyclohexane and the resulting residue was triturated with 1:1 EtOAc:MeOH, filtered and the solid collected to yield the title compound as a white solid (7 mg).

LC-MS (Method 3): Rt=5.10 min, m/z=610 [M+H]$^+$ $^1$H NMR (400 MHz, DMSO) δ 8.22 (1H, s), 8.03-7.97 (2H, m), 7.91-7.85 (5H, m), 7.81-7.77 (4H, m), 6.07 (1H, s), 3.57 (3H, s), 3.13 (3H, s), 2.18 (3H, s).

Example 16

5-(4-Cyano-phenyl)-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

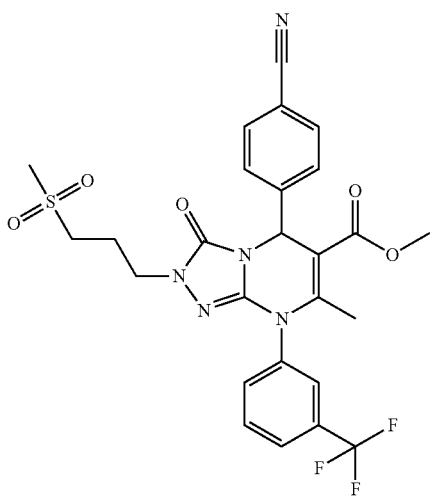 [SMILES: COC(=O)C1=C(C)N(c2cccc(C(F)(F)F)c2)c2nn(CCCS(C)(=O)=O)c(=O)n2C1c1ccc(C#N)cc1]

Example 1 (68 mg, 0.15 mmol) was dissolved in THF (2 mL) under an atmosphere on $N_2$, and 3-(methylsulfonyl)-1-propanol (25 mg, 0.18 mmol) and triphenylphosphine (47 mg, 0.18 mmol) were added followed by dropwise addition of DIAD (35 µL, 0.18 mmol) in THF (200 µL). The reaction mixture was stirred at RT for 5 hours, and then further 3-(methylsulfonyl)-1-propanol (25 mg, 0.18 mmol) and triphenylphosphine (47 mg, 0.18 mmol) were added followed by dropwise addition of DIAD (35 µL, 0.18 mmol) in THF (200 µL). The reaction mixture was stirred for a further 16 hours and then partitioned between EtOAc and water. The organic layer was separated, washed with brine, dried ($Na_2SO_4$) and evaporated in vacuo. The resulting residue was purified by silica gel chromatography eluting with a gradient of 50-100% EtOAc to give the title compound as a white solid (55 mg).

LC-MS (Method 3): Rt=4.50 min, m/z=576 $[M+H]^+$ $^1$H NMR (400 MHz, DMSO) δ 8.12 (1H, s), 7.92 (2H, dd, J=1 Hz and 7.5 Hz), 7.87-7.79 (3H, m), 7.69 (2H, d, J=7.5 Hz), 5.96 (1H, s), 3.68-3.60 (1H, m), 3.56 (3H, s), 3.55-3.47 (1H, m), 3.04-2.96 (2H, m), 2.88 (3H, s), 2.15 (3H, s), 1.89-1.79 (2H, m).

Example 17

(R)-5-(4-Cyano-phenyl)-2-(4-methanesulfonyl-benzyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

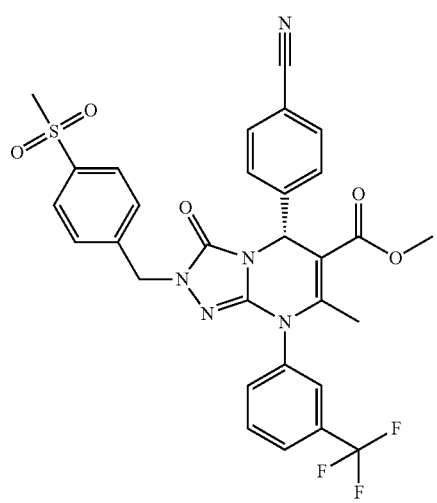 [SMILES: COC(=O)C1=C(C)N(c2cccc(C(F)(F)F)c2)c2nn(Cc3ccc(S(C)(=O)=O)cc3)c(=O)n2[C@@H]1c1ccc(C#N)cc1]

Example 7 (65 mg, 0.14 mmol) was dissolved in DMF (3 mL) and cesium carbonate (91 mg, 0.28 mmol) and 4-methylsulfonylbenzyl bromide (50 mg, 0.2 mmol) were added. The reaction mixture was stirred at RT for 3 hours and then partitioned between EtOAc and water. The organic layer was separated, washed with brine, dried ($Na_2SO_4$) and evaporated in vacuo. The resulting residue was purified by silica gel chromatography eluting with 80% EtOAc in cyclohexane to yield the title compound as a white solid (73 mg).

LC-MS (Method 3): Rt=4.78 min, m/z=624 $[M+H]^+$ $^1$H NMR (400 MHz, DMSO) δ 8.11 (1H, s), 7.93-7.85 (4H, m), 7.84-7.77 (3H, m), 7.71 (2H, d, J=8.5 Hz), 7.33 (2H, d, J=8.5 Hz), 6.00 (1H, s), 4.82 (2H, dd, J=16.5 Hz and 36.5 Hz), 3.56 (3H, s), 3.17 (3H, s), 2.14 (3H, s).

Example 18

(R)-5-(4-Cyano-phenyl)-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

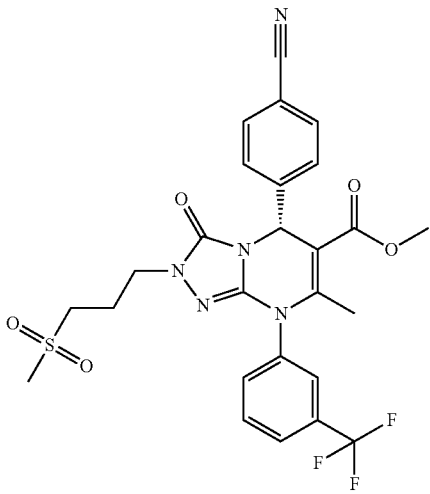 [SMILES: COC(=O)C1=C(C)N(c2cccc(C(F)(F)F)c2)c2nn(CCCS(C)(=O)=O)c(=O)n2[C@@H]1c1ccc(C#N)cc1]

Example 18 (85 mg) was prepared from Example 7 (91 mg, 0.25 mmol) and Intermediate 14 (50 mg, 0.25 mmol) according to an analogous procedure to that described for Example 17.

LC-MS (Method 3): Rt=4.48 min, m/z=576 [M+H]$^+$ $^1$H NMR (400 MHz, DMSO) δ 8.12 (1H, s), 7.92 (2H, dd, J=1 Hz and 7.5 Hz), 7.87-7.79 (3H, m), 7.69 (2H, d, J=7.5 Hz), 5.96 (1H, s), 3.68-3.60 (1H, m), 3.56 (3H, s), 3.55-3.47 (1H, m), 3.04-2.96 (2H, m), 2.88 (3H, s), 2.15 (3H, s), 1.89-1.79 (2H, m).

Example 19

5-(4-Cyano-phenyl)-2-(4-{[(2-dimethylamino-ethyl)-methyl-amino]-methyl}-benzenesulfonyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

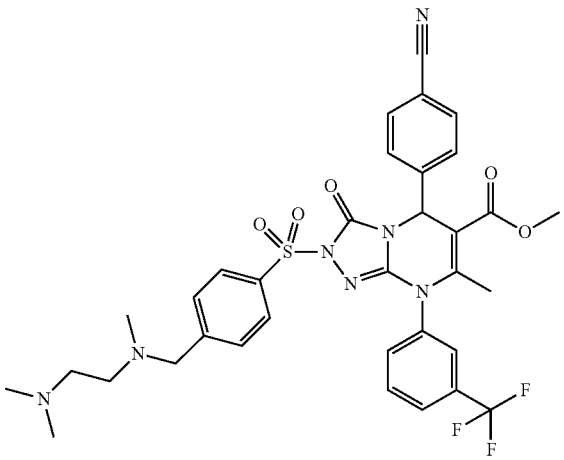

Example 1 (68 mg, 0.15 mmol) was dissolved in THF (2 mL), and cesium carbonate (81 mg, 0.25 mmol) and 4-(bromomethyl)-benzenesulfonyl chloride (49 mg, 0.18 mmol) were added. The reaction mixture was stirred at RT for 1 hour and then evaporated in vacuo. The resulting residue was re-dissolved in DMF (1 mL) and stirred at RT for a further 2 hours. N,N,N'-Trimethylethylenediamine (64 µL, 0.5 mmol) was added, and stirring at RT was continued for 5 hours. Additional N,N,N'-trimethylethylenediamine (150 µL, 1.2 mmol) was added, and stirring at RT was continued for 16 hours. The reaction mixture was partitioned between EtOAc and water. The organic layer was separated, washed with brine, dried (Na$_2$SO$_4$) and evaporated in vacuo. The resulting residue was purified by silica gel chromatography eluting with 10% MeOH, and the resulting residue was subjected to reverse phase HPLC using a gradient of 40-60% acetonitrile in water with 0.1% ammonia and gave the title compound as a white solid (7 mg).

LC-MS (Method 3): Rt=3.84 min, m/z=710 [M+H]$^+$ $^1$H NMR (400 MHz, DMSO) δ 8.03 (1H, s), 8.00-7.96 (1H, m), 7.89-7.85 (2H, m), 7.78 (2H, d, J=8 Hz), 7.59 (2H, d, J=8 Hz), 7.56 (2H, d, J=8 Hz), 7.47 (2H, d, J=8 Hz), 5.87 (1H, s), 3.58 (2H, s), 3.51 (3H, s), 2.48-2.43 (2H, m), 2.40-2.35 (2H, m), 2.13 (3H, s), 2.12 (6H, s), 2.08 (3H, s).

Example 20

(R)-5-(4-Cyano-phenyl)-2-[2-(4-methanesulfonyl-phenyl)-ethyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

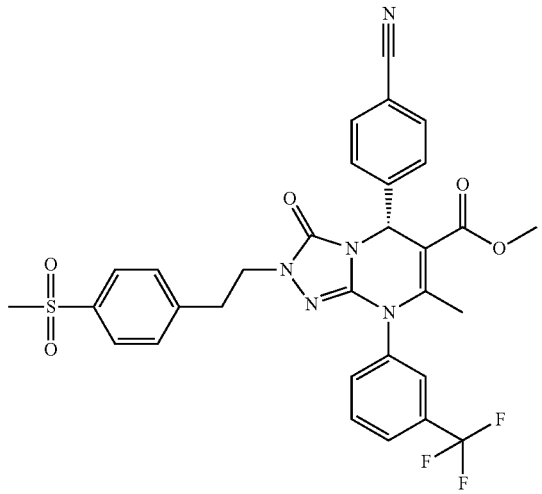

Example 7 (54 mg, 0.12 mmol) was dissolved in DMF (3 mL), and cesium carbonate (59 mg, 0.18 mmol) and 1-(2-bromoethyl)-4-(methylsulfonyl)benzene (39 mg, 0.15 mmol) were added. The reaction mixture was stirred at RT for 16 hours, then the temperature was raised to 70° C., and stirring was continued for 3 hours. The reaction mixture was allowed to cool to RT, then further cesium carbonate (59 mg, 0.18 mmol) and 1-(2-bromoethyl)-4-(methylsulfonyl)benzene (39 mg, 0.15 mmol) were added. The reaction mixture was stirred at RT for 2 hours and then partitioned between EtOAc and water. The organic layer was separated, washed with brine, dried (Na$_2$SO$_4$) and evaporated in vacuo. The resulting residue was purified by silica gel chromatography eluting with a gradient of 50-80% EtOAc in cyclohexane to yield the title compound as an off-white solid (45 mg).

LC-MS (Method 3): Rt=4.81 min, m/z=638 [M+H]$^+$ $^1$H NMR (400 MHz, DMSO) δ 8.12 (1H, s), 7.95-7.91 (1H, m), 7.90=7.80 (4H, m), 7.74 (2H, d, J=8 Hz), 7.63 (2H, d, J=8 Hz), 7.29 (2H, d, J=8 Hz), 5.90 (1H, s), 3.81-3.66 (2H, m), 3.54 (3H, s), 3.15 (3H, s) 2.87-2.82 (2H, m), 2.14 (3H, s).

Example 21

5-(4-Cyano-phenyl)-2-(4-dimethylaminomethyl-benzyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

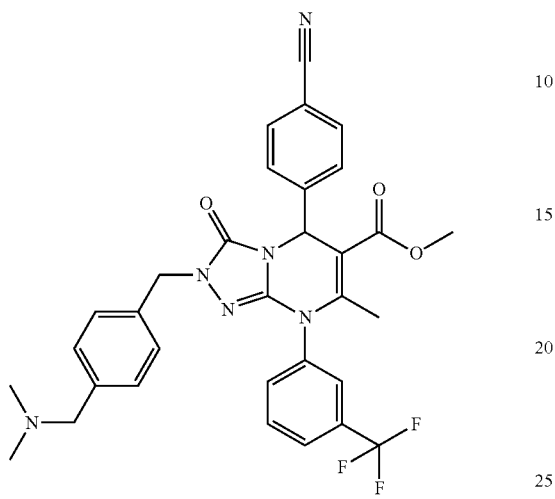

Intermediate 15 (105 mg, 0.16 mmol) was dissolved in THF (3 ml), and then dimethylamine (2 M in THF, 400 μl, 0.8 mmol) was added. The reaction mixture was stirred at RT for 16 hours and then filtered. The filtrate was collected and concentrated in vacuo. The resulting residue was purified by silica gel chromatography eluting with a gradient of 5-8% MeOH in DCM and gave the title compound as a white solid (72 mg).

LC-MS (Method 3): Rt=3.69 min, m/z=603 [M+H]$^+$ $^1$H NMR (400 MHz, DMSO) δ 8.04 (1H, s), 7.87-7.79 (4H, m), 7.76-7.71 (1H, m), 7.64 (2H, d, J=8 Hz), 7.10 (2H, d, J=8 Hz), 6.95 (2H, d, J=8 Hz), 5.95 (1H, s), 4.64 (1H, d, J=15 Hz), 4.56 (1H, d, J=15 Hz), 3.50 (3H, s), 3.28-3.21 (2H, m), 2.09 (3H, s), 2.05 (6H, s).

Example 22

{4-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-ylmethyl]-benzyl}-trimethyl-ammonium bromide

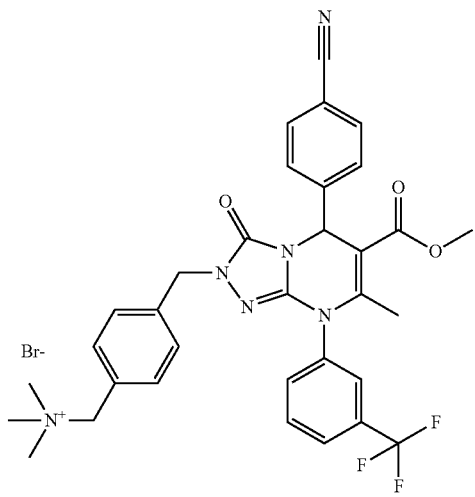

Intermediate 15 (105 mg, 0.16 mmol) was dissolved in a solution of 31% trimethylamine in ethanol. The reaction mixture was stirred at RT for 16 hours and then filtered. The solid was collected by filtration and dried in vacuo to yield the title compound as a white solid (62 mg).

LC-MS (Method 3): Rt=3.71 min, m/z=617 [M+H]$^+$ $^1$H NMR (400 MHz, DMSO) δ 8.10 (1H, s), 7.94-7.85 (4H, m), 7.82-7.77 (1H, m), 7.72 (2H, d, J=8 Hz), 7.43 (2H, d, J=8 Hz), 7.19 (2H, d, J=8 Hz), 6.00 (1H, s), 4.80 (1H, d, J=16 Hz), 4.72 (1H, d, J=16 Hz), 4.47 (2H, s), 3.57 (3H, s), 2.98 (9H, s), 2.16 (3H, s).

Example 23

5-(4-Cyano-phenyl)-2-(5-methanesulfonyl-pyridin-2-ylmethyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester

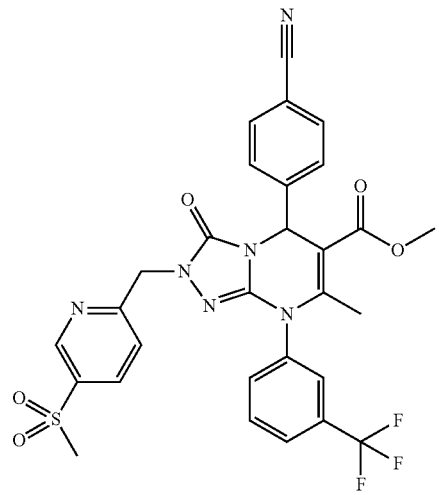 [SMILES: COC(=O)C1=C(C)N(c2cccc(C(F)(F)F)c2)c2nn(Cc3ccc(S(C)(=O)=O)cn3)c(=O)n2C1c1ccc(C#N)cc1]

Example 1 (50 mg, 0.11 mmol) was dissolved in DMF (1 mL), and cesium carbonate (43 mg, 0.13 mmol), 2-chloromethyl-5-methanesulfonyl-pyridine (25 mg, 0.12 mmol), and sodium iodide (2 mg, 0.011 mmol) were added. The reaction mixture was stirred at RT for 16 hours and then partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with a gradient of 0-50% EtOAc in DCM to yield the title compound as a white solid (41 mg).

LC-MS (Method 3): Rt=4.63 min, m/z=625 [M+H]$^+$ $^1$H NMR (400 MHz, DMSO) δ 8.86 (1H, d, J=2 Hz), 8.18 (1H, dd, J=9 and 2 Hz), 8.05 (1H, s), 7.86-7.82 (4H, m), 7.75-7.71 (1H, m), 7.67 (2H, d, J=9 Hz), 7.31 (1H, d, J=8 Hz), 5.97 (1H, s), 4.91 (1H, d, J=17 Hz), 4.83 (1H, d, J=17 Hz), 3.52 (3H, s), 3.24 (3H, s), 2.10 (3H, s).

Example 24

5-(4-Cyano-phenyl)-7-methyl-3-oxo-2-[3-(2-oxo-pyrrolidin-1-yl)-propyl]-8-(3-trifluoromethyl-phenyl)-2,3,5,8-tetrahydro-[1,2,4]triazolo[4,3-a]pyrimidine-6-carboxylic acid methyl ester

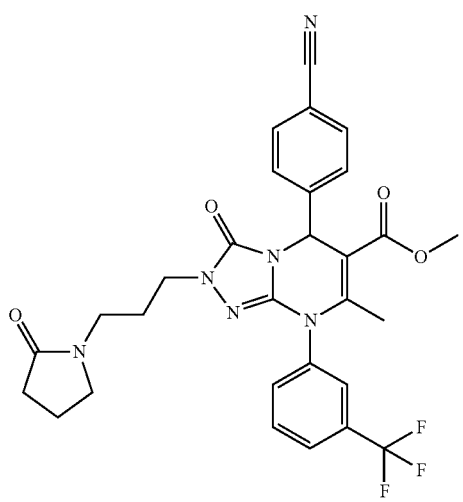 [SMILES: COC(=O)C1=C(C)N(c2cccc(C(F)(F)F)c2)c2nn(CCCN3CCCC3=O)c(=O)n2C1c1ccc(C#N)cc1]

Example 1 (35 mg, 0.08 mmol) was dissolved in THF (2 mL), and N-(3-hydroxypropyl)-2-pyrrolidone (12 µL, 0.09 mmol) and triphenylphosphine (59 mg, 0.22 mmol) were added followed by diethyl azodicarboxylate (42 µl, 0.27 mmol). The reaction mixture was stirred at RT for 2 hours and was then partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with a gradient of 0-10% MeOH in DCM. Further purification was carried out by reverse phase HPLC using a gradient of 50-98% MeOH in water+0.1% formic acid to yield the title compound as a white solid (10 mg).

LC-MS (Method 3): Rt=4.50 min, m/z=581 [M+H]$^+$ $^1$H NMR (400 MHz, CDCl$_3$) δ 7.76 (1H, d, J=8 Hz), 7.70-7.63 (3H, m), 7.59-7.53 (4H, m), 6.10 (1H, s), 3.61 (3H, s), 3.60-3.56 (1H, m), 3.50-3.43 (1H, m), 3.25 (2H, t, J=7 Hz), 3.21-3.13 (2H, m), 2.29 (2H, t, J=8 Hz), 2.23 (3H, s), 1.97-1.91 (2H, m), 1.84-1.78 (2H, m).

Example 25

5-(4-Cyano-phenyl)-2-{[(2-dimethylamino-ethyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester

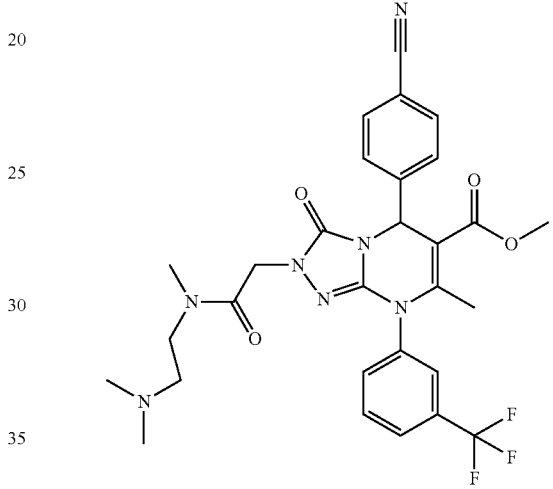

Intermediate 17 (48 mg, 0.09 mmol) was dissolved in DMF (1 mL), and then diisopropylethylamine (48 µL, 0.28 mmol) and HATU (39 mg, 0.10 mmol) were added. The reaction mixture was stirred at RT for 30 minutes and then N,N,N-trimethylethylenediamine (36 µL, 0.28 mmol) was added. After 3 hours of stirring at RT, another portion of HATU was added (10 mg, 0.03 mmol), and stirring was continued for 1 hour. The reaction mixture was partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with a gradient of 0-10% (2M NH$_3$ in MeOH) in DCM to give the title compound as a white solid (40 mg).

LC-MS (Method 3): Rt=3.52 min, m/z=598 [M+H]$^+$ $^1$H NMR (400 MHz, CDCl$_3$) δ 7.73 (1H, d, J=8 Hz), 7.66-7.62 (3H, m), 7.58 (1H, s), 7.56-7.53 (3H, m), 6.15 (1H, s), 4.37 (1H, d, J=17 Hz), 4.28 (1H, d, J=17 Hz), 3.63 (3H, s), 3.40 (1H, m), 3.22 (1H, t, J=7 Hz), 2.90 (3H, s), 2.42-2.35 (2H, m), 2.22 (3H, s), 2.20 (3H, s), 2.16 (3H, s).

Example 26

5-(4-Cyano-phenyl)-2-{[(3-dimethylamino-propyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester

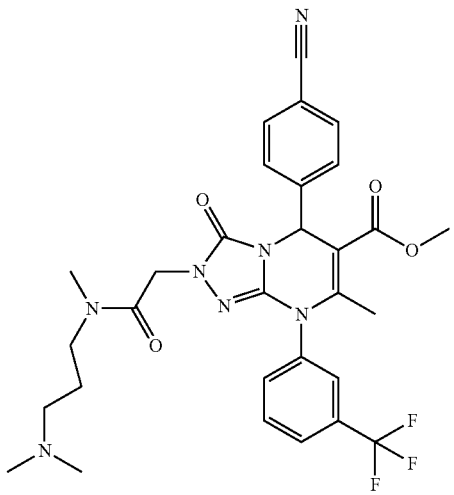

Intermediate 17 (57 mg, 0.11 mmol) was dissolved in DMF (1 mL), and then diisopropylethylamine (56 μL, 0.33 mmol) and HATU (63 mg, 0.17 mmol) were added. The reaction mixture was stirred at RT for 30 minutes, then N,N,N-trimethylpropanediamine (49 μL, 0.33 mmol) was added, and stirring was continued for a further 2 hours. The reaction mixture was partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with a gradient of 0-10% (2M NH$_3$ in MeOH) in DCM to yield the title compound as a white solid (42 mg).

LC-MS (Method 3): Rt=3.52 min, m/z=612 [M+H]$^+$ $^1$H NMR (400 MHz, CDCl$_3$) δ 7.72 (1H, t, J=8 Hz), 7.66-7.61 (3H, m), 7.59-7.50 (4H, m), 6.17 (1H, s), 4.55 (2H, s), 3.63 (3H, s), 3.30 (1H, t, J=8 Hz), 3.25-3.16 (1H, m), 2.82 (3H, s), 2.20 (3H, s), 2.16 (3H, s), 2.14-2.10 (2H, m), 2.06 (3H, s), 1.66-1.59 (2H, m).

Example 27

[2-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)-ethyl]-trimethyl-ammonium bromide

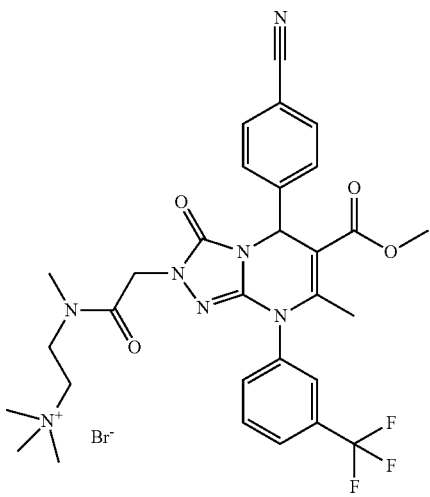

Example 25 (28 mg, 0.05 mmol) was dissolved in acetonitrile (0.5 mL), and then methyl bromide (23 μL of 30% solution in acetonitrile, 0.07 mmol) was added. The reaction mixture was stirred at RT for 5 days, and during this period methyl bromide (50 μL) was added every 12 hours. Potassium carbonate (20 mg) was then added to the reaction mixture, and stirring was continued for 12 hours. The reaction mixture was filtered and the filtrate evaporated in vacuo to yield the title compound as a white solid (32 mg).

LC-MS (Method 3): Rt=3.48 min, m/z=612 [M]$^+$ $^1$H NMR (400 MHz, DMSO) δ 8.05 (1H, s), 7.90-7.74 (5H, m), 4.68 (2H, d, J=9 Hz), 5.93 (1H, s), 4.47 (1H, d, J=17 Hz), 4.41 (1H, d, J=17 Hz), 3.59-3.53 (2H, m), 3.51 (3H, s), 3.31-3.23 (2H, m), 2.97 (9H, s), 2.88 (3H, s), 2.10 (3H, s).

Example 28

[3-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)propyl]-trimethyl-ammonium; bromide

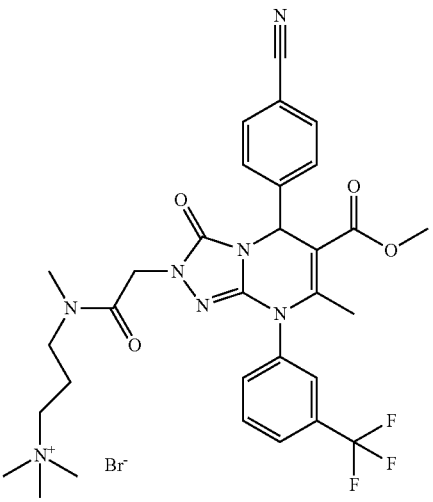

Example 26 (32 mg, 0.05 mmol) was dissolved in acetonitrile (0.5 mL), and then methyl bromide (25 μL of 30% solution in acetonitrile, 0.07 mmol) was added. The reaction mixture was stirred at RT for 3 days, and during this period methyl bromide (25 μL) was added every 12 hours. The reaction mixture was filtered, and the filtrate evaporated in vacuo to yield the title compound as a white solid (36 mg).

LC-MS (Method 3): Rt=3.51 min, m/z=626 [M]$^+$ $^1$H NMR (400 MHz, DMSO) δ 8.05 (1H, s), 7.90-7.74 (5H, m), 7.64 (2H, d, J=8 Hz), 5.93 (1H, s), 4.41 (1H, d, J=17 Hz), 4.36 (1H, d, J=17 Hz), 3.52 (3H, s), 3.21-3.06 (4H, m), 2.93 (9H, s), 2.84 (3H, s), 2.10 (3H, s), 1.80-1.73 (2H, m).

Example 29

5-(4-Cyano-phenyl)-2-{[(4-dimethylamino-butyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester

Example 30

5-(4-Cyano-phenyl)-2-{[(5-dimethylamino-pentyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester

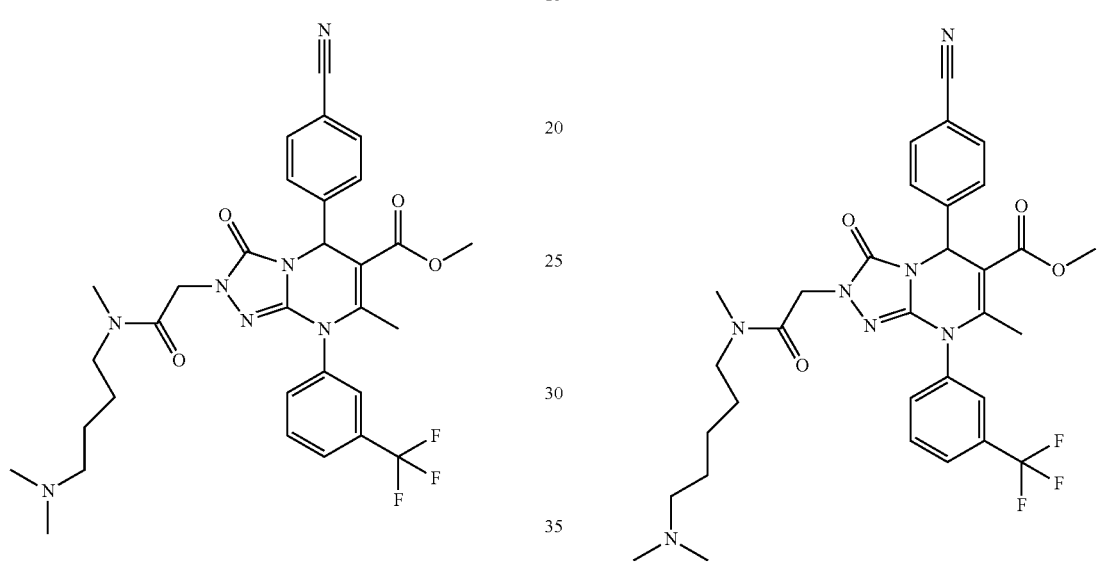

Intermediate 17 (50 mg, 0.10 mmol) was dissolved in DMF (1 mL). and diisopropylethylamine (50 µL, 0.29 mmol) and HATU (41 mg, 0.11 mmol) were added. The reaction mixture was stirred at RT for 30 minutes, then N,N,N-trimethylbutanediamine (38 mg, 0.29 mmol) was added, and stirring was continued for a further 18 hours. The reaction mixture was partitioned between EtOAc and water. The organic layer was separated, and the aqueous layer further extracted with EtOAc. The combined organic layers were washed with brine, dried ($Na_2SO_4$) and evaporated in vacuo. The resulting residue was purified by silica gel chromatography eluting with a gradient of 0-10% (2M $NH_3$ in MeOH) in DCM to yield the title compound as a white solid (34 mg).

LC-MS (Method 3): Rt=3.54 min, m/z=626 [M+H]$^+$ $^1$H NMR (400 MHz, $CDCl_3$) δ 7.73 (1H, t, J=8 Hz), 7.65-7.62 (3H, m), 7.57-7.53 (4H, m), 6.15 (1H, s), 4.30 (1H, d, J=17 Hz), 4.26 (1H, d, J=17 Hz), 3.63 (3H, s), 3.29 (2H, t, J=7 Hz), 2.88 (3H, s), 2.25 (2H, t, J=8 Hz), 2.20 (3H, s), 2.18 (3H, s), 2.13 (3H, s), 1.55-1.36 (4H, m).

Intermediate 17 (45 mg, 0.09 mmol) was dissolved in DMF (1 mL), and then diisopropylethylamine (75 µL, 0.44 mmol) and HATU (51 mg, 0.14 mmol) were added. The reaction mixture was stirred at RT for 30 minutes, then N,N,N-trimethylpentanediamine (63 mg, 0.44 mmol) was added, and stirring was continued for a further 18 hours. The reaction mixture was partitioned between EtOAc and water. The organic layer was separated, and the aqueous layer extracted with EtOAc. The combined organic layers were washed with brine, dried ($Na_2SO_4$) and evaporated in vacuo. The resulting residue was purified by silica gel chromatography eluting with a gradient of 0-10% (2M $NH_3$ in MeOH) in DCM to give the title compound as a white solid (44 mg).

LC-MS (Method 3): Rt=3.59 min, m/z=640 [M+H]$^+$ $^1$H NMR (400 MHz, $CDCl_3$) δ 7.73 (1H, t, J=8 Hz), 7.67-7.64 (3H, m), 7.57-7.52 (4H, m), 6.12 (1H, s), 4.37 (2H, s), 3.64 (3H, s), 3.45 (2H, dd, J=14, 7 Hz), 2.86 (3H, s), 2.64 (6H, s), 2.43 (2H, br s), 2.20 (3H, s), 1.65-1.21 (6H, m).

Example 31

[4-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)-butyl]-trimethylammonium bromide

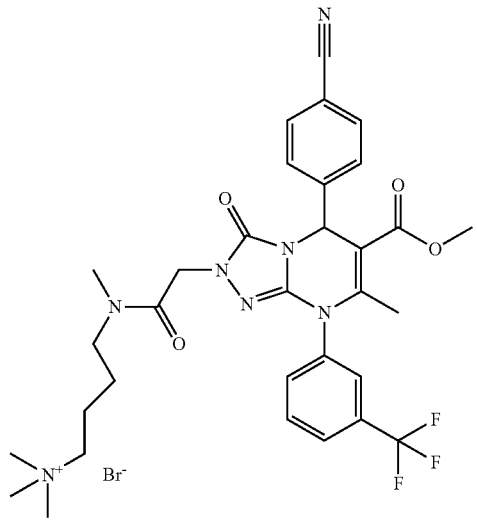

Example 29 (21 mg, 0.03 mmol) was dissolved in a 30% methyl bromide in acetonitrile solution (1 mL), and potassium carbonate (30 mg) was added. The reaction mixture was stirred at RT for 3 days and then filtered and the filtrate evaporated in vacuo to yield the title compound as a white solid (25 mg).

LC-MS (Method 3): Rt=3.54 min, m/z=640 [M]$^+$ $^1$H NMR (400 MHz, CDCl$_3$) δ 7.76-7.74 (2H, m), 7.70-7.66 (2H, m), 7.57-7.54 (4H, m), 6.09 (1H, s), 4.40 (1H, d, J=17 Hz), 4.35 (1H, d, J=17 Hz), 3.65 (3H, s), 3.65-3.60 (2H, m), 3.36-3.29 (2H, m), 3.16 (9H, s), 2.90 (3H, s), 2.20 (3H, s), 1.71-1.59 (4H, m).

Example 32

[5-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)pentyl]-trimethyl-ammonium; bromide

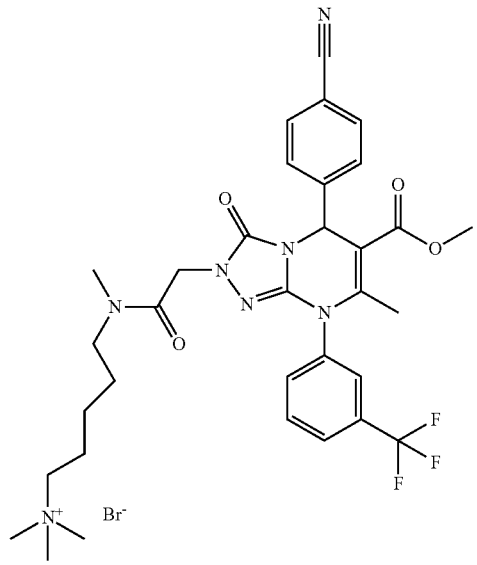

Example 30 (34 mg, 0.05 mmol) was dissolved in a 30% methyl bromide in acetonitrile solution (1 mL), and then potassium carbonate (30 mg) was added. The reaction mixture was stirred at RT for 24 hours and then filtered and evaporated in vacuo to yield the title compound as a white solid (37 mg).

LC-MS (Method 3): Rt=3.62 min, m/z=654 [M]$^+$ $^1$H NMR (400 MHz, DMSO) δ 8.04 (1H, s), 7.88-7.75 (5H, m), 7.64 (2H, dd, J=8, 1 Hz), 5.92 (1H, s), 4.38 (2H, s), 3.52 (3H, s), 3.26 (9H, s), 3.17-3.13 (4H, m), 2.94 (3H, s), 2.10 (3H, s), 1.64-1.54 (2H, m), 1.46-1.34 (2H, m), 1.19-1.07 (2H, m).

Example 33

(R)-5-(4-Cyano-phenyl)-2-{[(5-dimethylamino-pentyl)-methyl-carbamoyl]-methyl}-7-methyl-3-oxo-8-(3-trifluoromethyl-phenyl)-2,3,5,8-tetrahydro-[1,2,4]-triazolo[4,3-a]pyrimidine-6-carboxylic acid methyl ester

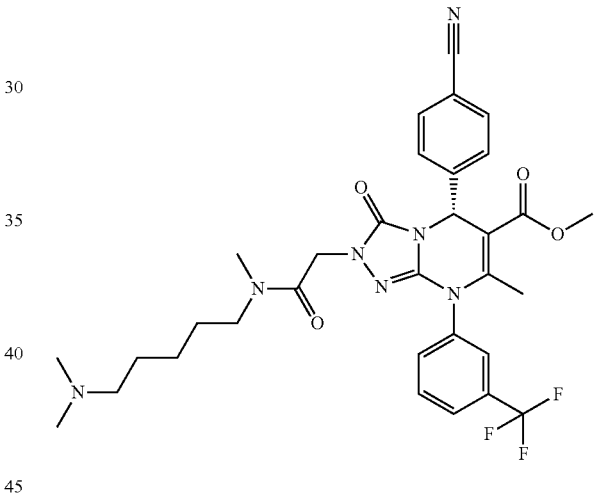

Intermediate 26 (250 mg, 0.46 mmol) was dissolved in DMF (5 mL), and then diisopropylethylamine (240 μL, 1.4 mmol) and HATU (266 mg, 0.7 mmol) were added. The reaction mixture was stirred at RT for 40 minutes, then N,N,N-trimethylpentanediamine (288 mg, 2.0 mmol) in DMF (1 mL) was added, and stirring was continued for a further 18 hours. The reaction mixture was partitioned between EtOAc and water. The organic layer was separated, and the aqueous layer extracted with EtOAc. The combined organic layers were washed with brine, dried (Na$_2$SO$_4$) and evaporated in vacuo. The resulting residue was purified by silica gel chromatography eluting with a gradient of 4-8% (2 M NH$_3$ in MeOH) in DCM followed by a gradient of 6-7% (2 M NH$_3$ in MeOH) in DCM. The resulting residue was purified by MDAP to yield the title compound as an off-white solid (88 mg).

LC-MS (Method 3): Rt=3.52 min, m/z=640 [M+H]$^+$ $^1$H NMR (400 MHz, CDCl$_3$) δ 7.73 (1H, t, J=8 Hz), 7.67-7.64 (3H, m), 7.57-7.52 (4H, m), 6.12 (1H, s), 4.37 (2H, s), 3.64 (3H, s), 3.45 (2H, dd, J=14, 7 Hz), 2.86 (3H, s), 2.64 (6H, s), 2.43 (2H, br s), 2.20 (3H, s), 1.65-1.21 (6H, m).

Example 34

(R)-[5-({2-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)pentyl]-trimethyl-ammonium chloride

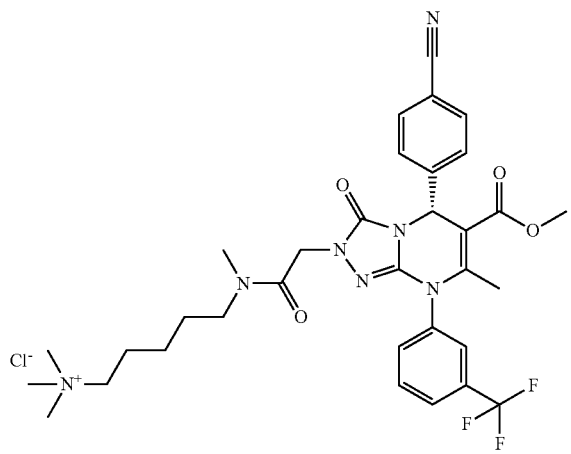

Example 33 (88 mg, 0.14 mmol) was dissolved in a 30% methyl bromide in acetonitrile solution (2 mL), and then potassium carbonate (39 mg) was added. The reaction mixture was stirred at RT for 24 hours and then filtered and evaporated in vacuo and dissolved in water. The resulting solution was eluted through Amberlite IRA458 resin and freeze dried to give the title compound as a white solid (49 mg).

LC-MS (Method 3): Rt=3.62 min, m/z=654 [M]$^+$ $^1$H NMR (400 MHz, DMSO) δ 8.04 (1H, s), 7.88-7.75 (5H, m), 7.64 (2H, dd, J=8, 1 Hz), 5.92 (1H, s), 4.38 (2H, s), 3.52 (3H, s), 3.26 (9H, s), 3.17-3.13 (4H, m), 2.94 (3H, s), 2.10 (3H, s), 1.64-1.54 (2H, m), 1.46-1.34 (2H, m), 1.19-1.07 (2H, m).

Example 35

2-[3-(Acetyl-methyl-amino)-propyl]-5-(4-cyano-phenyl)-7-methyl-3-oxo-8-(3-trifluoromethylphenyl)-2,3,5,8-tetrahydro-[1,2,4]triazolo[4,3-a]pyrimidine-6-carboxylic acid methyl ester

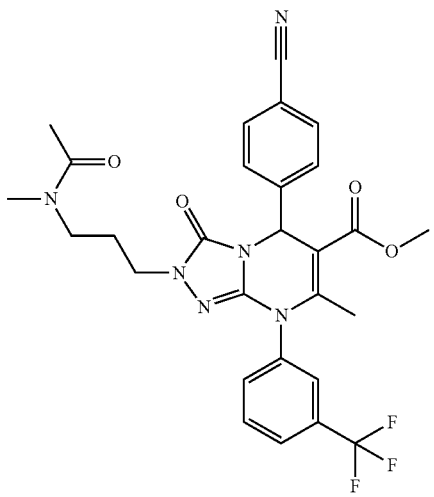

To a solution of Intermediate 18 (0.12 g, 0.19 mmol) in DCM (2.5 mL), was added TFA (0.25 mL). The resulting mixture was stirred at RT for 1 hour, and then evaporated in vacuo. The resulting residue was taken up in DCM (4 mL), and triethylamine (86 µL, 0.62 mmol) was added, followed by acetic anhydride (47 µL, 0.50 mmol). The reaction mixture was stirred at RT for 30 mins and was then partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with a gradient 0-10% MeOH in DCM to yield the title compound as a white solid (80 mg).

LC-MS (Method 3): Rt=4.45 min, m/z=569 [M+H]$^+$ $^1$H NMR (400 MHz, DMSO) δ 8.06 (1H, d, J=6 Hz), 7.87-7.85 (2H, m), 7.82-7.75 (3H, m), 7.63 (2H, dd, J=8, 2 Hz), 5.91 (1H, s), 3.50 (3H, s), 3.46-3.30 (2H, m), 3.10-2.99 (2H, m), 2.75 (3H, s), 2.10 (3H, s), 1.84 (3H, s), 1.58-1.50 (2H, m).

Example 36

5-(4-Cyano-phenyl)-2-[3-(methanesulfonyl-methyl-amino)-propyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester

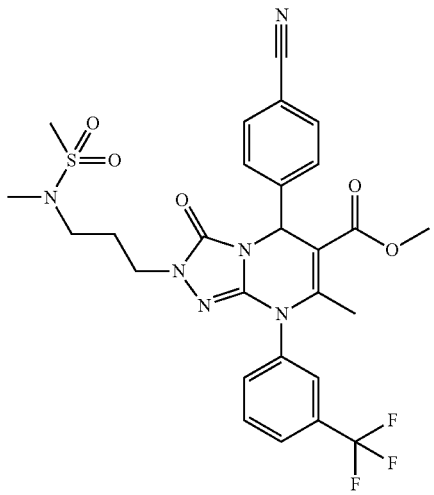

To a solution of Intermediate 18 (0.12 g, 0.19 mmol) in DCM (2.5 mL) and TFA (0.25 mL) was added. The resulting mixture was stirred at RT for 1 hour and then evaporated in vacuo. The resulting residue was taken up in DCM (4 mL), and then triethylamine (105 µL, 0.75 mmol) added, followed by methanesulfonyl chloride (28 µL, 0.36 mmol). The reaction mixture was stirred at RT for 30 mins and then partitioned between EtOAc and water. The organic layer was separated, and the aqueous layer further extracted with EtOAc. The combined organic layers were washed with brine, dried (Na$_2$SO$_4$) and evaporated in vacuo. The resulting residue was purified by silica gel chromatography eluting with a gradient of 0-10% MeOH in DCM as eluent to yield the title compound as a white solid (106 mg).

LC-MS (Method 3): Rt=4.45 min, m/z=605 [M+H]$^+$ $^1$H NMR (400 MHz, DMSO) δ 8.06 (1H, s), 7.88-7.85 (2H, m), 7.81-7.75 (3H, m), 7.63 (2H, d, J=8 Hz), 5.91 (1H, s), 3.51 (3H, s), 3.41-3.31 (2H, m), 2.87 (2H, td, J=8, 2 Hz), 2.72 (3H, s), 2.56 (3H, s), 2.10 (3H, s), 1.69-1.58 (2H, m).

Example 37

(3-{3-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-propane-1-sulfonyl}-propyl)-trimethylammonium toluene-4-sulfonate

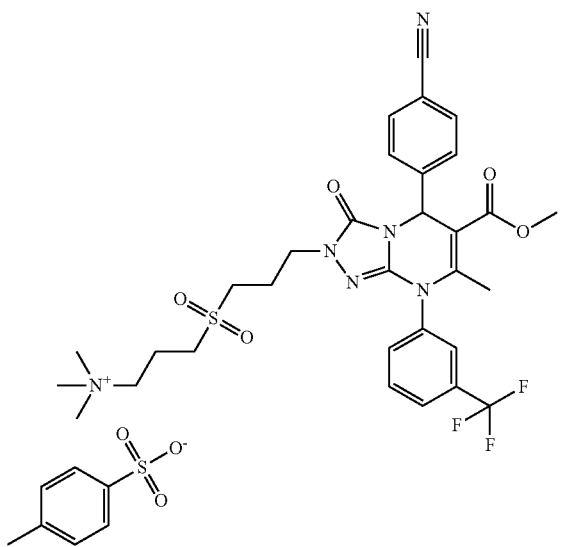

Intermediate 23 (68 mg, 0.09 mmol) was dissolved in 31% trimethylamine in ethanol (3 ml) and stirred at RT for 16 hours. The solvent was evaporated in vacuo, and the resulting residue repeatedly azeotroped with diethyl ether until a solid formed. The solid was collected and dried in vacuo to yield the title compound as an off-white solid (51 mg).

LC-MS (Method 3): Rt=3.59 min, m/z=661 [M+H]$^+$ $^1$H NMR (400 MHz, DMSO) δ 8.12 (1H, s), 7.94-7.89 (2H, m), 7.88-7.80 (3H, m), 7.69 (2H, d, J=8 Hz), 7.47 (2H, d, J=8 Hz), 7.11 (2H, d, J=8 Hz), 5.96 (1H, s), 3.68-3.60 (1H, m), 3.59-3.50 (1H, m), 3.56 (3H, s), 3.38-3.32 (2H, m), 3.13-3.07 (4H, m), 3.05 (9H, s), 2.29 (3H, s), 2.15 (3H, s), 2.12-2.04 (2H, m), 1.90-1.79 (2H, m).

Example 38

(R)-(3-{3-[5-(4-Cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-propane-1-sulfonyl}-propyl)-trimethylammonium chloride

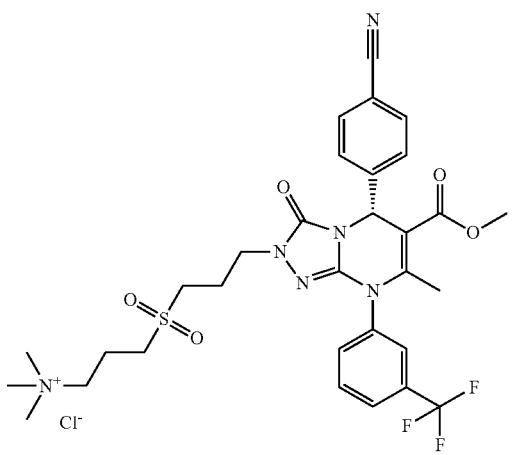

Intermediate 29 (128 mg, 0.17 mmol) was dissolved in 31% trimethylamine in ethanol (6 ml) and stirred at RT for 16 hours. The solvent was removed, and the resulting residue was purified by reverse phase HPLC using a gradient of 10-98% acetonitrile in water with 0.1% formic acid. The title compound was obtained following elution through Amberlite IRA458 resin and freeze-drying of the eluent to give a white solid (72 mg).

LC-MS (Method 3): Rt=3.52 min, m/z=661 [M]$^+$ $^1$H NMR (400 MHz, DMSO) δ 8.12 (1H, s), 7.94-7.89 (2H, m), 7.88-7.80 (3H, m), 7.69 (2H, d, J=8 Hz), 5.96 (1H, s), 3.68-3.60 (1H, m), 3.59-3.50 (1H, m), 3.56 (3H, s), 3.38-3.32 (2H, m), 3.13-3.07 (4H, m), 3.05 (9H, s), 2.15 (3H, s), 2.12-2.04 (2H, m), 1.90-1.79 (2H, m).

Example 39

(3-{3-[6-Cyano-5-(4-cyano-phenyl)-7-methyl-3-oxo-8-(3-trifluoromethyl-phenyl)-5,8-dihydro-[1,2,4]triazolo[4,3-a]pyrimidin-2-yl]-propane-1-sulfonyl}-propyl)-trimethylammonium toluene-4-sulfonate

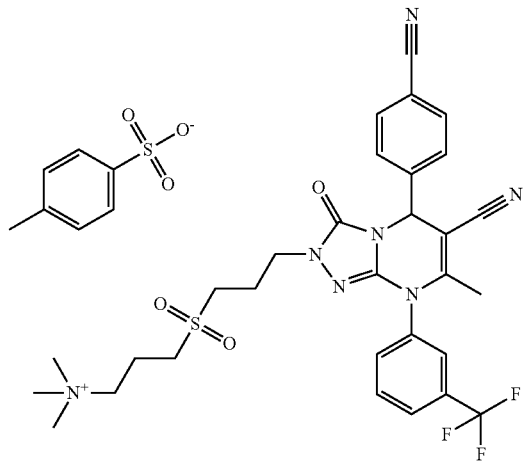 [SMILES: Cc1ccc(S(=O)(=O)[O-])cc1 ; CC1=C(C#N)C(c2ccc(C#N)cc2)n2c(nn(CCCS(=O)(=O)CCC[N+](C)(C)C)c2=O)N1c1cccc(C(F)(F)F)c1]

Example 39 (89 mg) was prepared from Example 14 (331 mg, 0.78 mmol) and Intermediate 20 (296 mg, 1 mmol) according to analogous procedures to those described for Intermediate 23 then Example 37.

LC-MS (Method 3): Rt=3.45 min, m/z=628 [M]$^+$ $^1$H NMR (400 MHz, DMSO) δ 8.12 (1H, s), 7.93-7.84 (4H, m), 7.81-7.70 (3H, m), 7.43 (2H, d, J=7.6 Hz), 7.06 (2H, d, J=7.6 Hz), 5.88 (1H, s), 3.65-3.48 (2H, m), 3.33-3.2 (2H, m), 3.10-3.04 (4H, m), 3.01 (9H, s), 2.24 (3H, s), 2.10-1.98 (2H, m), 1.89 (3H, s), 1.86-1.77 (2H, m).

Biological Assay.

Compounds of this invention were tested for potency in a human neutrophil elastase (HNE) enzyme activity assay.

HNE Enzyme Assay.

Assays were performed in 96-well plates in a total assay volume of 100 µl. The final concentration of elastase enzyme (human leukocyte elastase, Sigma E8140) was 0.0036 units/well or 0.00072 U/mL. The peptide substrate (MeOSuc-Ala-Ala-Pro-Val-AMC, Calbiochem #324740) was used at a final concentration of 100 µM. The final concentration of DMSO was 1% in the assay buffer (0.05M Tris.HCl, 0.1M NaCl, 0.1M CaCl$_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 µg/well. Fluorescence was measured using a Molecular Devices fluorescence plate reader using 380 nm excitation and 460 nm emission wavelengths.

A dose response to each compound was performed, and the effect of the compound in each experiment was expressed as a percentage inhibition of the control enzyme fluorescence. Dose response curves were plotted and compound potency ($IC_{50}$) was determined. Compounds were tested in at least two separate experiments.

$IC_{50}$s for tested Examples, representative of the invention, are shown in the following table:

| Example | HNE inhibition |
|---|---|
| 33, 34, 38, 18, 13, 39, 14, 37, 36, 35, 32, 30, 31, 29, 21, 22, 11, 27, 28, 16, 26, 25, 24, 15, 10, 23, 8, 20, 17, 9, 3, 2, 1, 5, 6 | ++++ |
| 19, 12, 4 | +++ |

In the table above, HNE enzyme inhibition ($IC_{50}$ values) are indicated as follows:
>500 nM "+"; 100 to 500 nM "++"; 20 to 100 nM "+++"; and <20 nM "++++".

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound represented by formula (I):

(I)

wherein:
A is CH or N;
$R_1$ is:
  hydrogen;
  $(C_1-C_6)$alkyl;
  $NR_7R_8(C_1-C_6)$alkyl;
  $(C_1-C_4)$alkenyl;
  phenyl$(C_1-C_6)$alkyl wherein such phenyl ring is optionally substituted by $NR_{15}R_{16}(C_1-C_6)$alkyl or by $N^+R_{15}R_{16}R_{17}(C_1-C_6)$alkyl;
  a group —$CH_2(CH_2)_n$OH;
  a group —$(CH_2)_n$CONR$_5$R$_6$;
  a group —$(CH_2)_n$SO$_2$NR$_5$R$_6$;
  a group —$CH_2$—$(CH_2)_n$NR$_5$SO$_2$R$_6$;
  a group —$(CH_2)_r$—$(C_6H_4)$—SO$_2$(C$_1$-C$_4$)alkyl;
  a group —$(CH_2)_r$SO$_2$(C$_1$-C$_4$)alkyl wherein such $(C_1-C_4)$alkyl is optionally substituted by a group —$NR_{15}R_{16}$ or —$N^+R_{15}R_{16}R_{17}$;
  a group —$SO_2$-phenyl wherein such phenyl ring is optionally substituted by $NR_7R_8(C_1-C_6)$alkyl; or
  a group —$(CH_2)_n$—W wherein W is a 5 or 6-membered heteroaryl ring which is optionally substituted by a group —$SO_2(C_1-C_4)$alkyl;
n is 1, 2 or 3;
t is zero, 1, 2 or 3;
r is zero, 1, 2, 3 or 4;
$R_5$ is hydrogen, $(C_1-C_6)$alkyl, $NR_{16}R_{15}(C_1-C_6)$alkyl, or
$N^+R_{17}R_{15}R_{16}(C_1-C_6)$alkyl;
$R_6$ is hydrogen or $(C_1-C_6)$alkyl;
$R_7$ is hydrogen, $(C_1-C_6)$alkyl, $(C_1-C_6)$alkylcarbonyl, —$SO_2(C_1-C_4)$alkyl, or $NR_{16}R_{15}(C_1-C_6)$alkyl;
$R_8$ is hydrogen or $(C_1-C_6)$alkyl;
or, alternatively, $R_7$ and $R_8$, together with the nitrogen atom to which they are attached, form a $(C_5-C_7)$ heterocycloalkyl ring system which is optionally substituted by one or more groups $(C_1-C_6)$alkyl and oxo;
$R_{16}$ is hydrogen or $(C_1-C_6)$alkyl;
$R_{15}$ is hydrogen or $(C_1-C_6)$alkyl;
$R_{17}$ is hydrogen or $(C_1-C_6)$alkyl;
$R_2$ is hydrogen or —$SO_2R_4$, wherein $R_4$ is optionally substituted $(C_1-C_6)$alkyl, hydroxyl$(C_1-C_6)$alkyl, amino, mono- or di$(C_1-C_4)$alkylamino, wherein $(C_1-C_4)$alkyl may be optionally substituted, optionally substituted $(C_3-C_6)$-cycloalkyl, halogen, or optionally substituted phenyl;
$R_{14}$ is a group cyano or a group —C(O)—$XR_3$;
X is —O—, —$(CH_2)$—, or —NH—;
$R_3$ is:
  hydrogen;
  $(C_1-C_6)$alkyl;
  a group of formula -[Alk$^1$]-Z, wherein
    Alk$^1$ is a $(C_1-C_4)$alkylene radical and
    Z is:
      (i) —$NR_9R_{10}$, wherein $R_9$ and $R_{10}$ are independently hydrogen, optionally substituted $(C_1-C_6)$ alkyl or an optionally substituted $(C_3-C_6)$cycloalkyl group, or, taken together with the nitrogen to which they are attached, form an optionally substituted monocyclic $(C_5-C_7)$heterocyclic ring which may contain a further heteroatom selected from the group consisting of N, O, and S;
      or
      (ii) —$N^+R_{11}R_{12}R_{13}$, wherein $R_{11}$, $R_{12}$ and $R_{13}$ are each independently optionally substituted $(C_1-C_6)$alkyl or optionally substituted $(C_3-C_6)$cycloalkyl group; or any two of $R_{11}$, $R_{12}$ and $R_{13}$, taken together with the nitrogen to which they are attached, form an optionally substituted monocyclic $(C_5-C_7)$heterocyclic ring which may contain a further heteroatom selected from the group consisting of N, O, and S and the other of $R_{11}$, $R_{12}$ and $R_{13}$ is an optionally substituted $(C_1-C_6)$alkyl or an optionally substituted $(C_3-C_6)$cycloalkyl group; or
  a radical of formula —$(CH_2)_q$-[Q]-$(CH_2)_p$Z wherein Z is as above defined, q is an integer ranging from zero to 3, p is an integer ranging from zero to 3 and Q represents a divalent group selected from the group consisting of —O—, optionally substituted phenylene, optionally substituted ($C_5$-$C_7$)heterocycloalkylene, optionally substituted ($C_3$-$C_6$)cycloalkyl, and optionally substituted pyridinylene;
wherein if one or more groups —($C_1$-$C_6$)alkylN$^+$R$_{11}$R$_{12}$R$_{13}$ or —($C_1$-$C_6$)alkylN$^+$R$_{15}$R$_{16}$R$_{17}$ are present, they form quaternary salts with a pharmaceutically acceptable counter ion; and
wherein groups $R_5$, $R_6$, $R_7$, $R_8$, $R_{15}$, $R_{16}$, $R_{17}$, and n may assume the same or different meanings at each occurrence, if present in more than one group;
with the proviso that the compound of formula (I) is not:
5-(4-cyanophenyl)-2-(2-dimethylaminoethyl)-7-methyl-3-oxo-8-(3-trifluoromethylphenyl)-2,3,5,8-tetrahydro[1,2,4]triazolo[4,3-a]pyrimidine-6-carboxylic acid methyl ester;
5-(4-cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid 2-dimethylaminoethyl ester;
{2-[5-(4-cyanophenyl)-2,7-dimethyl-3-oxo-8-(3-trifluoromethylphenyl)-2,3,5,8-tetrahydro-[1,2,4]triazolo[4,3-a]pyrimidine-6-carbonyloxy]ethyl}-trimethylammonium; or
5-(4-cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid;
or a pharmaceutically acceptable salt thereof or an N-oxide thereof.

2. A compound, pharmaceutically acceptable salt thereof, or N-oxide thereof according to claim 1, wherein A is a group CH.

3. A compound, pharmaceutically acceptable salt thereof, or N-oxide thereof according to claim 1, wherein $R_2$ is hydrogen or a —SO$_2$R$_4$, wherein $R_4$ is ($C_1$-$C_6$)alkyl.

4. A compound, pharmaceutically acceptable salt thereof, or N-oxide thereof according to claim 1, wherein $R_{14}$ is a group —C(O)—XR$_3$.

5. A compound, pharmaceutically acceptable salt thereof, or N-oxide thereof according to claim 1, wherein X is —O— or —NH—.

6. A compound, pharmaceutically acceptable salt thereof, or N-oxide thereof according to claim 1, wherein $R_3$ is:
hydrogen;
($C_1$-$C_6$)alkyl; or
a radical of formula -[Alk$^1$]-Z,
wherein Alk$^1$ represents a ($C_1$-$C_4$)alkylene radical, and Z is:
(i) —NR$_9$R$_{10}$, wherein $R_9$ and $R_{10}$ are independently hydrogen or optionally substituted ($C_1$-$C_6$)alkyl; or
(ii) —N$^+$R$_{11}$R$_{12}$R$_{13}$, wherein $R_{11}$, $R_{12}$ and $R_{13}$ are each independently optionally substituted ($C_1$-$C_6$)alkyl.

7. A compound, pharmaceutically acceptable salt thereof, or N-oxide thereof according to claim 1, wherein $R_1$ is hydrogen, ($C_1$-$C_6$)alkyl, NR$_7$R$_8$($C_1$-$C_6$)alkyl, ($C_1$-$C_4$)alkenyl, phenyl($C_1$-$C_6$)alkyl, wherein such phenyl ring is optionally substituted by a group —($C_1$-$C_6$)alkylNR$_{15}$R$_{16}$ or by a group —($C_1$-$C_6$)alkylN$^+$R$_{15}$R$_{16}$R$_{17}$, —(CH$_2$)$_n$CONR$_5$R$_6$, —CH$_2$—(CH$_2$)$_n$NR$_5$SO$_2$R$_6$, —(CH$_2$)$_t$—($C_6$H$_4$)—SO$_2$($C_1$-$C_4$)alkyl, —(CH$_2$)$_r$SO$_2$($C_1$-$C_4$)alkyl, wherein such ($C_1$-$C_4$) alkyl is optionally substituted by a group —NR$_{15}$R$_{16}$ or —N$^+$R$_{15}$R$_{16}$R$_{17}$, —SO$_2$-phenyl, wherein such phenyl ring is optionally substituted by a group —($C_1$-$C_6$)alkylNR$_7$R$_8$, and —(CH$_2$)$_n$W, wherein W is a 5 or 6-membered heteroaryl ring, which is optionally substituted by a group —SO$_2$($C_1$-$C_4$)alkyl.

8. A compound, pharmaceutically acceptable salt thereof, or N-oxide thereof according to claim 1, which is a compound selected in the group consisting of:
5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
2-carbamoylmethyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
5-(4-cyanophenyl)-2-(2-dimethylamino-propyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
2-benzyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
2-allyl-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
5-(4-cyanophenyl)-2,7-dimethyl-3-oxo-8-(3-trifluoromethylphenyl)-2,3,5,8-tetrahydro-[1,2,4]triazolo[4,3-a]pyrimidine-6-carboxylic acid methyl ester;
(R)-5-(4-cyanophenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;
5-(4-cyano-phenyl)-2-{[(2-dimethylamino-ethyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;
5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid;
5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 2-dimethylamino-ethyl ester;
5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid 3-dimethylamino-propyl ester;
5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carboxylic acid ethylamide;
5-(4-cyano-2-methanesulfonyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;
5-(4-cyano-2-methanesulfonyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;
5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carbonitrile;
5-(4-cyano-phenyl)-2-(4-methanesulfonyl-phenyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;
5-(4-cyano-phenyl)-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;
(R)-5-(4-cyano-phenyl)-2-(4-methanesulfonyl-benzyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(4-cyano-phenyl)-2-(3-methanesulfonyl-propyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-cyano-phenyl)-2-(4-{[(2-dimethylamino-ethyl)-methyl-amino]-methyl}-benzenesulfonyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(R)-5-(4-cyano-phenyl)-2-[2-(4-methanesulfonyl-phenyl)-ethyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-cyano-phenyl)-2-(4-dimethylaminomethyl-benzyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

{4-[5-(4-cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-ylmethyl]-benzyl}-trimethyl-ammonium bromide;

5-(4-cyano-phenyl)-2-(5-methanesulfonyl-pyridin-2-ylmethyl)-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-cyano-phenyl)-7-methyl-3-oxo-2-[3-(2-oxo-pyrrolidin-1-yl)-propyl]-8-(3-trifluoromethyl-phenyl)-2,3,5,8-tetrahydro-[1,2,4]triazolo[4,3-a]pyrimidine-6-carboxylic acid methyl ester;

5-(4-cyano-phenyl)-2-{[(2-dimethylamino-ethyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-cyano-phenyl)-2-{[(3-dimethylamino-propyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

[2-({2-[5-(4-cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)-ethyl]-trimethyl-ammonium bromide;

[3-({2-[5-(4-cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)propyl]-trimethyl-ammonium bromide;

5-(4-cyano-phenyl)-2-{[(4-dimethylamino-butyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

5-(4-cyano-phenyl)-2-{[(5-dimethylamino-pentyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

[4-({2-[5-(4-cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)-butyl]-trimethylammonium bromide;

[5-({2-[5-(4-cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)pentyl]-trimethyl-ammonium bromide;

(R)-[5-({2-[5-(4-cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-acetyl}-methyl-amino)pentyl]-trimethyl-ammonium chloride;

2-[3-(acetyl-methyl-amino)-propyl]-5-(4-cyano-phenyl)-7-methyl-3-oxo-8-(3-trifluoromethylphenyl)-2,3,5,8-tetrahydro-[1,2,4]triazolo[4,3-a]pyrimidine-6-carboxylic acid methyl ester;

5-(4-cyano-phenyl)-2-[3-(methanesulfonyl-methyl-amino)-propyl]-7-methyl-3-oxo-8-(3-trifluoromethyl-phenyl)-2,3,5,8-tetrahydro-[1,2,4]triazolo[4,3-a]pyrimidine-6-carboxylic acid methyl ester;

(3-{3-[5-(4-cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-propane-1-sulfonyl}-propyl)-trimethylammonium toluene-4-sulfonate;

(R)-(3-{3-[5-(4-cyano-phenyl)-6-methoxycarbonyl-7-methyl-3-oxo-8-(3-trifluoromethyl-phenyl)-5,8-dihydro-[1,2,4]triazolo[4,3-a]pyrimidin-2-yl]-propane-1-sulfonyl}-propyl)-trimethylammonium chloride;

5-(4-cyano-phenyl)-7-methyl-3-oxo-8-(3-trifluoromethyl-phenyl)-2,3,5,8-tetrahydro-[1,2,4]triazolo[4,3-a]pyrimidine-6-carbonitrile;

(3-{3-[6-cyano-5-(4-cyano-phenyl)-7-methyl-3-oxo-8-(3-trifluoromethyl-phenyl)-5,8-dihydro-[1,2,4]triazolo[4,3-a]pyrimidin-2-yl]-propane-1-sulfonyl}-propyl)-trimethylammonium toluene-4-sulfonate; and (R)-5-(4-cyano-phenyl)-2-{[(5-dimethylamino-pentyl)-methyl-carbamoyl]-methyl}-7-methyl-3-oxo-8-(3-trifluoromethyl-phenyl)-2,3,5,8-tetrahydro-[1,2,4]triazolo[4,3-a]pyrimidine-6-carboxylic acid methyl ester;

or a pharmaceutically acceptable salt of said compound or an N-oxide of said compound.

9. A compound, pharmaceutically acceptable salt thereof, or N-oxide thereof according to claim 1, which is a compound represented by formula (I)' wherein the absolute configuration of carbon (1) is that shown below:

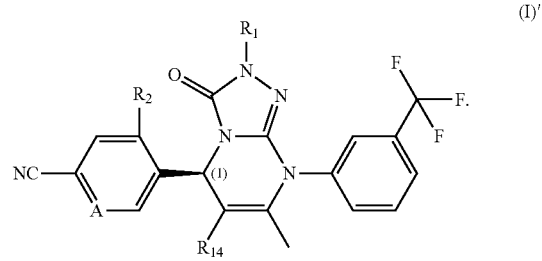

(I)'

10. A compound, pharmaceutically acceptable salt thereof, or N-oxide thereof according to claim 1, which is a pharmaceutically acceptable salt.

11. A pharmaceutical composition, comprising a compound, pharmaceutically acceptable salt thereof, or N-oxide thereof according to claim 1 and a pharmaceutically acceptable carrier or excipient.

12. A pharmaceutical composition according to claim 11, which is in a form suitable for oral administration or administration by the pulmonary route.

13. A method for the treatment of a disease or condition selected from the group consisting of asthma, rhinitis, psoriasis, atopic dermatitis, non-atopic dermatitis, Crohn's disease, ulcerative colitis, or irritable bowel disease chronic obstructive pulmonary disease, bronchiectasis, chronic bronchitis, lung fibrosis, pneumonia, acute respiratory distress syndrome, pulmonary emphysema, smoking-induced emphysema, and cystic fibrosis, comprising administering to an effective amount of a compound, pharmaceutically acceptable salt thereof, or N-oxide thereof according to claim 1 to a subject in need thereof.

14. A method according to claim 13, wherein said disease or condition is chronic obstructive pulmonary disease, bronchiectasis, chronic bronchitis, lung fibrosis, pneumonia, acute respiratory distress syndrome, pulmonary emphysema, smoking-induced emphysema, or cystic fibrosis.

15. A method according to claim 13, wherein said disease or condition is asthma, rhinitis, psoriasis, atopic dermatitis, non-atopic dermatitis, Crohn's disease, ulcerative colitis, or irritable bowel disease.

16. A method according to claim 13, wherein said disease or condition is asthma.

17. A method according to claim 13, wherein said disease or condition is chronic obstructive pulmonary disease.

* * * * *